(12) United States Patent
Atto et al.

(10) Patent No.: US 11,576,700 B2
(45) Date of Patent: *Feb. 14, 2023

(54) RADIALLY EXPANDABLE CANNULA SYSTEMS AND METHODS FOR USE

(71) Applicant: XPAN Inc., Nobleton (CA)

(72) Inventors: Zaid Atto, Nobleton (CA); Seray Cicek, York (CA); Chevis Dilbert, Toronto (CA)

(73) Assignee: XPAN Inc., Nobleton (CA)

( * ) Notice: Subject to any disclaimer, the term of this patent is extended or adjusted under 35 U.S.C. 154(b) by 285 days.

This patent is subject to a terminal disclaimer.

(21) Appl. No.: 16/801,088

(22) Filed: Feb. 25, 2020

(65) Prior Publication Data

US 2020/0261115 A1  Aug. 20, 2020

Related U.S. Application Data

(63) Continuation of application No. PCT/CA2018/051072, filed on Sep. 5, 2018.
(Continued)

(51) Int. Cl.
*A61B 17/34* (2006.01)

(52) U.S. Cl.
CPC ...... *A61B 17/3423* (2013.01); *A61B 17/3498* (2013.01); *A61B 17/3462* (2013.01); *A61B 2017/3486* (2013.01)

(58) Field of Classification Search
CPC ............ A61B 17/3423; A61B 17/3498; A61B 17/3462–2017/3466; A61B 17/3431;
(Continued)

(56) References Cited

U.S. PATENT DOCUMENTS 3,509,883 A  5/1970  Dibelius
3,789,852 A  2/1974  Kim
(Continued)

FOREIGN PATENT DOCUMENTS

CA  2052310 A1  4/1992
CA  2550605 A1  7/2005
(Continued)

OTHER PUBLICATIONS

European Patent Office, Supplemental European Search Report for associated European Patent Application No. 18854871, dated Apr. 7, 2021, 8 pages.
(Continued)

*Primary Examiner* — Darwin P Erezo
*Assistant Examiner* — Brigid K Byrd
(74) *Attorney, Agent, or Firm* — William A English; Vista IP Law Group LLP

(57) ABSTRACT

A radially expandable trocar, port or cannula system is provided for use in minimally invasive surgeries. The cannula creates a port access with an initial small internal diameter. The passage of the cannula devices is defined by a plurality of elongate rigid members. A number of mechanisms are provided for expanding the passage of the cannula devices, by moving the plurality of elongate rigid members towards a larger radial location, thereby creating a larger internal diameter for the port. The elongate rigid members can be prevented from unintended movement when the system is at the un-expanded state, during expansion and when it is expanded to the desired larger diameter. Exemplary embodiments include methods of preventing gas loss from the tissue that would occur through the gaps created during expansion.

19 Claims, 61 Drawing Sheets

Related U.S. Application Data

(60) Provisional application No. 62/554,802, filed on Sep. 6, 2017.

(58) Field of Classification Search
CPC ........ A61B 17/3439; A61B 2017/3445; A61B 17/3468; A61B 2017/345–3452; A61B 2017/3443–3445; A61B 2017/3433; A61B 17/3421–2017/3429
See application file for complete search history.

(56) References Cited

U.S. PATENT DOCUMENTS

| | | | |
|---|---|---|---|
| 4,716,901 A | 1/1988 | Jackson | |
| 4,899,729 A | 2/1990 | Gill | |
| 5,122,122 A | 6/1992 | Allgood | |
| 5,139,511 A | 8/1992 | Gill | |
| 5,183,464 A | 2/1993 | Dubrul | |
| 5,197,971 A | 3/1993 | Bonutti | |
| 5,295,994 A | 3/1994 | Bonutti | |
| 5,312,417 A | 5/1994 | Wilk | |
| 5,338,305 A | 8/1994 | Plyley | |
| 5,916,232 A | 6/1999 | Hart | |
| 5,944,691 A | 8/1999 | Querns | |
| 7,896,897 B2 | 3/2011 | Gresham | |
| 8,292,851 B2 | 10/2012 | Ferrari | |
| 8,518,087 B2 | 8/2013 | Lopez | |
| 8,591,538 B2 | 11/2013 | Gellman | |
| 2002/0042603 A1* | 4/2002 | Palmer | A61B 17/3421 606/1 |
| 2003/0014068 A1 | 1/2003 | Bonutti | |
| 2003/0023259 A1 | 1/2003 | Dubrul | |
| 2004/0059348 A1* | 3/2004 | Geske | A61N 1/056 606/129 |
| 2004/0093001 A1* | 5/2004 | Hamada | A61B 17/0206 606/190 |
| 2004/0116954 A1 | 6/2004 | Pagliuca | |
| 2006/0206008 A1 | 9/2006 | Dalton | |
| 2006/0212062 A1 | 9/2006 | Farascioni | |
| 2007/0010716 A1* | 1/2007 | Malandain | A61B 90/30 600/219 |
| 2009/0024158 A1 | 1/2009 | Viker | |
| 2009/0209913 A1 | 8/2009 | Ferrari | |
| 2009/0306586 A1 | 10/2009 | Ross et al. | |
| 2011/0144589 A1* | 6/2011 | Ortiz | A61B 17/3462 604/164.03 |
| 2012/0172668 A1 | 7/2012 | Kerns | |
| 2013/0103048 A1* | 4/2013 | Burg | A61B 17/3439 606/129 |
| 2014/0276584 A1 | 9/2014 | Castro | |

FOREIGN PATENT DOCUMENTS

| | | |
|---|---|---|
| CA | 2698872 A1 | 10/2010 |
| CN | 107049440 A | 8/2017 |
| KR | 101287138 B1 | 7/2013 |
| WO | 2005089433 A2 | 9/2005 |
| WO | 2007056627 A1 | 5/2007 |
| WO | 2008121794 A1 | 10/2008 |
| WO | 2010080497 A2 | 7/2010 |
| WO | 2011072098 A2 | 6/2011 |
| WO | 2011130532 A2 | 10/2011 |
| WO | 2013119577 A1 | 8/2013 |
| WO | 2015040617 A1 | 3/2015 |
| WO | 2017040275 A1 | 3/2017 |

OTHER PUBLICATIONS

Fish, S., Boult Wade Tennant response to extended European Search Report for associated European Patent Application No. 18854871, dated Nov. 15, 2021, 18 pages.

United States Patent and Trademark Office, Office Action for associated U.S. Appl. No. 17/534,314, dated Feb. 1, 2022, 23 pages.

English, William A., Vista IP Law Group LLP response to Office Action for associated U.S. Appl. No. 17/534,314, dated Feb. 3, 2022, 13 pages.

* cited by examiner

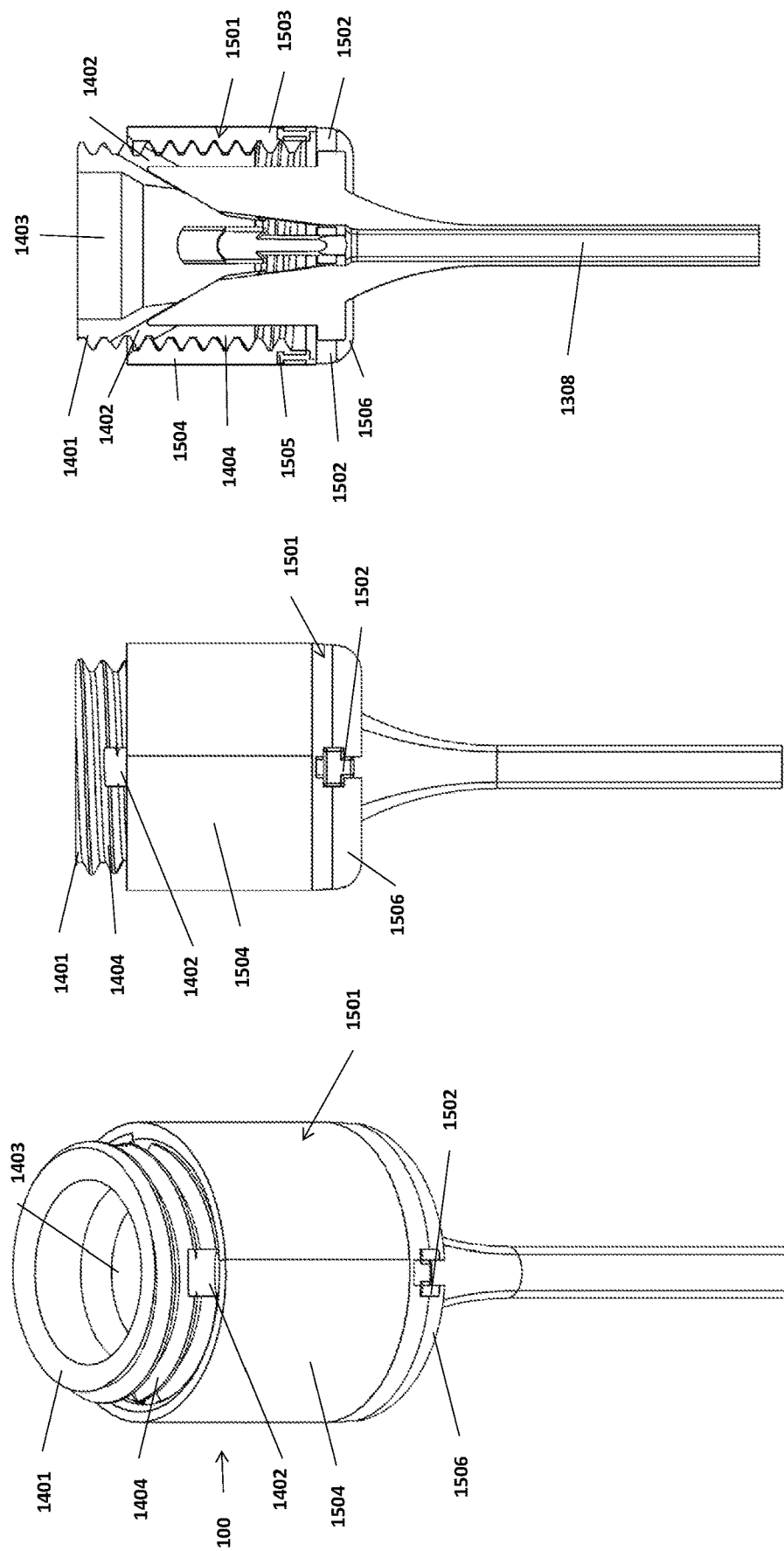

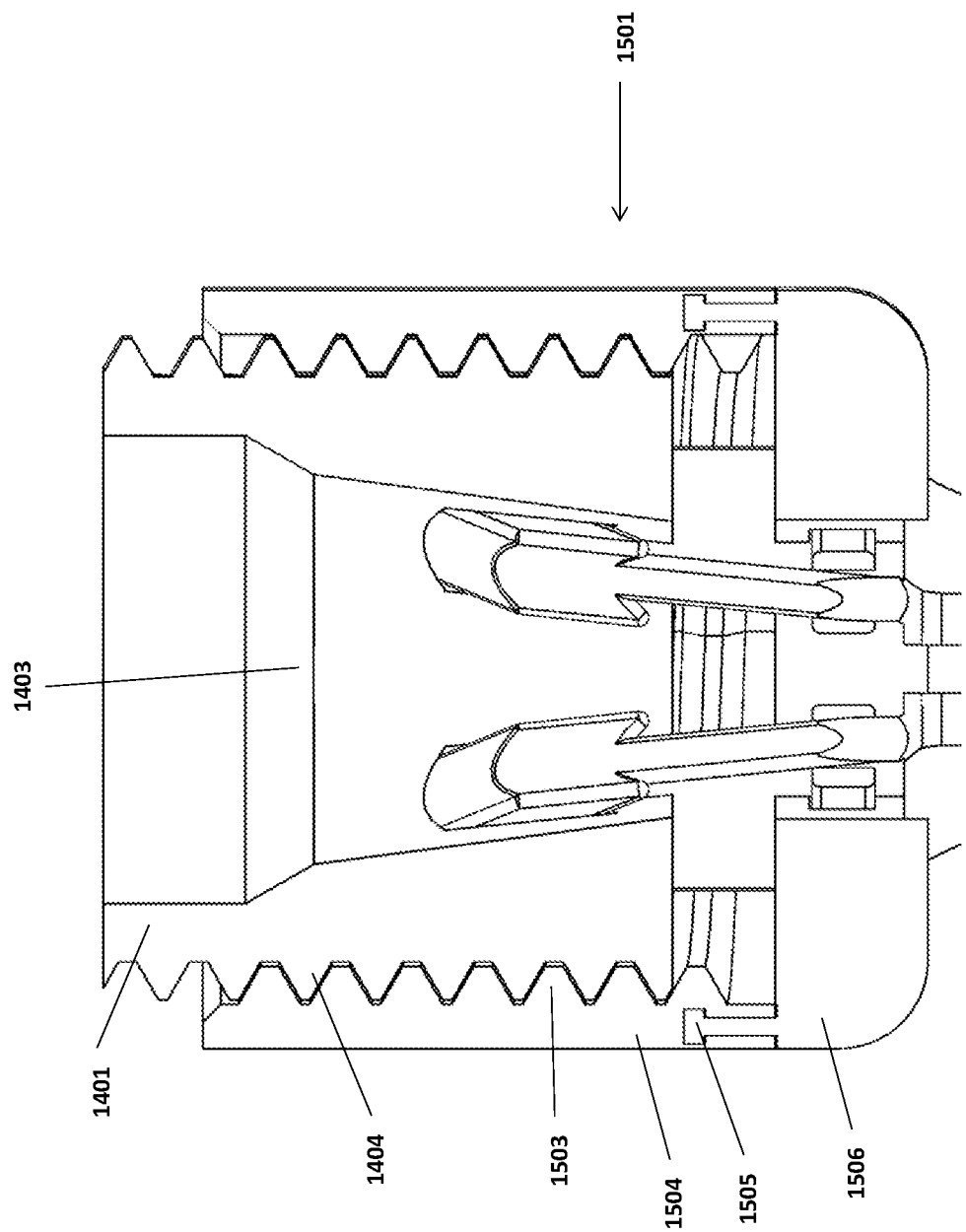

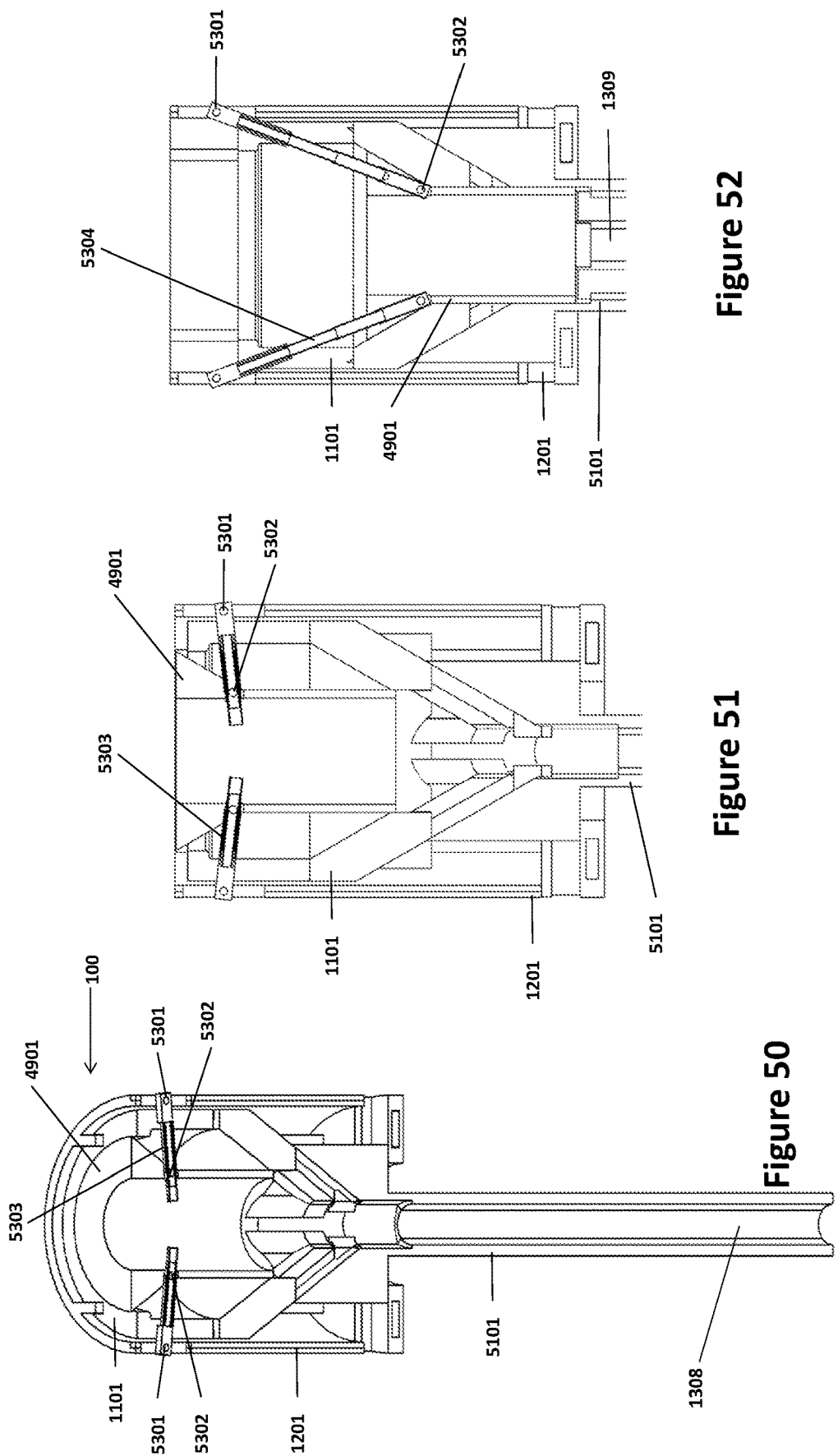

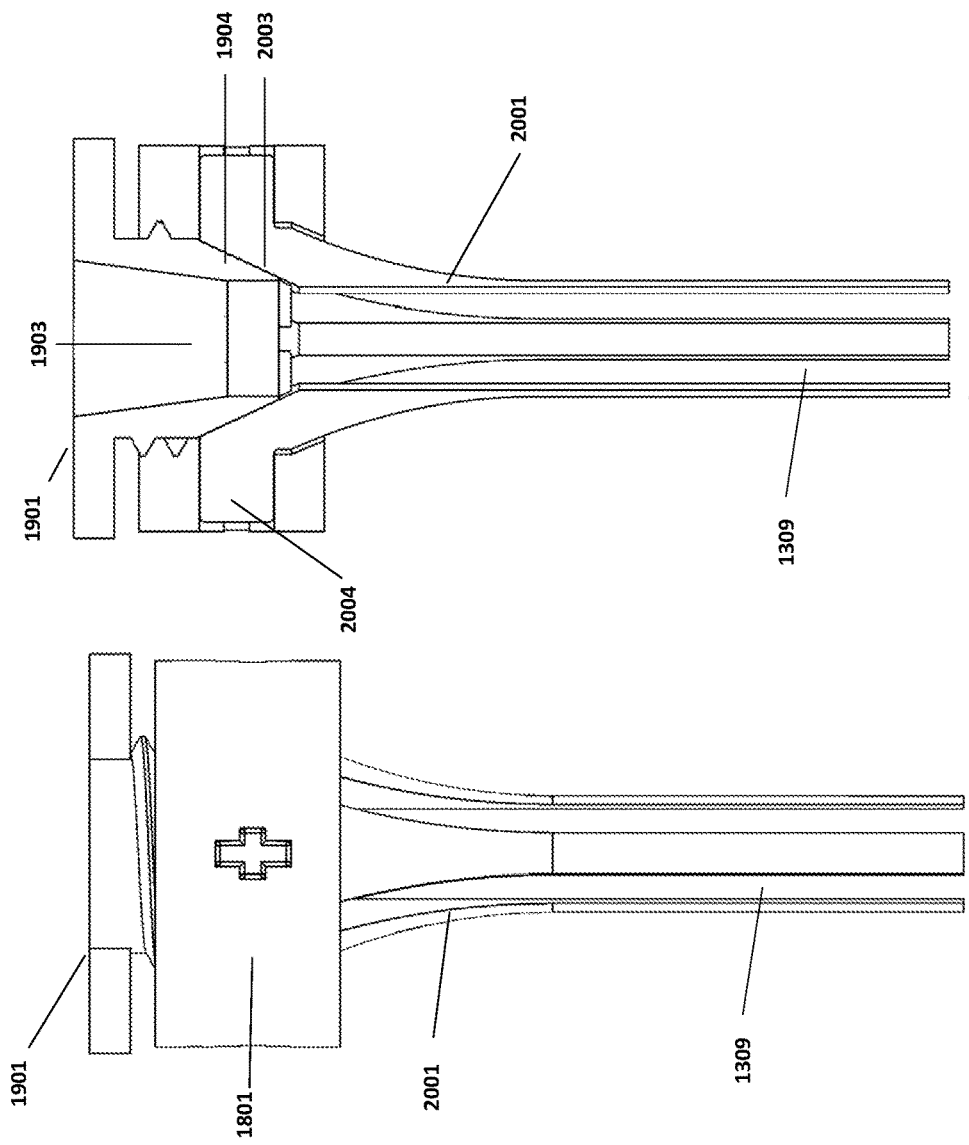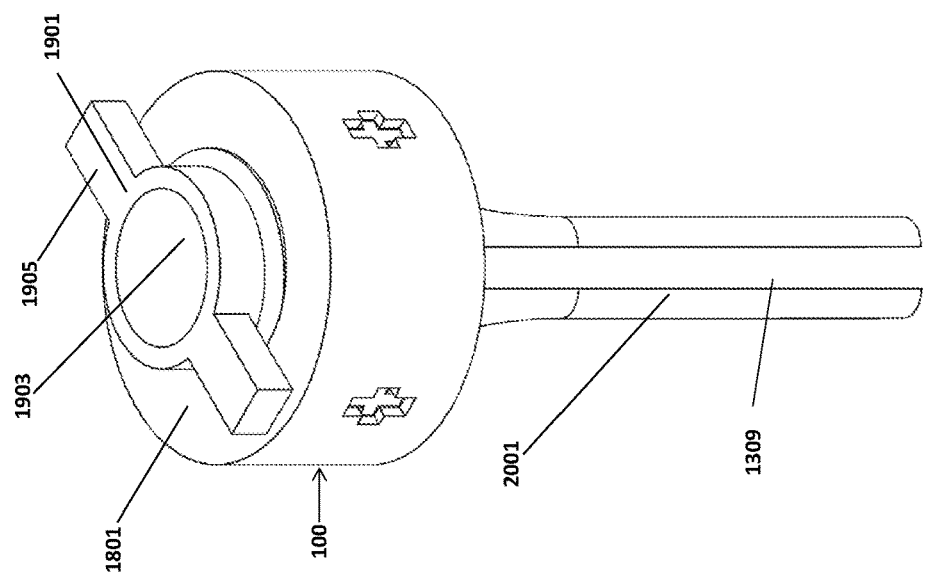

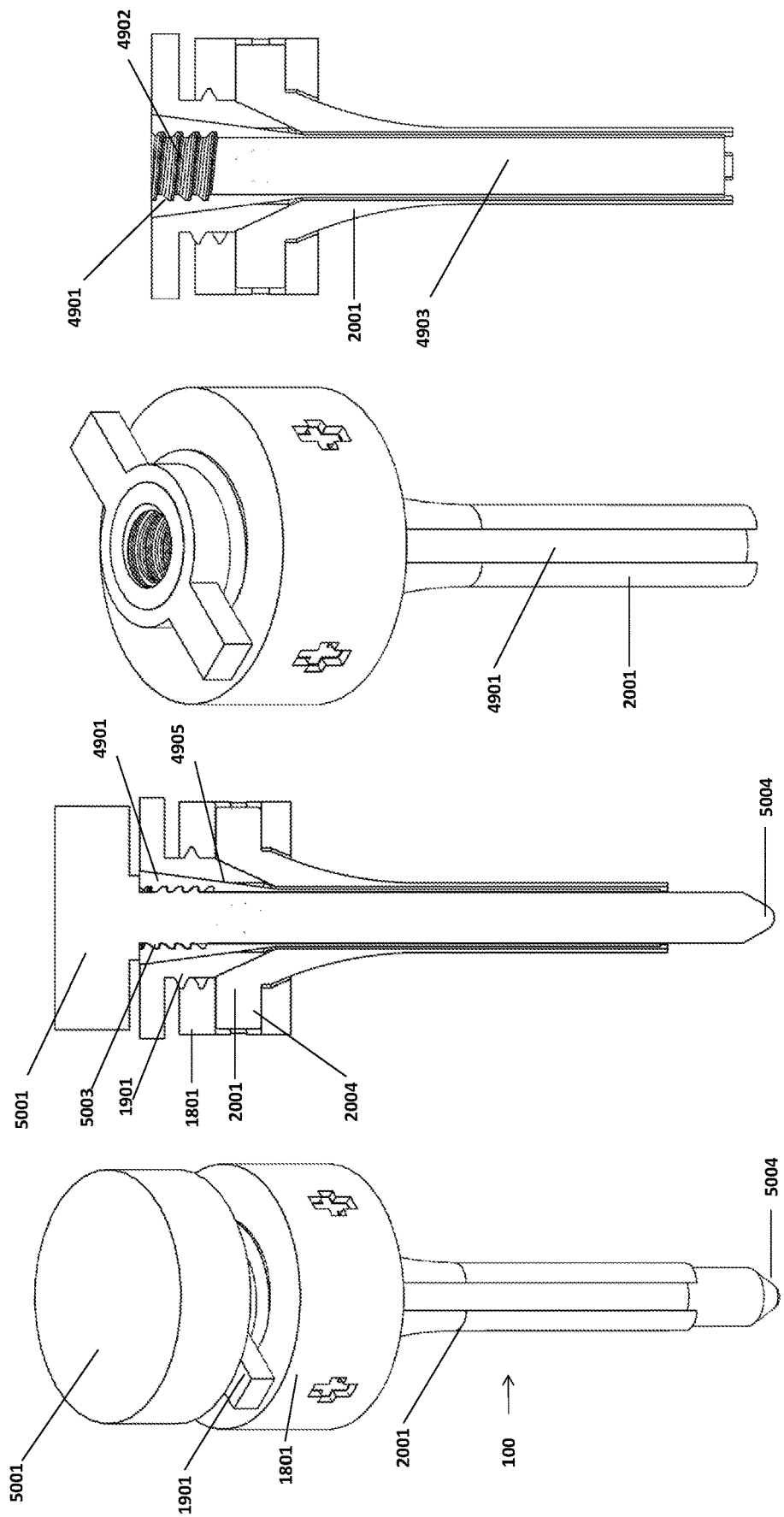

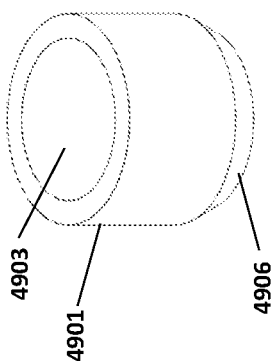
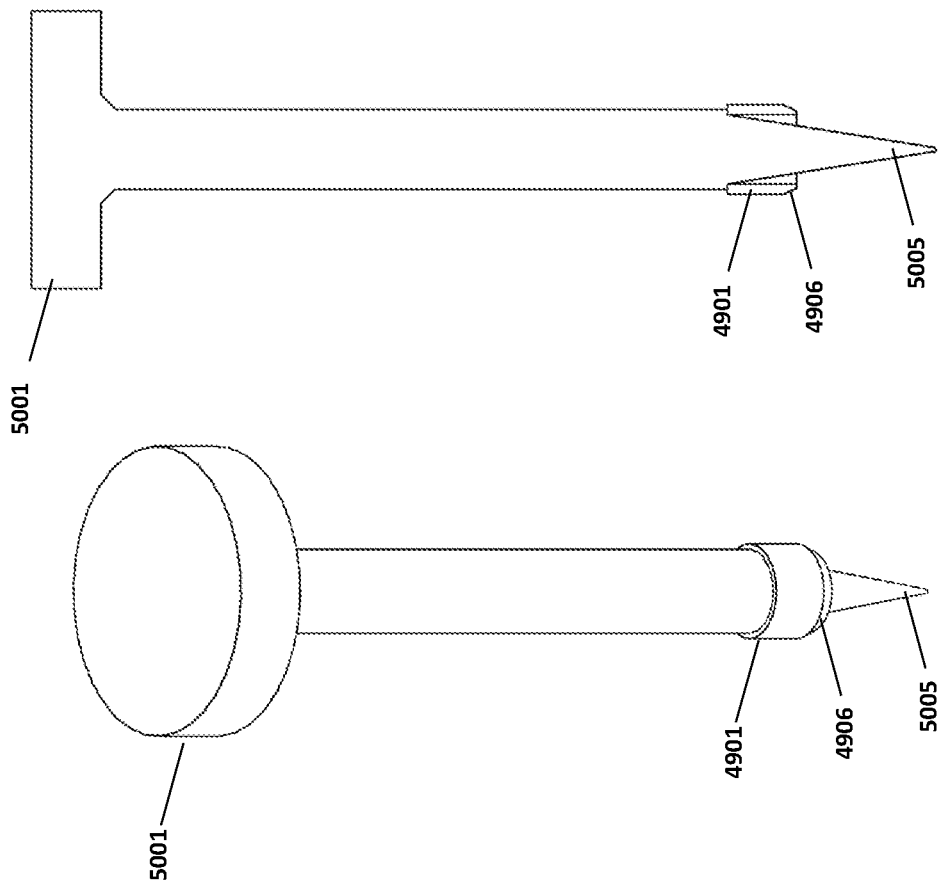

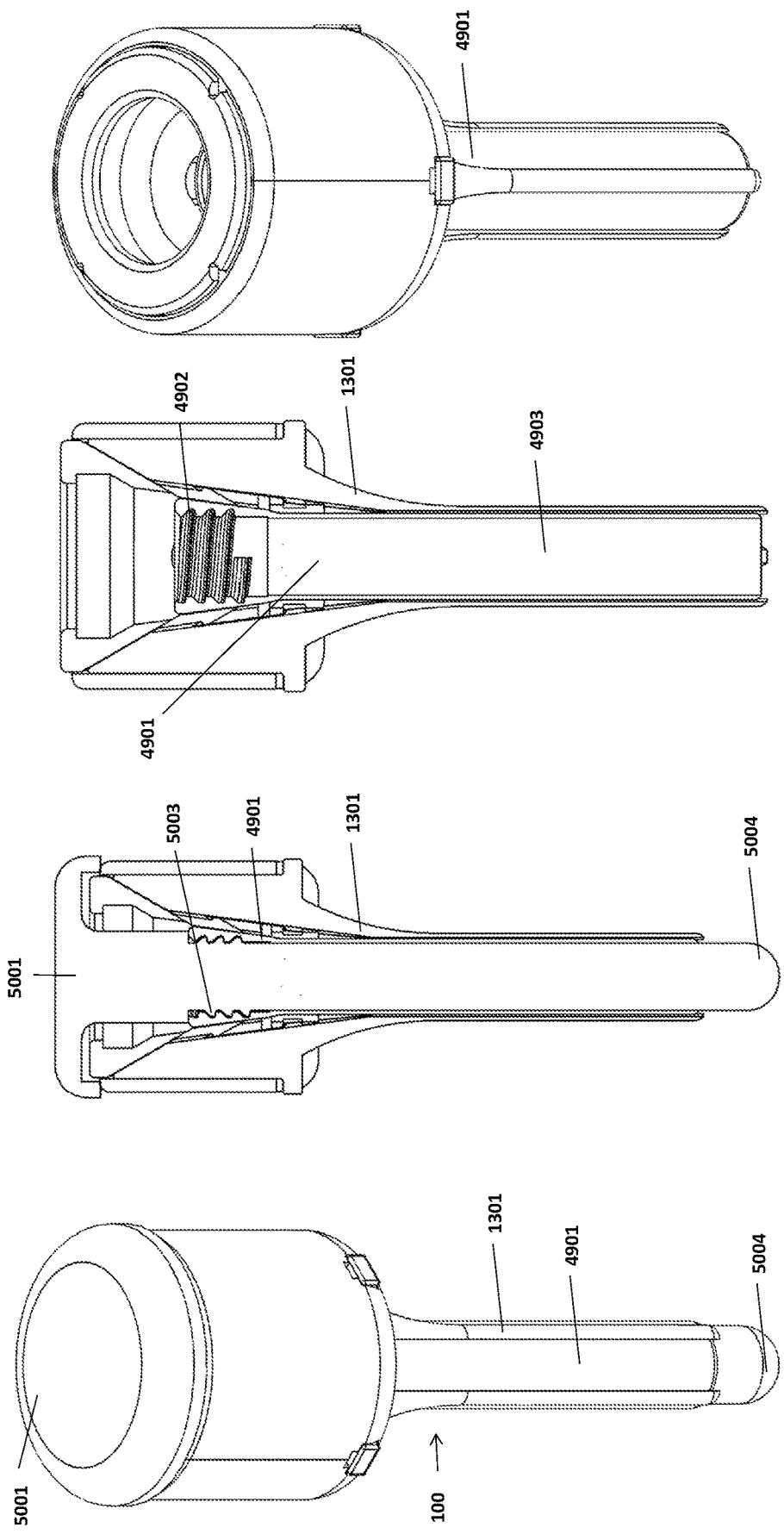

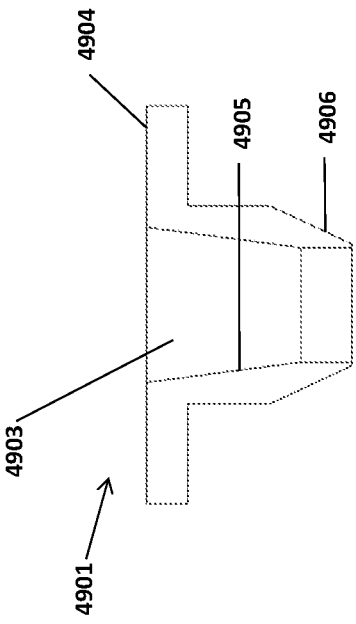
Figure 127
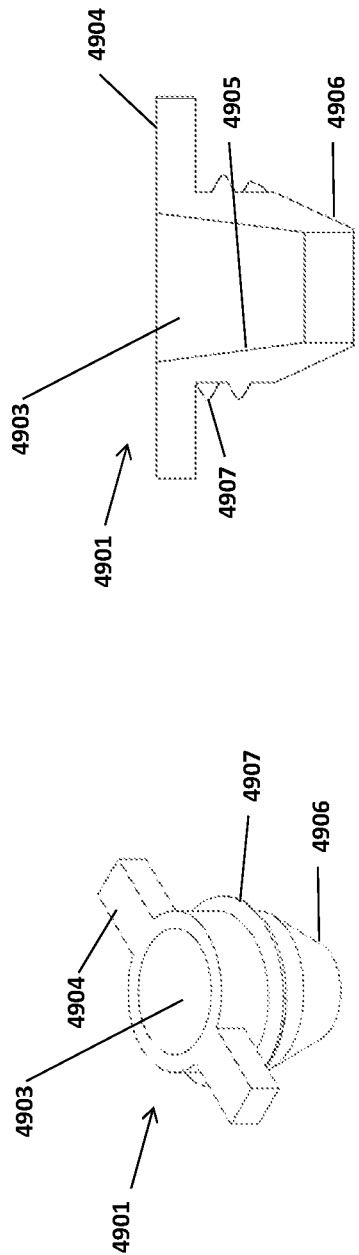
Figure 128
Figure 130
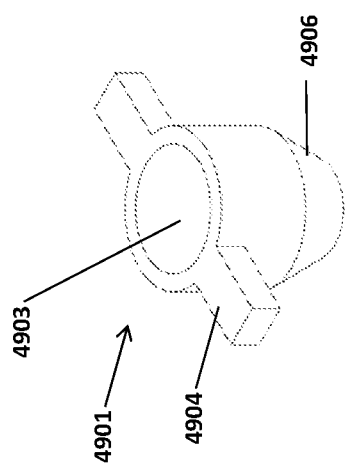
Figure 129

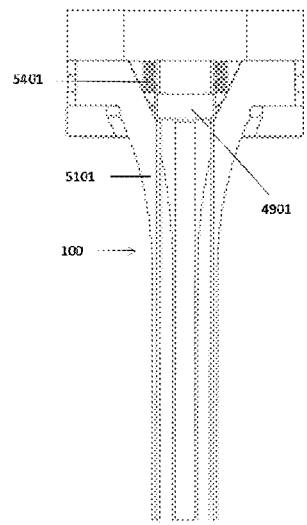
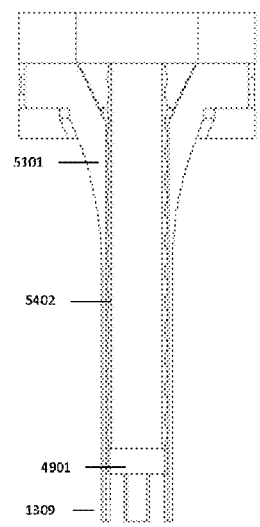
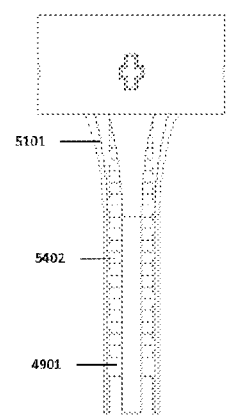
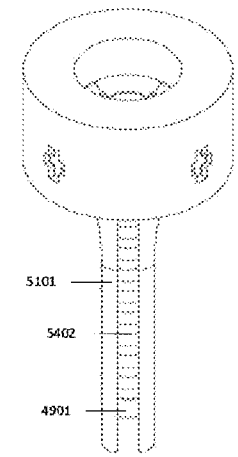
Figure 143   Figure 144   Figure 145   Figure 146
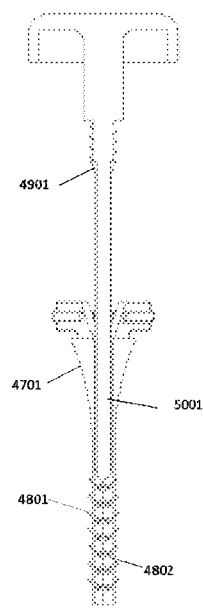
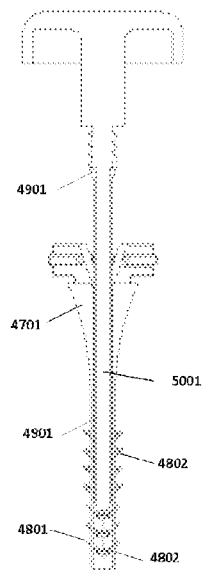
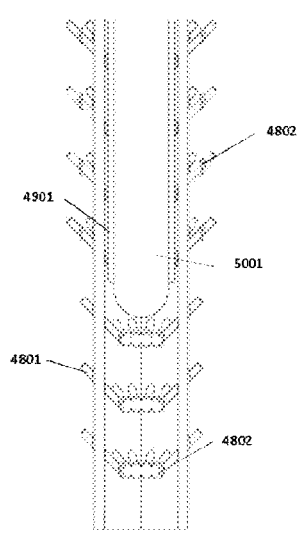
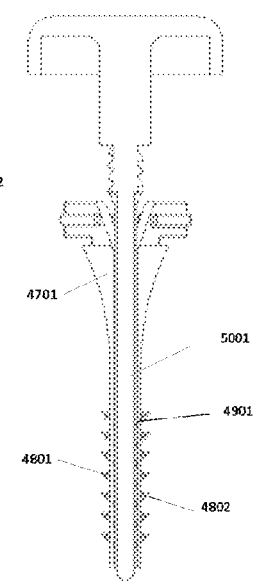
Figure 147   Figure 148   Figure 149   Figure 150

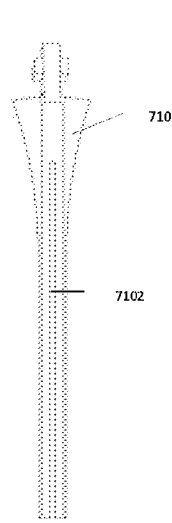
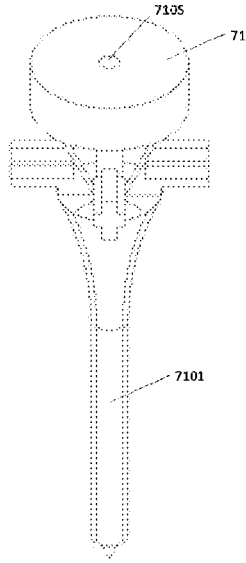
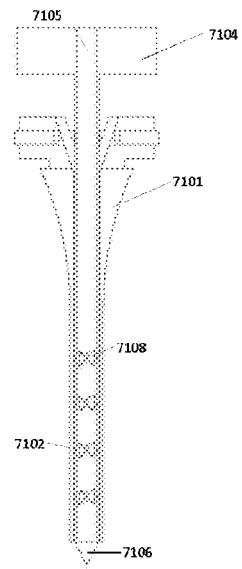
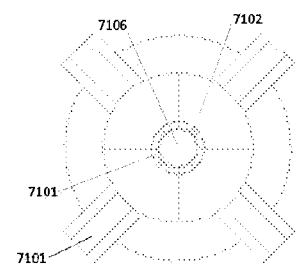
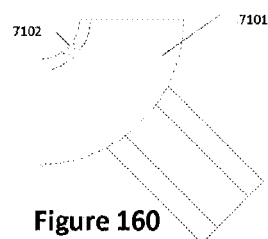
Figure 156   Figure 157   Figure 158   Figure 159
Figure 160
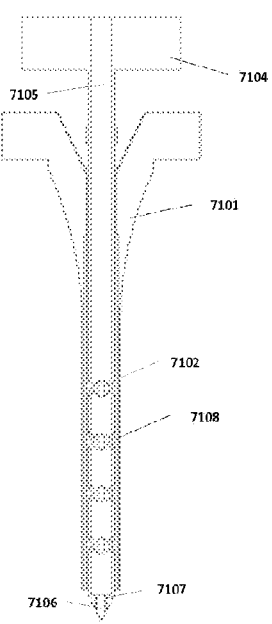
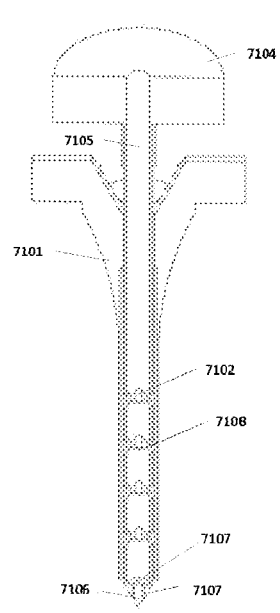
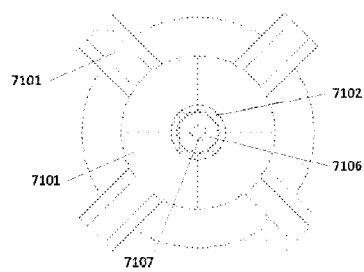
Figure 161   Figure 162   Figure 163

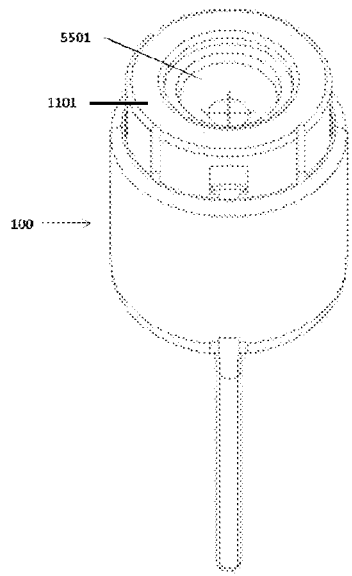
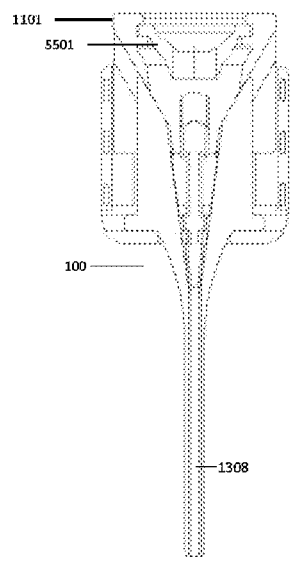
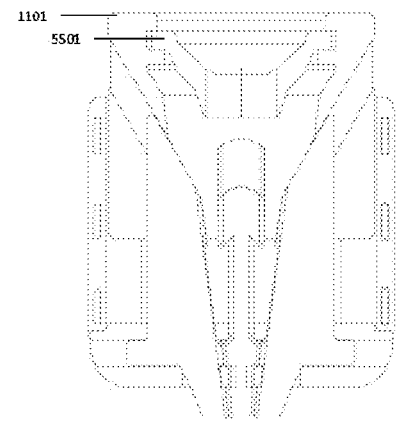
Figure 164　　Figure 165　　Figure 166
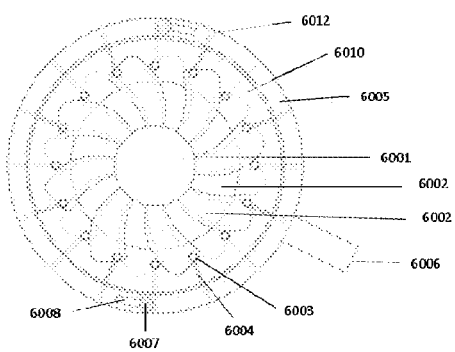
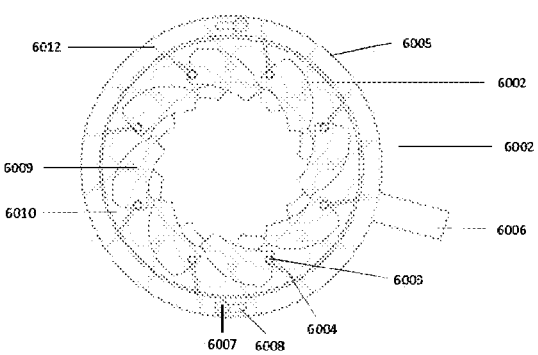
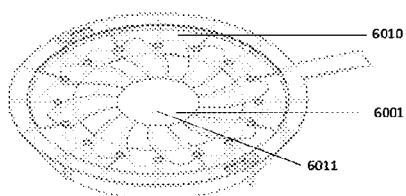
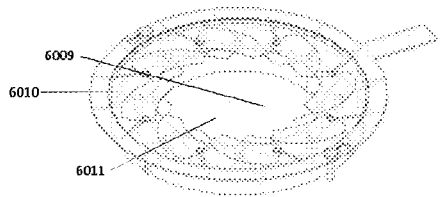
Figure 167　　Figure 169
Figure 168　　Figure 170

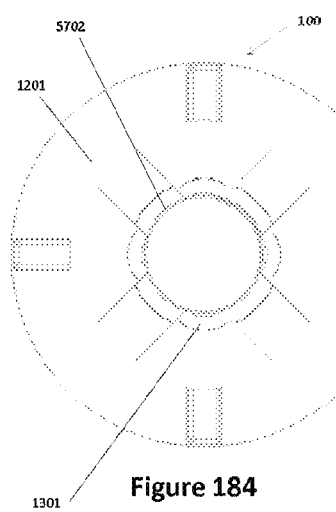
Figure 184
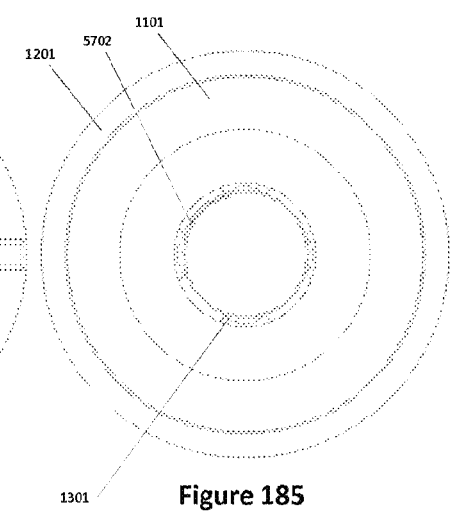
Figure 185
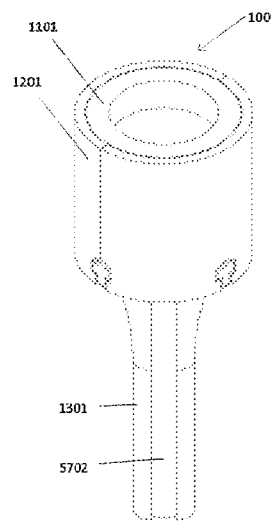
Figure 186
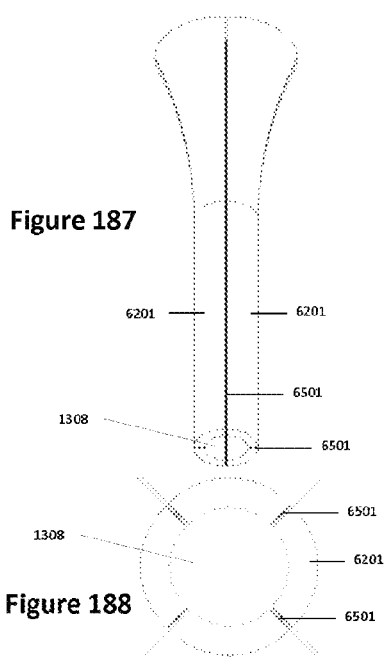
Figure 187
Figure 188
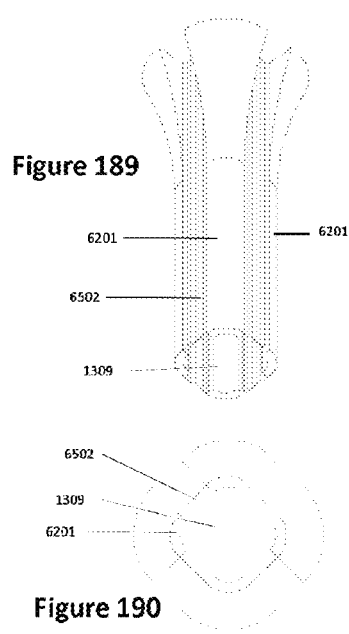
Figure 189
Figure 190

ND METHODS FOR USE

RADIALLY EXPANDABLE CANNULA SYSTEMS AND METHODS FOR USE

RELATED APPLICATION DATA

This application is a continuation of International Application No. PCT/CA2018/051072, filed Sep. 5, 2018, which claims the benefit of U.S. provisional patent application Ser. No. 62/554,802, filed Sep. 6, 2017, and Canadian Patent Application No. 2993590 filed on Jan. 31, 2018, the disclosure of which is expressly incorporated by reference herein.

TECHNICAL FIELD

The technical field relates generally to methods and devices used in minimally invasive surgeries or key-hole surgeries. For example, the technical field relates to cannula devices and trocar devices for insertion in an incision.

BACKGROUND

In minimally invasive surgeries, a small incision is made. Then a cannula or a port device (known as trocar) is inserted through the incision to create a tunnel through which surgical devices can be passed through to perform the minimally invasive procedure. The surgeons aim to minimize the size of the tools they use and hence minimize the diameter of the trocars they use in order to minimize scarring, post-operative pain, risk of infection and overall injury. Therefore, the surgeon typically begins the procedure by using a small trocar device. In laparoscopic procedures the small trocars are typically rated at having a cannula with an internal diameter of 5 mm, for example. Some instruments however have larger diameter, and therefore require the use of larger diameter trocars such as 10 mm or 12 mm trocars.

In the cases where a large trocar (such as 10 mm or 12 mm trocars) must be utilized, there is a need to reduce the incision size, and the defect size in the patient's anatomy that is caused by insertion of these large trocars. Some large trocars are inserted into tissue with blunt-tip obturators or have obturators with dilating tips obturator in order to reduce injury. However, there are no known trocars with dilating cannula being used in the field.

In certain situations, a need may arise to enlarge the diameter of a small port in order to use a larger instrument. These situations may be pre-planned or may be due to emergency situations such as a sudden bleeding or may be due to un-anticipated difficult anatomy. Such reasons (and more) would drive the need to upsize the trocar device; to replace small diameter trocar with a larger diameter one instead.

In laparoscopic surgeries, this upsizing can cause loss of the abdominal pneumoperitoneum, which needs to be re-stablished after the upsizing. It also presents a risk of injury to patient as the secondary trocar insertion may go through a different path through the abdominal wall, presenting an opportunity to injure an internal organ or cause bleeding. Furthermore, conventional upsizing requires that the small incision is increased prior to inserting the larger trocar, and upon the completion of surgery that the fascia and skin are stitched to decrease risk of herniation.

One popular method of trocar upsizing is to first insert a sleeve device (with mesh and polymer coating) through the abdominal wall, through which, a small trocar is inserted, then upon need of upsizing, a bigger trocar is inserted through the sleeve after the small one has been removed. Although this system prevents need to stitch fascia and abdominal wall after upsizing and prevents the risk of going through a different pathway, it presents few problems. It still allows leakage of gas during upsizing, and the insertion of a larger trocar through the sleeve still requires significant insertion force that present a risk of injury to patient. Furthermore, this method still requires use of 2 trocar devices in addition to the sleeve.

In some scenarios the trocars used during surgery become dislodged during use, and may sometime be accidentally removed from the tissue, presenting an injury risk upon re-entry, causing inefficiency and pneumoperitoneum loss. Therefore, there is a need of trocars providing better stability and retention in the tissue of the patient.

In minimal invasive neurosurgeries such as tumor resections, and hematoma evacuations, a cannulation device or a port of a small diameter is often inserted through the brain tissue towards the target site. However, in cases where larger access is needed, the diameter of the cannula may then gradually increased by successive insertion of larger cannulas over the smaller ones. This is a time-consuming process and induces higher stress and risk of damage to the tissue proximal to the skull as the larger cannulas are inserted and an uneven distribution of force is created with a gradient towards the upper portion of the brain tissue. In other techniques when larger access is needed, the insertion of a large diameter port with image guidance technologies may be used. However, insertion of a large diameter port into delicate brain tissue may cause critical tissue and nerve injury. Thus, a more minimally invasive method to create larger access in brain tissue is also needed.

Additional difficulties with existing devices may be appreciated in view of the Detailed Description of Example Embodiments, herein below.

SUMMARY

In an example embodiment, an expandable cannula device has: a first ring; a plurality of elongate rigid members collectively defining an aperture and operably connected to the first ring; and a second ring slidable in an axial direction with respect to the first ring, the second ring being operably connected to the elongate rigid members so that sliding of the second ring with respect to the first ring causes the plurality of elongate rigid members to move away from each other and increase a size of the aperture.

In some example embodiment, another cannula device is provided. The cannula device comprises a first housing, a plurality of elongate rigid members, and a second housing. The first housing defines a throughbore. The plurality of elongate rigid members cooperatively defines a passage, which is axially aligned with the first throughbore. The plurality of elongate rigid members is connected to the first housing. The second housing also defines a throughbore. The second housing is connected to the plurality of elongate rigid members and the movement of the second housing with respect to the first housing causes the elongate rigid members to move away from each other and increase the size of the passage.

In some example embodiment, yet another cannula device is provided. The cannula device comprises a housing, a plurality of elongate rigid members, and an actuating member. The housing defines a first throughbore. The plurality of elongate rigid members cooperatively defines a passage. The plurality of elongate rigid members is connected to the housing and the passage is axially aligned with the first throughbore. The actuating member also defines a throughbore. When assembled, the throughbore of the actuating member is axially aligned with the passage. The axial movement of the actuating member with respect to the housing causes the plurality of elongate rigid members to radially move relative to each other.

In some example embodiment, a cannula device is provided that comprises a housing, a plurality of elongate rigid members and an actuating pin. The housing defines a throughbore. The plurality of elongate rigid members is connected to the housing, and the plurality of elongate rigid members cooperatively defines a passage, which is axially aligned with the throughbore. The actuating pin extends through the housing and is in contact with the plurality of elongate rigid members. The actuating pin moves spirally relative to the axis of the throughbore and causes the plurality of elongate rigid members to move radially.

In some embodiment, a cannula device is provided that comprises a housing, a plurality of elongate rigid members, a hub, and at least one rigid member. The housing defines a throughbore. The plurality of elongate rigid members is connected to the housing and cooperatively defines a passage that is axially aligned with the throughbore. The hub is connected to the housing and comprises at least one rotatable feature that is coupled to the at least one rigid member so that the rotation of the at least one rotatable feature causes the at least one rigid member to move into and along the passage. The at least one rigid member has a circumference that is larger than an inner circumference of the passage so that the movement of the at least one rigid member causes the plurality of elongate rigid members to move radially away from each other to enlarge the passage.

In some embodiment, a cannula device is provided that comprises a housing, a plurality of elongate rigid members, and a compressible member. The housing defines a throughbore. The plurality of elongate rigid members is connected to the housing and cooperatively defines a passage. Each elongate rigid member is hingedly connected to another elongate rigid member. The compressible member is placed around the plurality of elongate rigid members to restrict movement of the elongate rigid members.

In some embodiments, a cannula device is provided that comprises a cannula with at least one blade, which comprises a sharp edge and a spine, disposed in the exterior wall of the cannula. The blade is biased toward the inside of the cannula, and the sharp edge of the blade is normally embedded within the exterior wall of the cannula, while the spine is exposed from the inside of the cannula. When an outward force is applied to the spine, the sharp edge is exposed from the exterior surface of the cannula.

A method for creating a passage into a subject is also provided. The expandable cannula device can be inserted into a subject and then the elongate rigid members are moved away from each other to enlarge the passage. Use of the cannula device is also provided.

In some embodiments, moveable frictional surface features are provided in the walls of a cannula device defining a passage.

BRIEF DESCRIPTION OF THE DRAWINGS

FIG. 43 is an isometric view of an expandable cannula device embodiment, at an unexpanded state, wherein the second housing is away from the first housing, and rotation of the second housing about the central axis of the device causes movement of the second housing relative to the first housing;

FIG. 44 is a side view of example embodiment shown in FIG. 43;

FIG. 45 is a cross-sectional view of example embodiment shown in FIG. 44

FIG. 49 is a cross-sectional close-up view of the first and second housings of expandable cannula device embodiments of FIGS. 43-48, at an expanded state where the second housing is close to the first housing;

FIG. 50 is an isometric cross-sectional view of an embodiment of an expandable cannula device comprising an insertable member with a telescoping actuation mechanism attached to the second housing, such that movement of the second housing proximally closer to the first housing causes the insertable member to move distally along the central axis of the device;

FIG. 51 is a cross sectional close-up view of FIG. 50, wherein the second housing is away from the first housing, such that the telescoping actuation mechanism is unexpanded and configures the insertable member to be in a proximal region to the plurality of the unexpanded elongate rigid members;

FIG. 52 is a cross sectional close-up view of the same embodiment of FIGS. 50-51, wherein the second housing is moved closer to the first housing, configuring the device to become expanded and causing telescoping actuation mechanism to become expanded and thus move the insertable member distally into the expanded passage comprised by the plurality of elongate rigid members.

FIG. 56 is an isometric view of the same embodiment of FIG. 53-55, wherein the actuation member is inserted distally into the first housing, causing the expandable cannula device to become expanded;

FIG. 57 is a side view of example embodiment shown in FIG. 56;

FIG. 58 is a cross-sectional view of example embodiment shown in FIG. 57;

FIG. 59 is an isometric view of the expanded configuration of the device of FIGS. 56-58 further comprising an insertable member inserted into the expanded passage of the cannula, and an obturator inserted into the lumen of the insertable member;

FIG. 60 is a cross-sectional side view of example embodiment shown in FIG. 59;

FIG. 61 is an isometric view of the device of FIGS. 59-60, wherein the obturator is removed from the lumen of the insertable member;

FIG. 62 is a cross-sectional side view of the example embodiment shown in

FIG. 61;

FIG. 104 is an isometric view of an example embodiment of an obturator inserted into the lumen of an insertable member FIG. 105 is a cross-sectional side view of the example embodiment of FIG. 103

FIG. 106 is an isometric view of a short insertable member, as depicted in example embodiments in FIGS. 104-105;

FIG. 119 is an isometric view of an example embodiment of an expanded expandable cannula device with an insertable member being threadedly coupled to an obturator, and inserted into the expanded passage of the device;

FIG. 120 is a cross-sectional side view of the embodiment shown in FIG. 119;

FIG. 121 is a cross-sectional side view of the embodiment shown in FIG. 120, with the obturator being removed from the lumen of the insertable member;

FIG. 122 is an isometric view of the embodiment of the expandable cannula device shown in FIG. 121;

FIG. 125 is a side view of an example embodiment of an expanded expandable cannula device with the same embodiment of the insertable member as shown in FIGS. 123-124 being inserted into its expanded passage;

FIG. 126 is an isometric view of the same example embodiment shown in FIG. 125;

FIG. 127 is an isometric view of an example embodiment of an insertable member or an actuation member;

FIG. 128 is a cross-sectional side view of the example embodiment shown in FIG. 127;

FIG. 129 is an isometric view of an example embodiment of an insertable member or an actuation member, like the embodiments shown in FIG. 127-128, however with threaded features on its external surface;

FIG. 130 is a cross-sectional side view of the example embodiment shown in FIG. 129;

Figure 110:
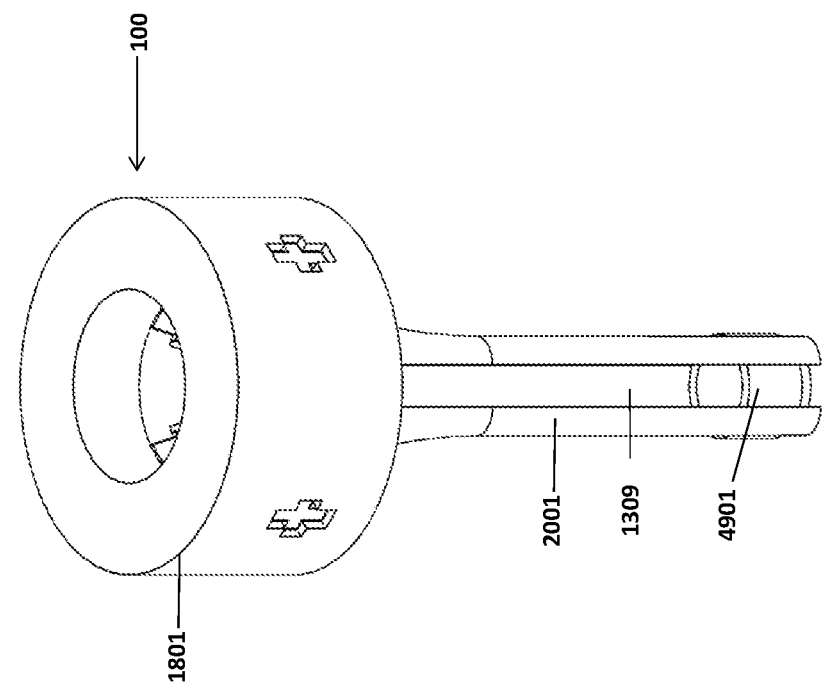
FIG. 110 is an isometric view of the same embodiment of expanded cannula device depicted in FIG. 109, however with the obturator removed from the lumen of the insertable member, and the expanded passage of the expandable cannula device embodiment.
Figure 135:
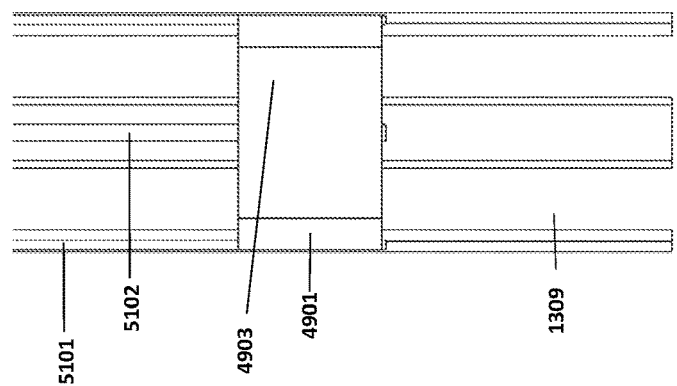
Figure 133:
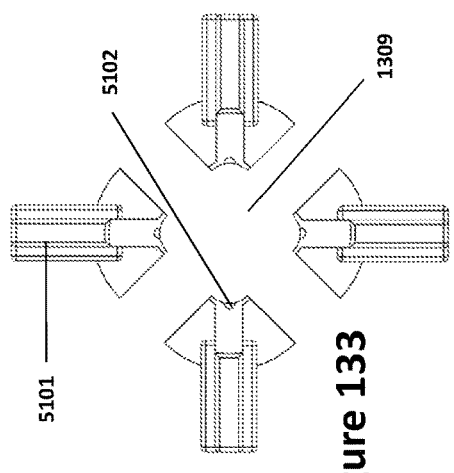
Figure 134:
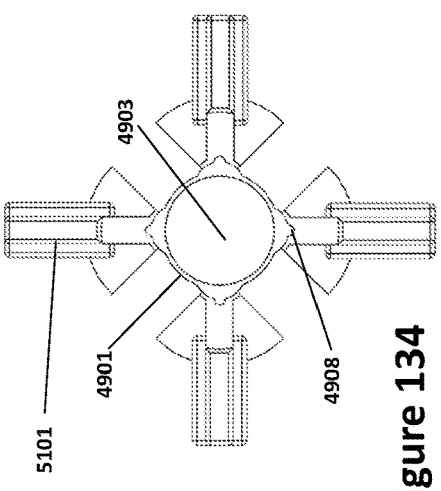
Figure 132:
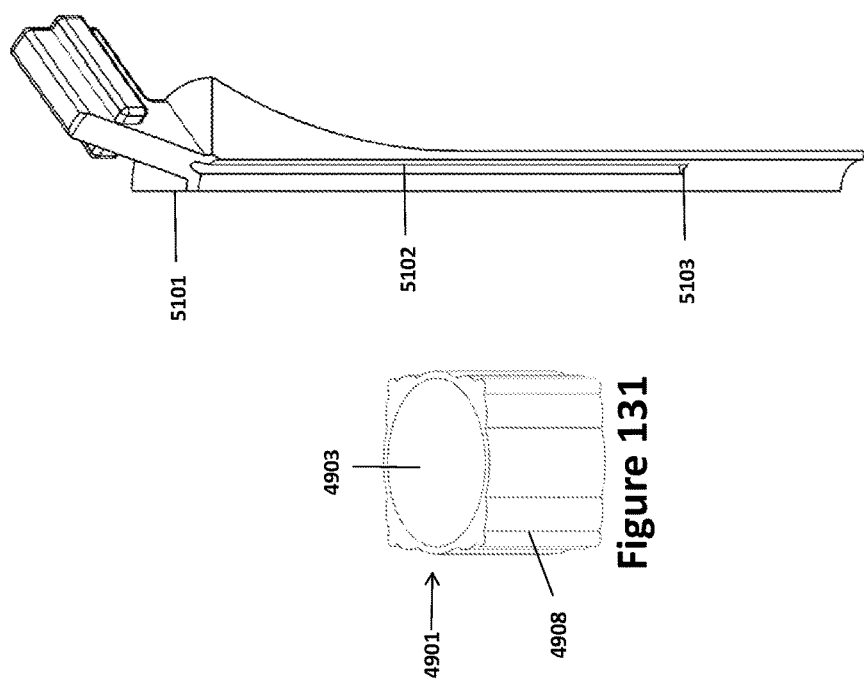
Figure 131:
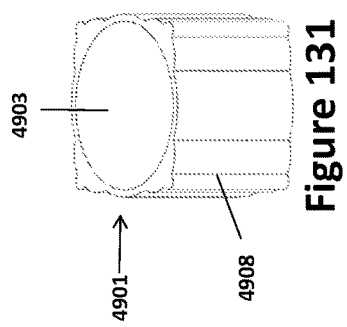
Figure 136:
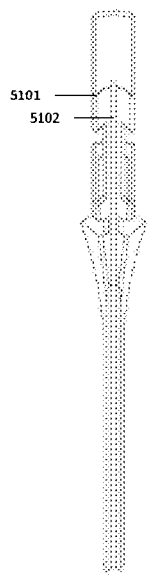
Figure 137:
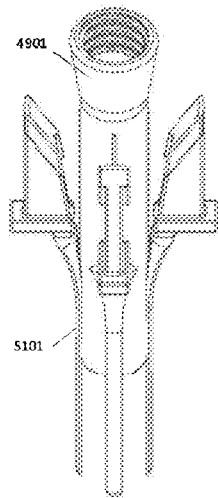
Figure 138:
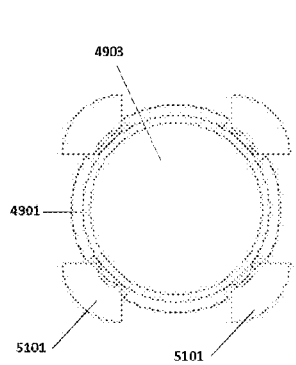
Figure 139:
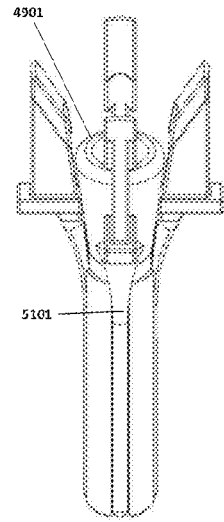
Figure 140:
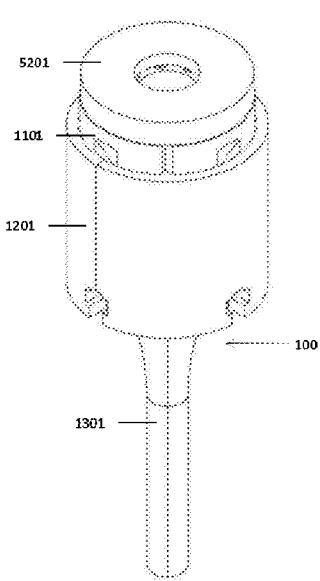
Figure 141:
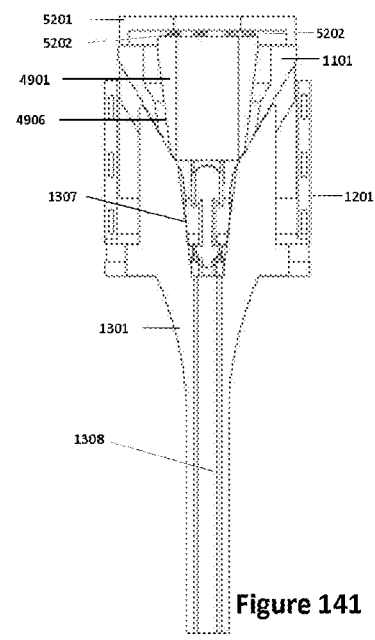
Figure 142:
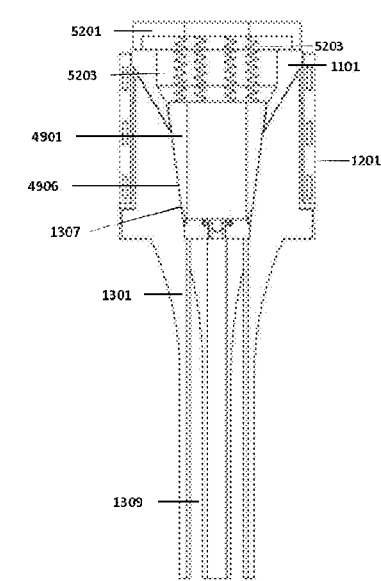
Figure 151:
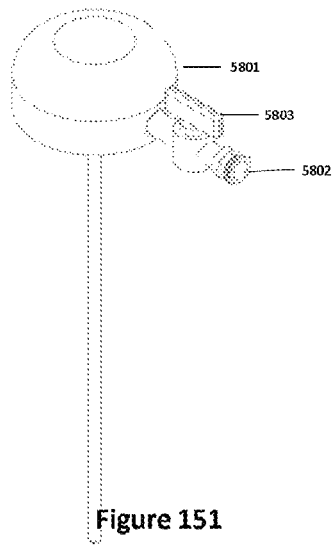
Figure 152:
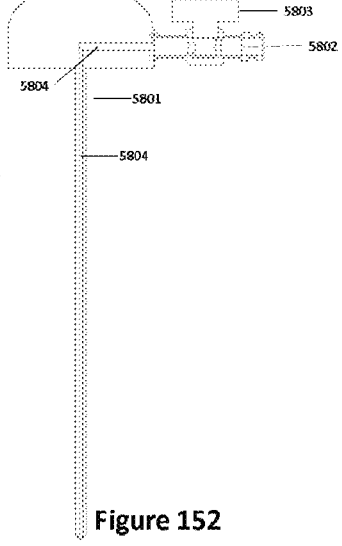
Figure 153:
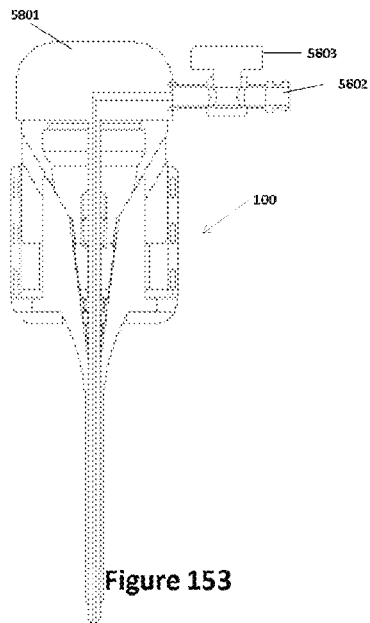
Figure 154:
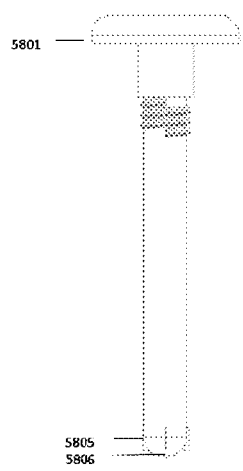
Figure 155:
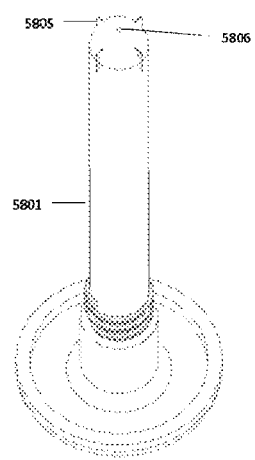
Figure 171:
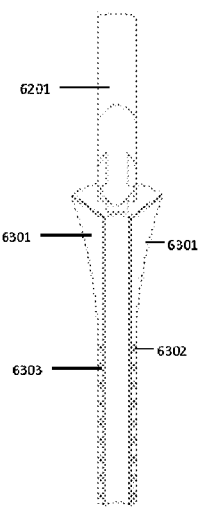
Figure 172:
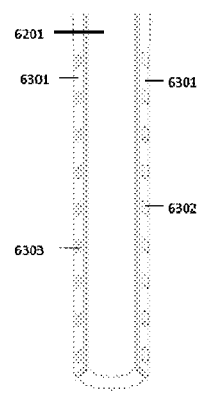
Figure 173:
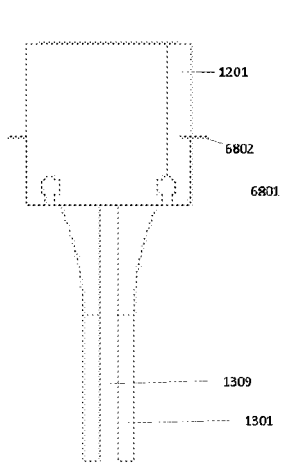
Figure 174:
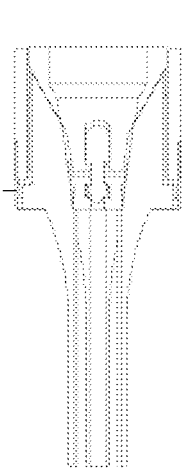
Figure 175:
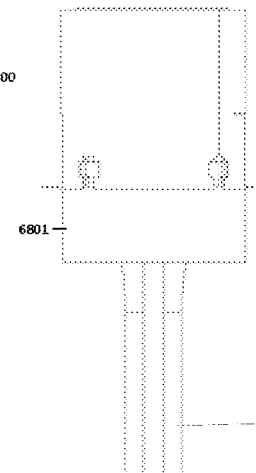
Figure 176:
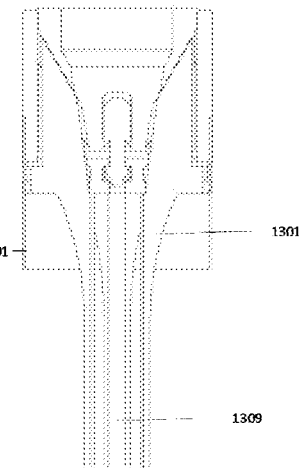
Figure 177:
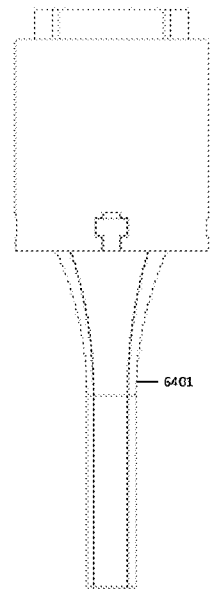
Figure 178:
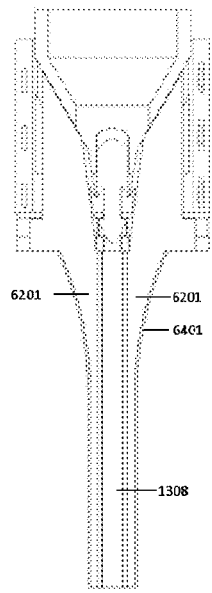
Figure 179:
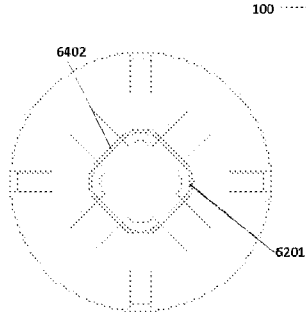
Figure 180:
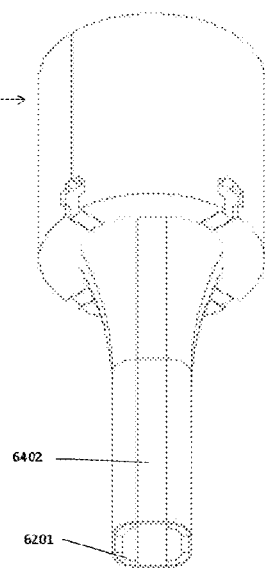
Figure 181:
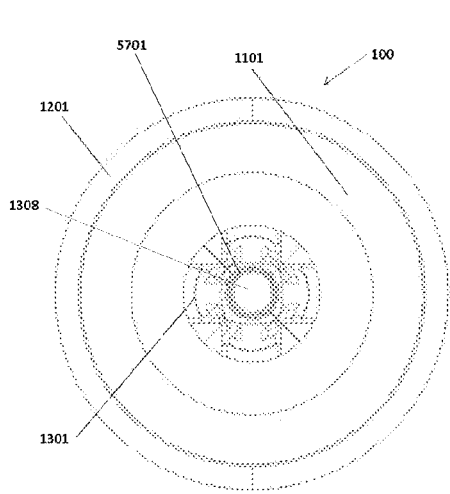
Figure 182:
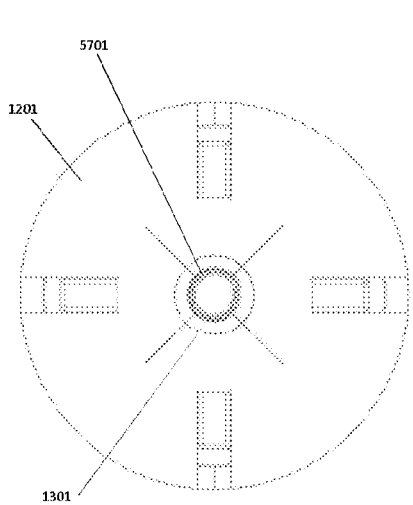
Figure 183:
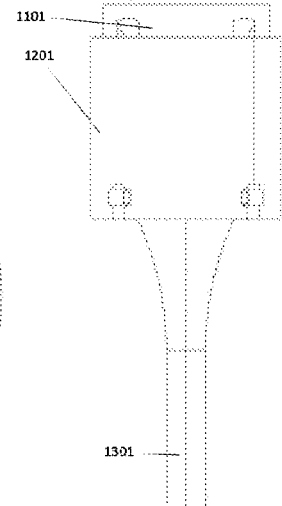
Figure 191:
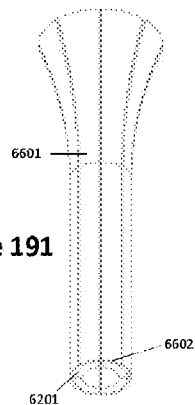
Figure 193:
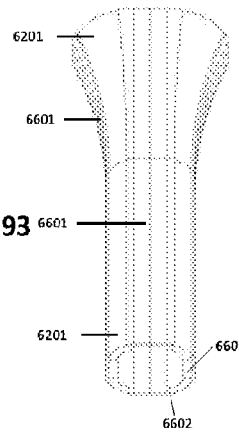
Figure 192:
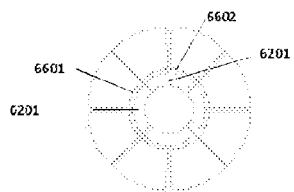
Figure 194:
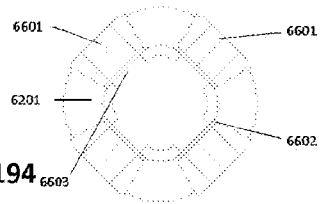
Figure 195:
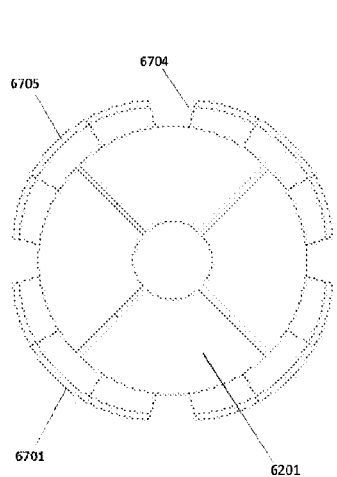
Figure 196:
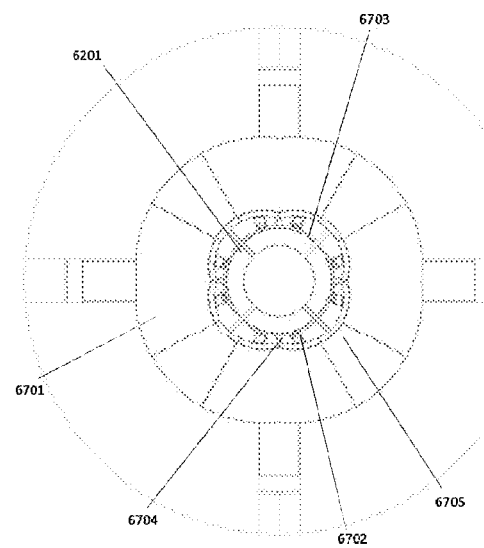
Figure 197:
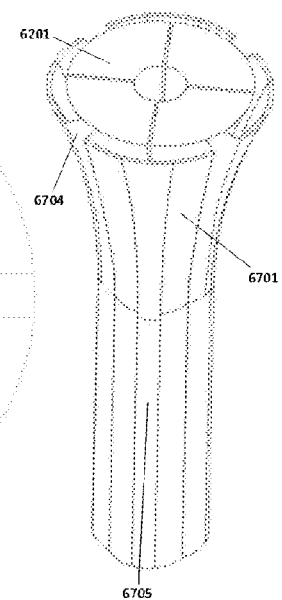
Figure 198:
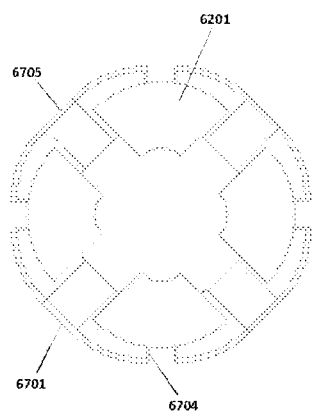
Figure 199:
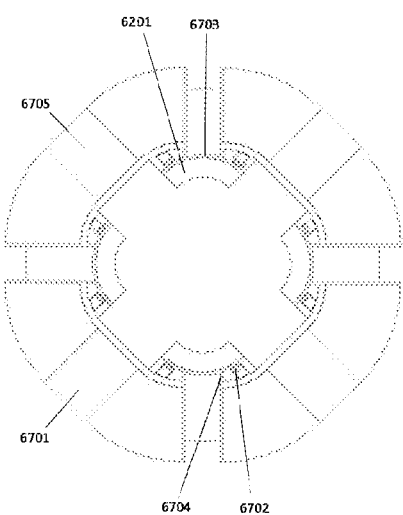
Figure 200:
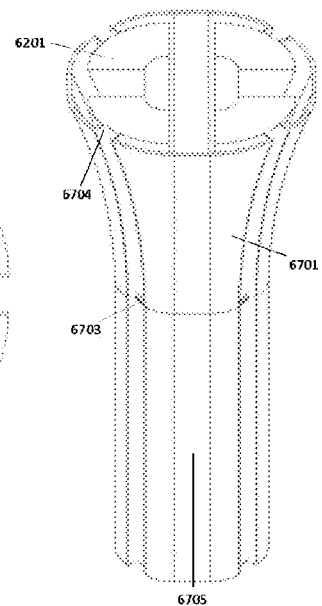
Figure 201:
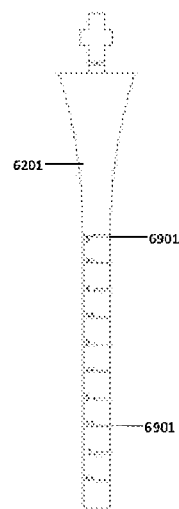
Figure 202:
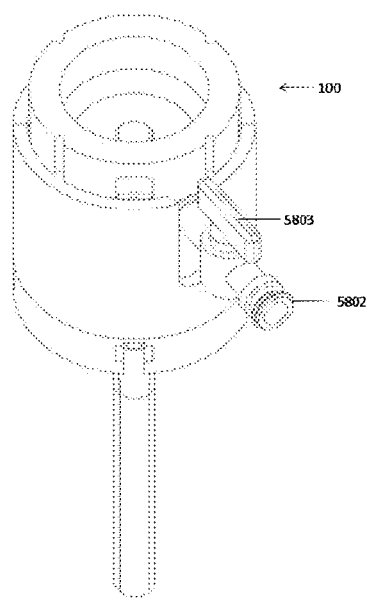
Figure 203:
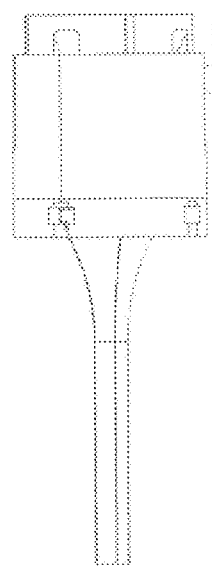
Figure 204:
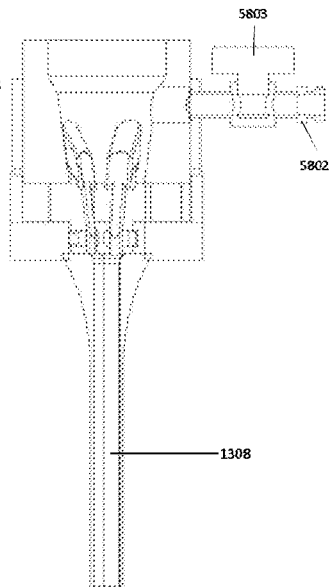
Figure 205:
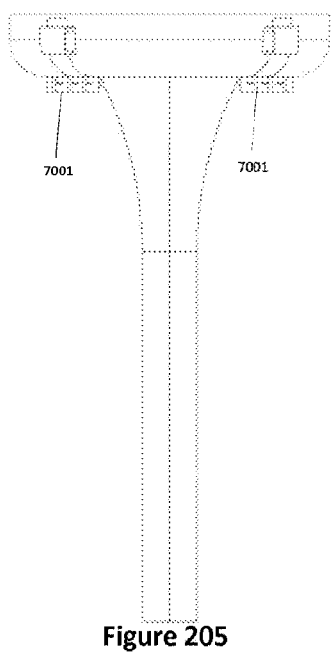
Figure 206:
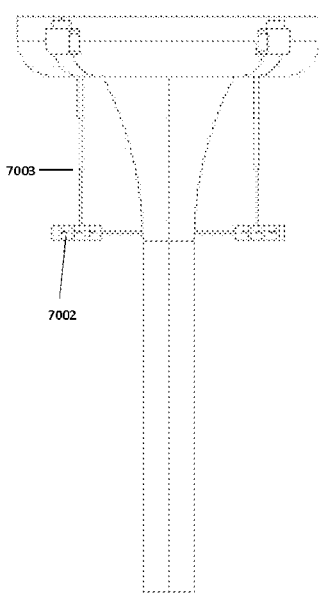
Figure 207:
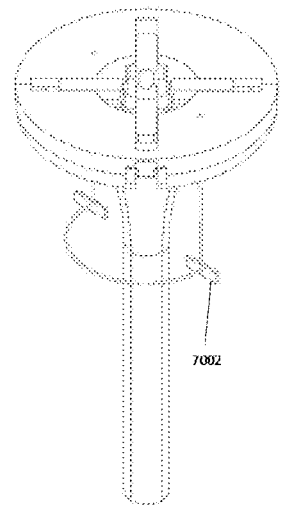
Figure 208:
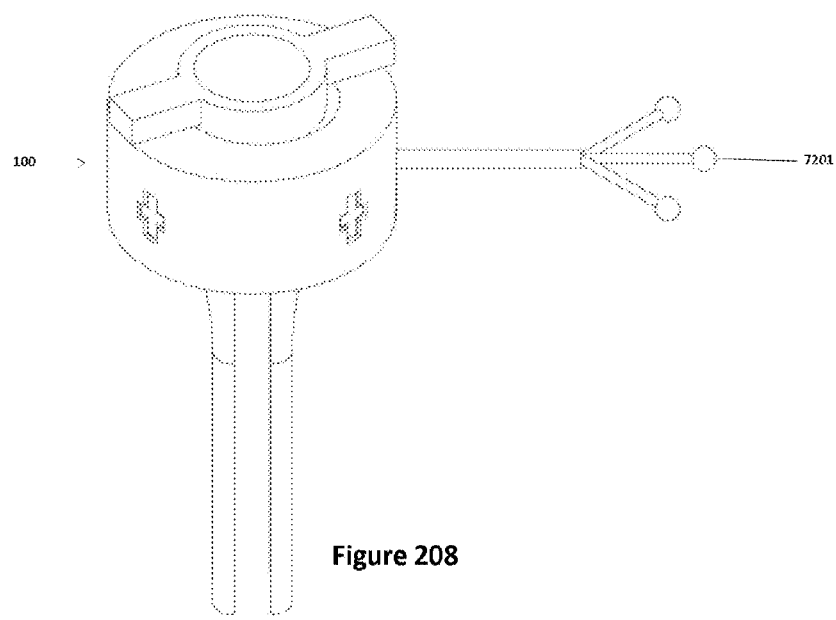
Figure 209:
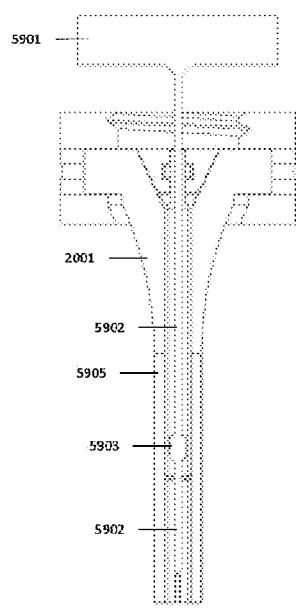
Figure 210:
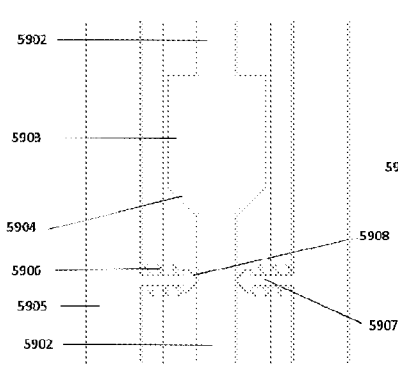
Figure 211:
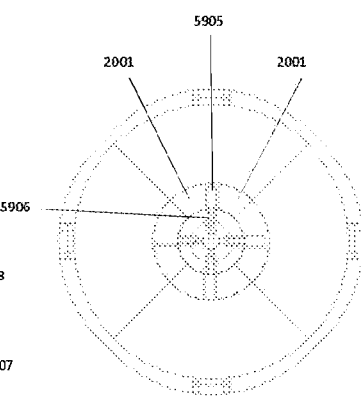
Figure 212:
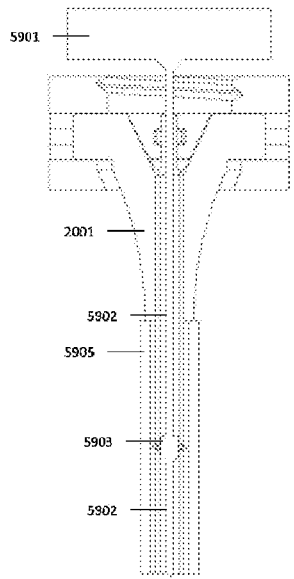
Figure 213:
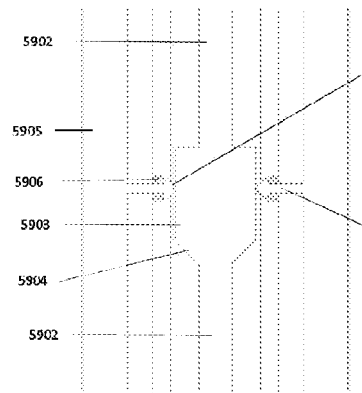
Figure 214:
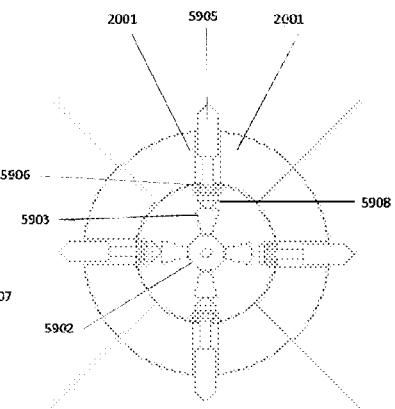
Figure 215:
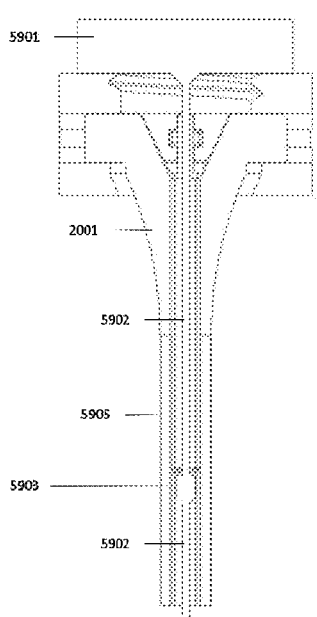
Figure 216:
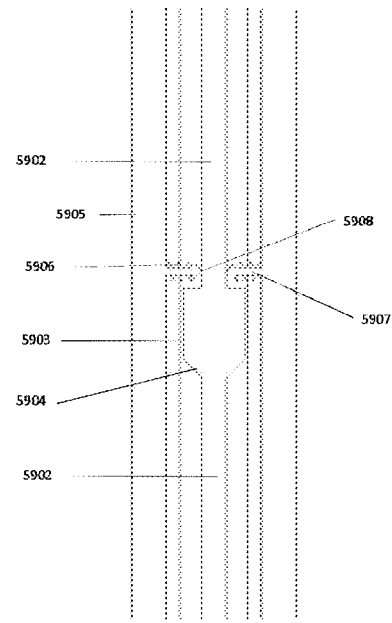
Figure 217:
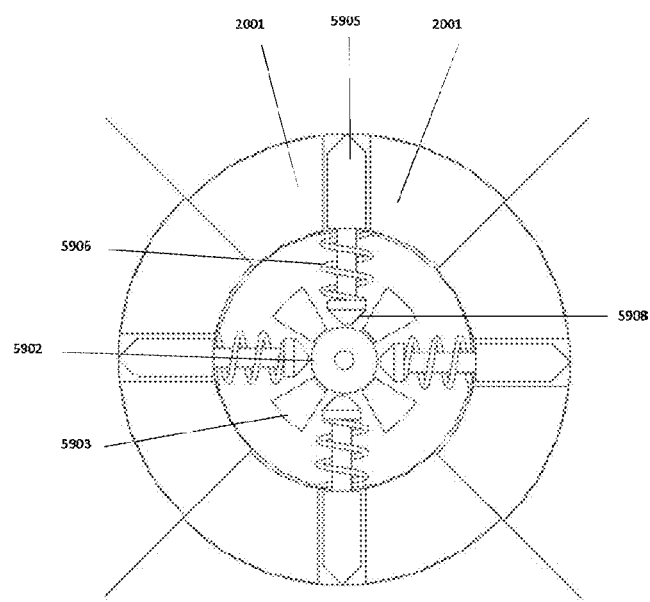

FIG. 131 is an isometric view of an example embodiment of an insertable member with features on its external surface FIG. 132 is an isometric view of an example embodiment of an elongate rigid member with a groove in its internal surface FIG. 133 is a top view of an example embodiment of the plurality of elongate rigid members as shown in FIG. 132, comprising an expanded passage of an expandable cannula device (rest of expandable cannula device components not shown);

FIG. 134 is a top view of the embodiment shown in FIG. 133, with the embodiment of the insertable member shown in FIG. 131 being inserted into the passage defined by the plurality of elongate rigid member, such that the features of the insertable member fit into the grooves of the elongate rigid members;

FIG. 135 is a cross-sectional side view of the example embodiment of FIG. 134;

FIG. 136 is a front view of an example embodiment of an elongate rigid member with a groove on its internal surface;

FIG. 137 is an isometric view of an example embodiment of an expanded expandable cannula device (not shown), comprising a plurality of example embodiments of elongate rigid members as shown in FIG. 136, where an insertable member comprising external tongue features is inserted into the expanded passage of the device, such that the tongues are complimentary to the grooves of the plurality of elongate rigid members;

FIG. 138 is a bottom view of an example embodiment of an insertable member being inserted into the expanded passage of an expanded expandable cannula embodiment, wherein the external surface of the insertable member comprises a plurality of grooves, that are complimentary to the example embodiments of the plurality of elongate rigid members;

FIG. 139 is an isometric view of the example embodiment shown in FIG. 138 (other expandable cannula device components not shown);

FIG. 140 is an isometric view of an example embodiment of an expandable cannula device, in an unexpanded state, with a member attached to the first housing, and a biased insertable member (not visible);

FIG. 141 is a cross-sectional side view of the expandable cannula device embodiment shown in FIG. 140, further illustrating the relationship between the insertable member, plurality of biasing members, and the plurality of elongate rigid members;

FIG. 142 is a cross-sectional side of the expandable cannula device shown in FIGS. 140-141, wherein the device is expanded by moving the second housing closer to the first housing, and the biasing members propelling the insertable member into the expanded passage;

FIG. 143 is a cross-sectional side view of an example embodiment of an expandable cannula device, at an expanded state, with insertable member comprising an axially contracted flexible sealing member, disposed in a region proximal to the plurality of expanded elongate rigid members;

FIG. 144 is a cross-sectional side view of the example embodiment shown in FIG. 143, with the insertable member being inserted further into a distal region of the expanded passage comprised by the plurality of elongate rigid members, where the flexible sealing member becomes axially expanded;

FIG. 145 is a side view of the expandable cannula device embodiment shown in FIG. 144;

FIG. 146 is an isometric view of the device embodiment of FIGS. 144-145;

FIG. 147 is a cross-sectional side view illustrating an example of plurality of elongate rigid members comprising a plurality of non-smooth features movable within the walls of the elongate rigid members;

FIG. 148 is a cross-sectional side view of the embodiment device shown in FIG. 147, wherein an insertable member and an obturator being inserted into the passage formed by the elongate rigid members, causes the non-smooth features to protrude out of the walls;

FIG. 149 is a close-up of a section of FIG. 148;

FIG. 150 is a cross-sectional side view of the embodiment device shown in FIGS. 147-149, wherein the insertable member and the obturator are inserted fully into the passage, and all the non-smooth features are ejected;

FIG. 151 is an isometric view of an example obturator comprising an insufflation port;

FIG. 152 is a cross-sectional side view of the obturator embodiment shown in FIG. 151;

FIG. 153 is a cross-sectional side view of the obturator example of FIGS. 151-152 being inserted into an unexpanded passage of an example embodiment of an expandable cannula device;

FIG. 154 is a side view of an example embodiment of an obturator with a plurality of blades disposed near the distal tip of the obturator FIG. 155 is an isometric bottom view of the example embodiment shown in FIG. 154;

FIG. 156 is a front view of an example embodiment of an elongate rigid member with a fluid channel disposed along the inner surface of the elongate rigid member;

FIG. 157 is an isometric view of the example embodiments of elongate rigid members shown in FIG. 156 comprising an unexpanded passage of an expandable cannula device (not shown), with an example embodiment of an obturator comprising a hollow portion;

FIG. 158 is a cross-sectional side view of the example embodiment shown in FIG. 157;

FIG. 159 is a bottom view of the example embodiments shown in FIGS. 157-158;

FIG. 160 is a bottom view of the example embodiment of the elongate rigid member shown in FIG. 156;

FIG. 161 is a cross-sectional side view of another example embodiment of the obturator shown in FIGS. 157-158, wherein the obturator comprises channels that connect the hollow portion to openings in the tip of the obturator;

FIG. 162 is an isometric view showing a cross-sectional side view of the example embodiments of FIG. 161;

FIG. 163 is a bottom view of the example embodiments shown in FIGS. 161-162;

FIG. 164 is an isometric view of an example embodiment of an expandable cannula device comprising a one-way fluid valve;

FIG. 165 is a cross-sectional side view of the example embodiment shown in FIG. 164;

FIG. 166 is a close-up view of the proximal region of the example embodiment shown in FIG. 165;

FIG. 167 is a top view of an example embodiment of an adjustable valve, comprising a small inner diameter;

FIG. 168 is an isometric view of the example embodiment shown in FIG. 167;

FIG. 169 is a top view of the example embodiment of the adjustable valve shown in FIGS. 167-168, however configured to comprise a larger inner diameter;

FIG. 170 is an isometric view of the example embodiment shown in FIG. 169;

FIG. 171 is an isometric view of an example embodiment of an elongate rigid member comprising gaskets on its side surfaces;

FIG. 172 is a front close-up view of a distal region of the example embodiment of an elongate rigid member shown in FIG. 171;

FIG. 173 is a side view of an example embodiment of an expandable cannula device, at an expanded state, with a telescoping gasket built into the second housing of said device and configured in a retracted position;

FIG. 174 is a cross-sectional side view of the example embodiment shown in FIG. 173;

FIG. 175 is a side view of the example embodiment shown in FIGS. 173-174, with the telescoping gasket configured in an expanded state;

FIG. 176 is a cross-sectional view of the embodiment shown in FIG. 175;

FIG. 177 is a side view of an example embodiment of an expandable cannula device, at an unexpanded state, with an expandable sleeve disposed on the outer surface of the plurality of elongate rigid members;

FIG. 178 is a cross-sectional view of the embodiment shown in FIG. 177;

FIG. 179 is a bottom view of the expanded configuration of the example expandable cannula device embodiment shown in FIGS. 177-178, wherein the expandable sleeve is expanded and sealing the gaps between the expanded elongate rigid members;

FIG. 180 is an isometric view of the example embodiment shown in FIG. 179;

FIG. 181 is a top view of an expandable cannula device embodiment comprising a coiled sheet member disposed in the unexpanded passage of the expandable cannula device;

FIG. 182 is a bottom view of the expandable cannula device embodiment shown in FIG. 181;

FIG. 183 is a side view of the expandable cannula device shown in FIGS. 181-182;

FIG. 184 is a bottom view of the expanded configuration of the example embodiment of the expandable cannula device shown in FIGS. 181-183, where the coiled sheet becomes uncoiled in the expanded passage defined by the plurality of elongate rigid members;

FIG. 185 is a top view of the example embodiment shown in FIG. 184;

FIG. 186 is an isometric view of the example embodiments shown in FIGS. 184-185;

FIG. 187 is an isometric view of an example embodiment of unexpanded passage of an expandable cannula device (not shown) comprising contracted sleeves in between each pair of elongate rigid members;

FIG. 188 is a close-up bottom view of the example embodiment shown in FIG. 188;

FIG. 189 is an isometric view of the expanded passage of the example embodiment of an expandable cannula device, wherein the sleeves in between each pair of elongate rigid members are expanded;

FIG. 190 is a close-up bottom view of the example embodiment shown in FIG. 189;

FIG. 191 is an isometric view of an example embodiment of a magnetic sleeved disposed on the outer surface of each adjacent pair of the plurality of elongate rigid members comprising an unexpanded passage of an expandable cannula device (not shown);

FIG. 192 is a bottom view of the example embodiment shown in FIG. 191;

FIG. 193 is an isometric view of the example embodiments shown in FIGS. 191-192, wherein each of the magnetic sleeves covers the gap in between each adjacent pair of the expanded elongate rigid members;

FIG. 194 is a bottom view of the example embodiment shown in FIG. 193;

FIG. 195 is a cross-sectional top view of an unexpanded passage of an expandable cannula device (not shown) comprised by a plurality of elongate rigid members, with a sliding sleeve disposed on the outer surface of each pair of adjacent elongate rigid members;

FIG. 196 is a bottom view of the example embodiment shown in FIG. 195;

FIG. 197 is an isometric view of the example embodiments shown in FIGS. 195-196, wherein the proximal part of the expandable cannula device is hidden;

FIG. 198 is a cross-sectional top view of the expanded passage of the example embodiment of an expandable cannula device shown in FIGS. 195-197, wherein the sliding sleeves cover the gaps in-between the expanded elongate rigid members;

FIG. 199 is a bottom view of the example embodiment shown in FIG. 198;

FIG. 200 is an isometric of the example embodiments shown in FIGS. 198-199, wherein the proximal part of the expandable cannula device is hidden;

FIG. 201 is a back view of an example embodiment of an elongate rigid member with insertion depth graduated markers;

FIG. 202 is an isometric view of an example embodiment of an expandable cannula device comprising an insufflation port;

FIG. 203 is a side view of the example embodiment shown in FIG. 202;

FIG. 204 is a cross-sectional view of the example embodiment of FIG. 203;

FIG. 205 is a side view of a distal region of an example embodiment of an expandable cannula device comprising an incision cutting guide at an unexpanded state;

FIG. 206 is a side view of the example embodiment shown in FIG. 205 where the incision making guide is expanded;

FIG. 207 is an isometric view of the example embodiment shown in FIG. 206;

FIG. 208 is an isometric view of an example embodiment of an expandable cannula device with a plurality of live position tracking features;

FIG. 209 is a cross-sectional side view of an example embodiment of an expandable cannula device configured with movable blades embedded in the walls of elongate rigid members, and an example embodiment of an obturator with an enlarged portion configured for moving the blades out when the enlarged portion is aligned with the spine that is connected to the inner side of each blade;

FIG. 210 is close-up view of the expansion mechanism embodiment of the blades, where the blades are not expanded out of the elongate rigid members walls;

FIG. 211 is a bottom view of the example embodiments of FIGS. 209-110;

FIG. 212 is a cross-sectional side view of the example embodiment shown in FIGS. 209-211, with the enlarged portion of the obturator is aligned with the spine of the blades, such that the blades are pushed out of the walls of the elongate rigid members;

FIG. 213 is a close-up view of the example embodiment depicted in FIG. 212;

FIG. 214 is a bottom view of the example embodiment shown in FIG. 212-213;

FIG. 215 is a cross-sectional side view of the example embodiment shown in FIGS. 212-214, where the enlarged portion of the obturator is in a position more distal to the spines of the blades and is no longer aligned with the spines, such that the blades are retracted in the walls of the elongate rigid members again;

FIG. 216 is a close-up view of the example embodiment shown in FIG. 215; and FIG. 217 is a bottom view of the example embodiments shown in FIGS. 215-216, wherein the obturator is rotated, such that its enlarged portions are no longer aligned with the spines of the blades, and the obturator may be retracted from the passage of the expandable cannula device without causing an additional expansion of the blades.

DETAILED DESCRIPTION OF EXAMPLE EMBODIMENTS

In example embodiments, there is provided the enlargement of the diameter of a port size via an expandable cannula device.

With reference to FIGS. 1-9, in an example embodiment, a cannula device 100 is illustrated. Examples of the cannula device 100 can be implemented in trocars, in example embodiments.

Figure 1:
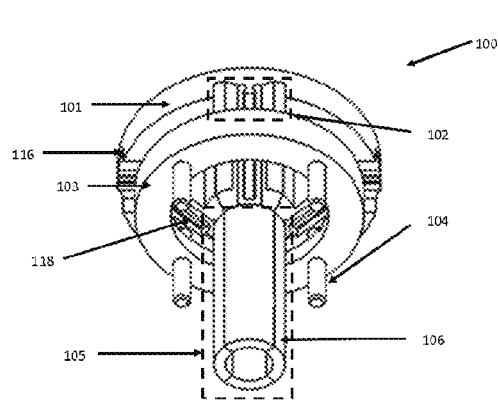
FIG. 1 is an isomeric view of an example expandable cannula device in an unexpanded state, having a push to expand capability.
Figure 2:
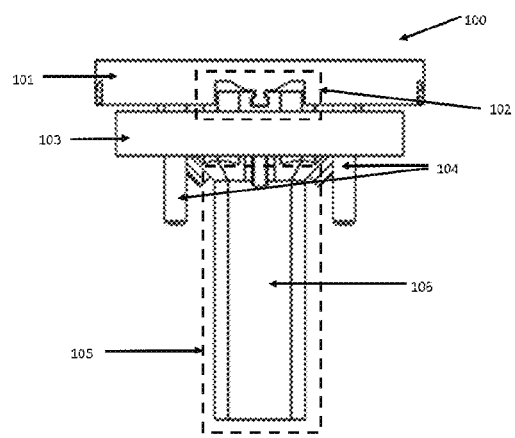
FIG. 2 is a side view of the example expandable cannula device shown in FIG. 1.
Figure 3:
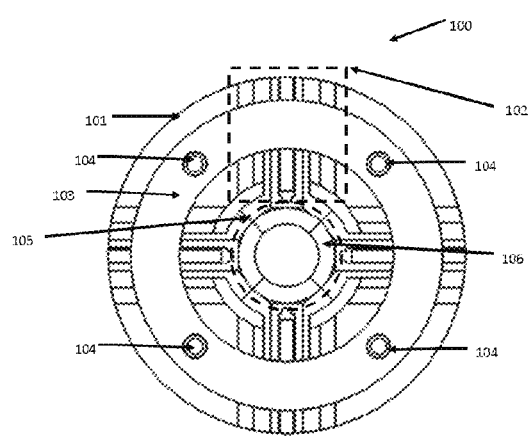
FIG. 3 is a bottom view of the example expandable cannula device of FIGS. 1-2.
Figure 4:
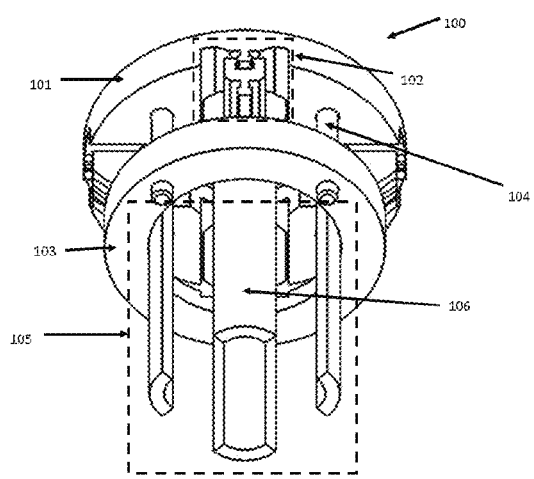
FIG. 4 is an isomeric view of the example expandable cannula device of FIGS. 1-3 in an expandable state.
Figure 5:
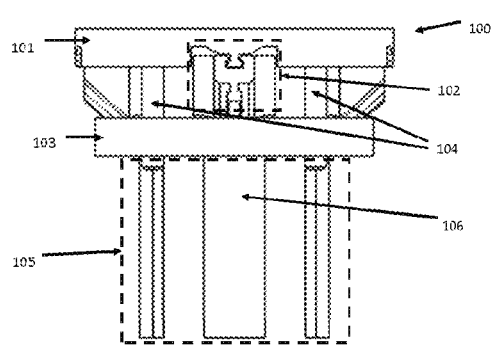
FIG. 5 is a side view of the example expandable cannula device of FIGS. 1-4 in the expandable state.
Figure 6:
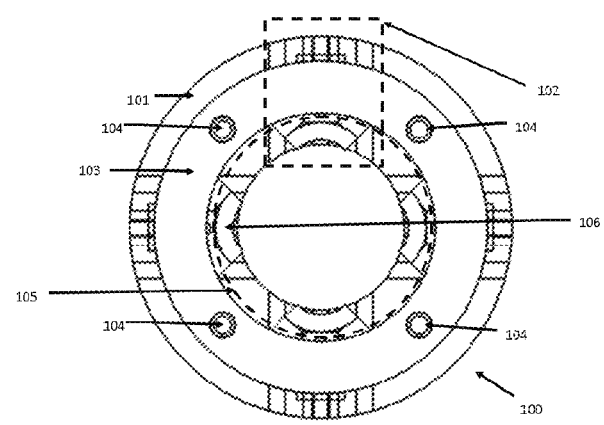
FIG. 6 is a bottom view of the example expandable cannula device of FIGS. 1-5 in the expandable state.
Figure 7:
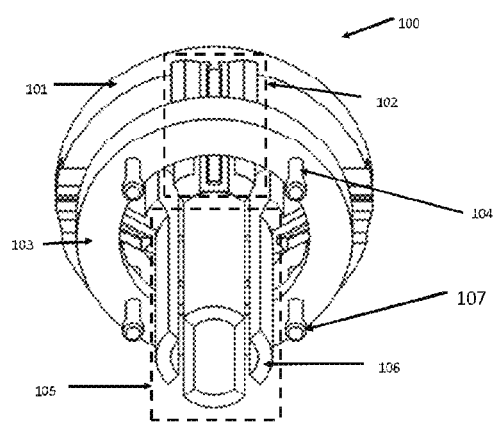
FIG. 7 is an isomeric view of an alternative embodiment of an example expandable cannula device with guiding members having a larger end.
Figure 8:
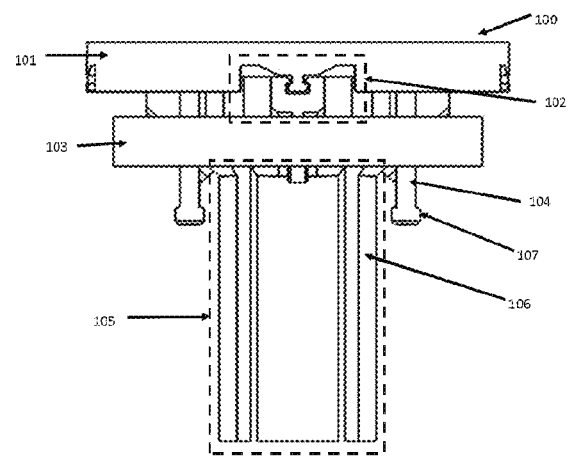
FIG. 8 is a side view of the example expandable cannula device of FIG. 7.

The cannula device 100 has a head or a first ring 101 that may be detachably attachable to the rest of the cannula 100 and a plurality of radially expanding rigid members 106 that, for example, form a substantially circular internal diameter shape when at the unexpanded state, see FIG. 1. In some examples, the rigid members 106 are coated with a polymeric material that reduces friction between the rigid members 106 and instruments that are inserted through the lumen of the cannula device 100. In some examples, the coating is made of parylene.

The initial unexpanded internal diameter formed by the elongate rigid members 106 may be 3 mm or 5 mm (examples of standard sizes of small trocars); or may have different diameters in other example embodiments.

The final (expanded) internal diameter or aperture created by elongate rigid members 106 when they are expanded by a second ring 103, which can be referred to as an "expansion ring", and which may be 8 mm, 10 mm, 12 mm, or 15 mm (examples of standard sizes of large trocars); or may have different diameters in other example embodiments.

The second ring 103 may not be rotatable with respect to the first ring 101 in example embodiments.

In some examples, one or more of the elongate rigid members 106 have one or more blades or serrations.

In some examples there may be three rigid members 106 that define a circular aperture, and in other examples there may be four rigid members 106 that define a circular aperture. There may also be fewer than three and more than four rigid members 106, in other example embodiments. Further, the expanding rigid members may form a substantially rectangular or square shape or another kind of shape, in other example embodiments.

In some examples, the rigid members 106, also known as "sliders", that use a first respective track 116 that slide along the head 101 of the cannula 100. Each first respective track 116 is on the first ring 101, one for each rigid member 106. The rigid members 106 are coupled to a second ring 103 (sometimes referred to as an expansion ring), which forms a linear cam 102 for each rigid member 106. The second ring 103 may set the position of the rigid members 106 substantially in unison using a second respective track 118 on each of the rigid members 106 that extends axially outward and diagonally with respect to a central axis defined by the center of the first ring 101. The second ring 103 may be attachably detachable to the rest of the cannula 100.

In some examples, a second ring 103 is slidable in an axial direction with respect to the first ring 101, the second ring 103 being operably connected to the elongate rigid members 106 so that sliding of the second ring 103 with respect to the first ring 101 causes the plurality of elongate rigid members 106 to move away from each other and increase a size of the internal diameter or aperture.

It can be appreciated that the reference to a "track" can be a reference to inter-engaging parts that are slidable with respect to each other, for example tongue-and-groove, and other such systems. Reference to a track being located on one component can refer to either the tongue or the groove, that engages another component that has the other of the tongue or the groove.

In some examples there is an expandable sealing gasket or housing between the first ring 101 and the second ring 103. The sealing gasket or housing may be made of a polymer or rubber material.

In some examples, the first ring 101 and the second ring 103 are co-axial. In some examples, the inner diameter of the first ring 101 is larger than the inner diameter of the second ring 103. In some examples, the first ring 101 is larger than the second ring 103.

The radial position of the rigid members 106 is determined by the vertical position of the second ring 103. This can be actuated as either push, examples in FIGS. 1-6, or pull mechanism, examples in FIGS. 20-26; depending on the design of the cam, sliding members and the bottom ring, and can be reversed in design for other example embodiments, as would be appreciated by those skilled in the art.

In an example embodiment, the second ring 103 is kept axially centered by a plurality of guiding pins 104 (or guiding members) that axially extend from the first ring 101, that ensure the rigid members 106 always move together radially and to minimize jamming during a transition from a non-expanded position to an expanded position.

In a further example embodiment, a combination of: either the internal diameter of the second ring 103 or the radial location of the guiding pins 104, or both features, can be used as methods to dictate the maximum internal diameter of the rigid members 106 when the rigid members 106 expand.

The guiding pins 104 may also contain some features such as an enlarged ending 107, or a removable clip (not shown) or an adjustable threaded nut (not shown) that limit or control the expansion dictated by the second ring 103.

The second ring 103 that has an inner diameter that matches the outer diameter of cannula 105 at the expanded state, such that the second ring 103 is in direct contact with the rigid members 106. Such contact of second ring 103 with the rigid members 106 provides an anchor point that is lower than the first ring 101, which reduces the moment arm length of the rigid members 106 or reduces vertical motion caused by pneumoperitoneum, or compressive tissue stresses on the rigid members 106. This reduces the overall moment generated by pneumoperitoneum, or compressive tissue stresses and thus reduces the deflection of distal ends of the rigid members 106 when the device 100 is in tissue or skin.

A balloon (not shown) may be positioned along the circumference of the internal diameter of the rigid members 106 when the balloon is deflated. The balloon in the deflated form grants space for instrument access via the lumen of the cannula 105. The balloon may be inflated via fluid (such as saline, water or gas, etc.) such that it expands to a specific size and applies pressure onto the rigid members 106 to move radially out. Once expansion of rigid members 106 is performed, the fluid can be drained/deflated from the balloon such that access is permitted via the lumen of the cannula device 100.

The balloon may be made of a material such as PEBAX or other suitable material that is relatively difficult to stretch and may have a modulus of elasticity in the range of 10-2000 MPa. The balloon may be further configured for drainage or deflation to allow access of instruments via the lumen of the cannula device 100.

Figure 9:
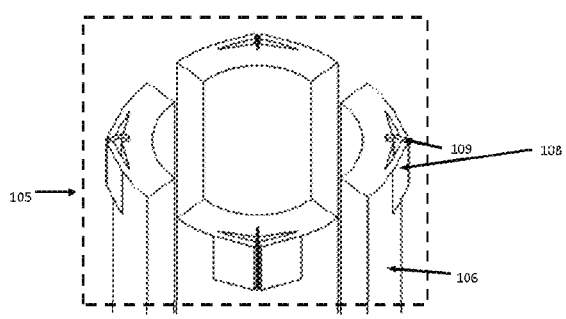
FIG. 9 is a portion of rigid members in the cannula of FIGS. 1-8 showing a portion containing hidden blades exposed when the rigid members expand.
Figure 10:
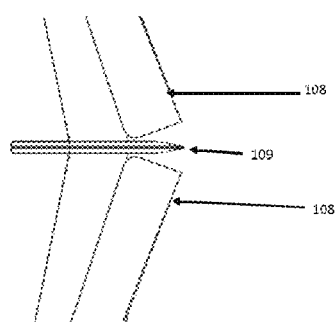
FIG. 10 is a cross-sectional view of the portion containing the blade in the rigid member shown in FIG. 9.
Figure 11:
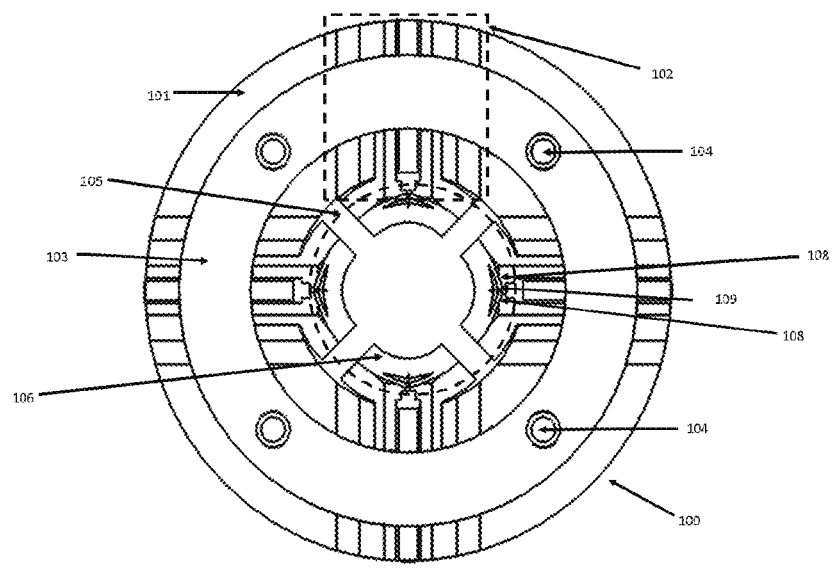
FIG. 11 is a bottom view of the example embodiment of FIGS. 9-10.

In a further example embodiment, referring to FIGS. 9-11, the rigid members 106 contain one or more blades 109 that are directed radially outwards in some part of the long axis. This blade 109 is covered by shields/leaflets 108 that may be mechanically coupled to the second ring 103 and hence mechanically unravel to expose the blade features 109. The leaflets 108 may be unraveled by tissue forces that oppose expansion. The leaflets 108 cover the blade again when expansion with the second ring 103 is stopped.

In an alternate embodiment, the blade 109 can move out of the rigid members 106 while the second ring 103 is activated.

In some examples there is provided a guide for creating a larger incision on the skin by a scalpel or energy cutting device.

Several methods of locking the rigid members 106 at the initial smallest internal diameter will now be described.

Figure 12:
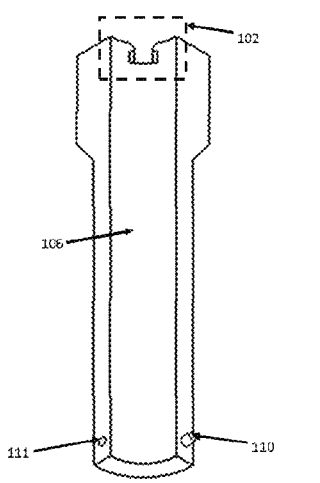
FIG. 12 is an isomeric view of a rigid member containing a peg for insertion into an adjacent rigid member at the unexpanded state, and containing a cavity for another peg to be inserted through it from an adjacent rigid member.
Figure 13:
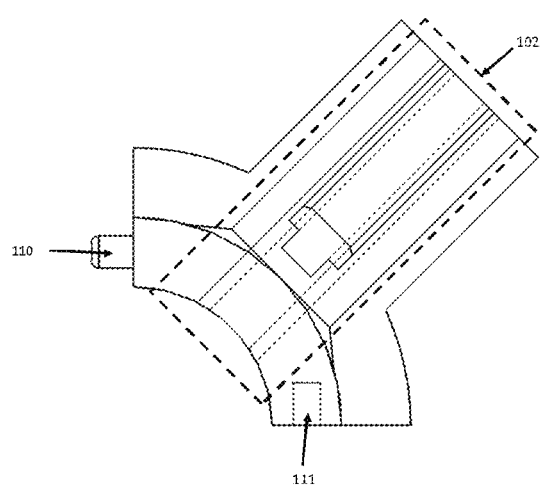
FIG. 13 is a bottom view of FIG. 12.

In an example embodiment, the rigid members 106 are kept locked at the small inner diameter setting via pegs 110 that penetrate the neighboring rigid members 106 in a perpendicular direction to the long axis of the rigid members 106 and fit within a complimentary cavity 111 (See FIGS. 12-13).

FIG. 1 illustrates an isometric view of a rigid member containing a peg for insertion into the adjacent rigid member at the unexpanded state. It also shows a cavity 111 for another peg to be inserted through it from an adjacent rigid member.

In another embodiment, mechanical latches (not shown) can be activated between the second ring 103 and top piece of the first ring 101 or between the second ring 103 and the rigid members 106 such that unintended movement of second ring 103 is limited or prevented unless the one or more latches are released.

In another embodiment, there are mechanical barriers (not shown) between the guiding pins 104 and the second ring 103 that must be removed to allow for ring movement, and thus expansion.

Figure 14:
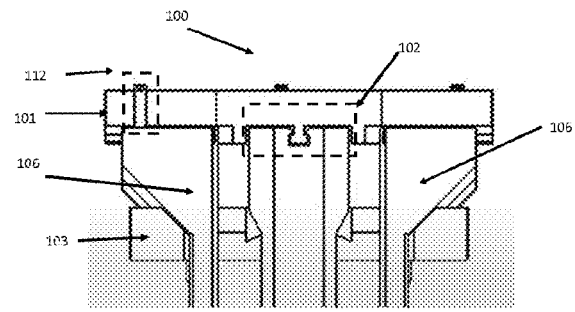
FIG. 14 is side view of an example embodiment of the cannula device of FIG. 1 with a set screw mechanism for preventing elongate rigid members from moving any further by either forming a physical barrier of moving any further out or by applying downwards pressure on them to prevent motion.
Figure 15:
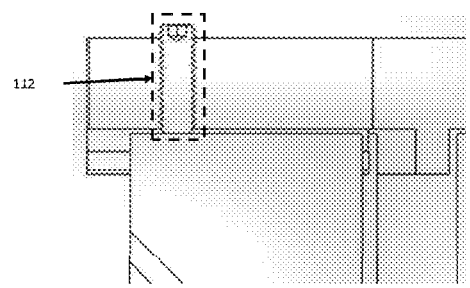
FIG. 15 is a close-up view of the set screw feature shown in FIG. 14.

In another embodiment, referring to FIGS. 14-15, there is a set screw mechanism 112 from the first ring 101 of the trocar such that the height (vertical position) of the second ring 103 is controlled and thus expansion limits are set.

FIG. 15 is side view of an alternative example embodiment with set screw mechanism 112 that would stop the elongate rigid members 106 from moving any further by either forming a physical barrier of moving any further out or by applying downwards pressure on them to prevent motion. The set screws 112 can also be designed to limit the motion of the second ring 103.

In one embodiment, the guiding members and rails of the cam mechanism 102 between the rigid members 106 and the second ring 103 are shaped like one-way rivets (not shown) or one-way zip-ties (not shown) that are present at regular intervals to allow for step-wise expansion and locking. The collapse or retraction of the second ring 103 (and hence the rigid members 106) is prevented at step-wise intervals.

The above mentioned mechanism of one-way rivets or zip-tie features can be implemented just at the final expanded (intended) diameter state. In some examples, one-way mechanical control device may be positioned at regular intervals along the second track 118 and configured to provide step-wise locking when the elongate rigid members 106 are moving away from each other.

In an alternative embodiment, a number of spring-loaded pins/latches (not shown) may be mechanically activated as the second ring 103 or the rigid members 106 reaches the final expansion state. These pins/latches are engaged in a perpendicular axis to the long-axis of motion of expansion ring to prevent it from moving back to an unexpanded state.

With reference to FIGS. 16-19, a tube 113 has a gasket 114 at the distal end of the tube 113. This tube 113 surrounds the outermost of the cannula device 100 (or trocar), and it extends all the way to the skin such that it forms a seal on the skin and creates an isolated space between the skin and the cannula device 100. Therefore, the gasket 114 provides a seal between the aperture defined by the rigid members 106 versus radially external to the aperture defined by the rigid members 106, e.g. the skin or tissue where the cannula device 100 is inserted. The gasket 114 is formed of resilient or elastic material in example embodiments. The resilient material may comprise fabric or polymer. In some example embodiments, the tube 113 may be comprised of rigid material.

In some examples, a resilient material is connected between the rigid members 106 along a length of the rigid members 106, where the resilient material is positioned on an outer surface of the rigid members 106, an inner surface of the rigid member, or in between the rigid members, or a combination of the outer surface, the inner surface or the in-between of the rigid members 106. The resilient material may create a seal between the rigid members 106 in an expanded position. Therefore, the resilient material provides a seal between the aperture defined by the rigid members 106 versus radially external to the rigid members 106, e.g. the skin or tissue where the cannula device 100 is inserted. The resilient material may be made of fabric or polymer.

Figure 16:
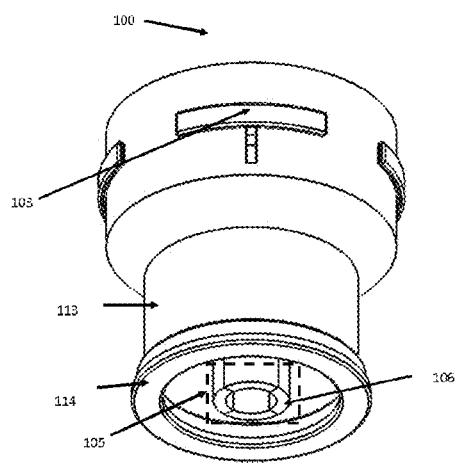
FIG. 16 is an isomeric view of an alternative example embodiment of the cannula device of FIG. 1 with a tube with a gasket at the distal end of the tube. The second ring, elongate rigid members forming a cannula are shown at the unexpanded state.
Figure 17:
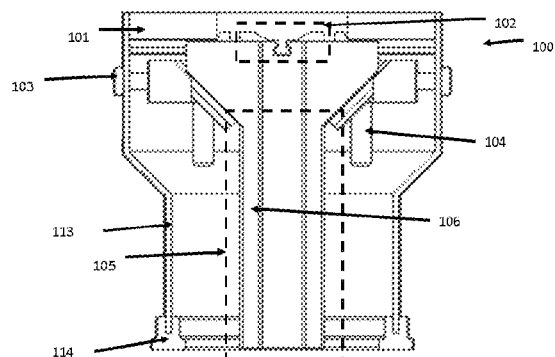
FIG. 17 is a cross-sectional side view of the cannula device of FIG. 16.
Figure 18:
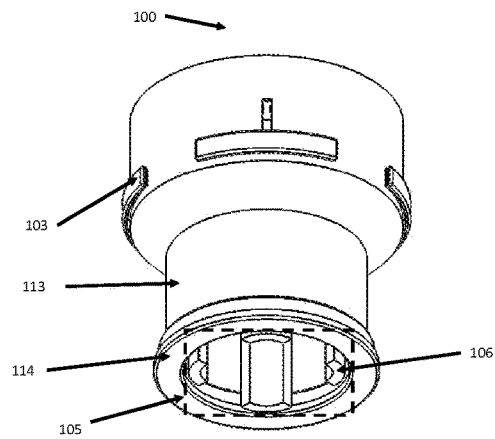
FIG. 18 is an isomeric view of the example embodiment of FIGS. 16-17, but shown with the rigid members at an expanded state.
Figure 19:
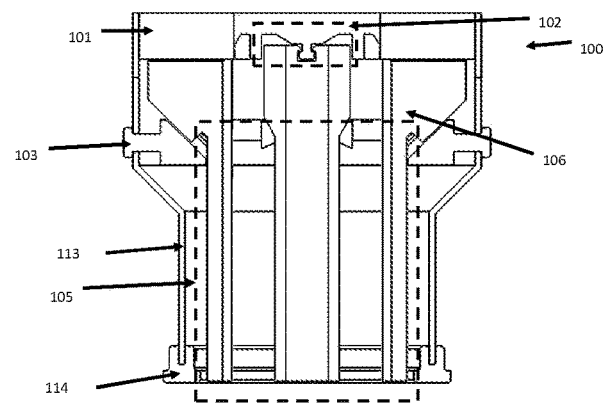
FIG. 19 is a cross-sectional side view of the example embodiment of FIG. 18.
Figure 20:
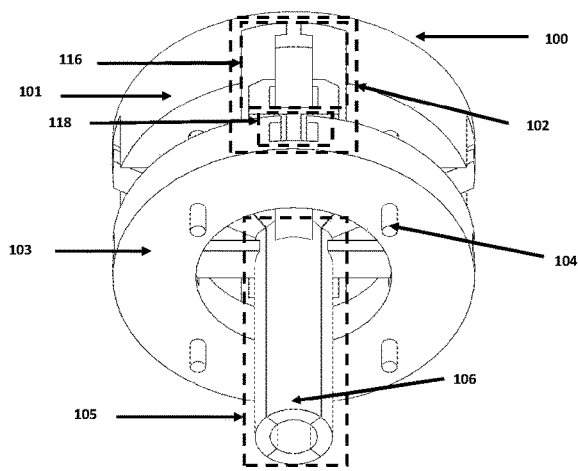
FIG. 20 is an isomeric view of an example expandable cannula device in an unexpanded state, having a pull to expand capability.
Figure 21:
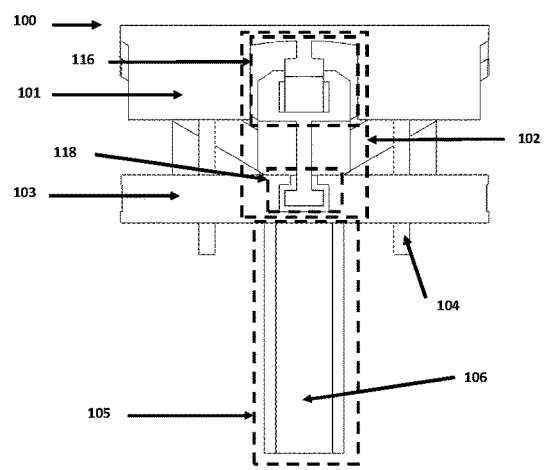
FIG. 21 is a side view of the example expandable cannula device shown in FIG. 20.
Figure 22:
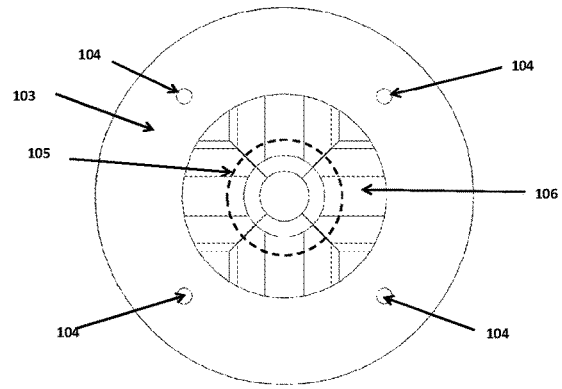
FIG. 22 is a bottom view of the example expandable cannula device of FIGS. 20-21.
Figure 23:
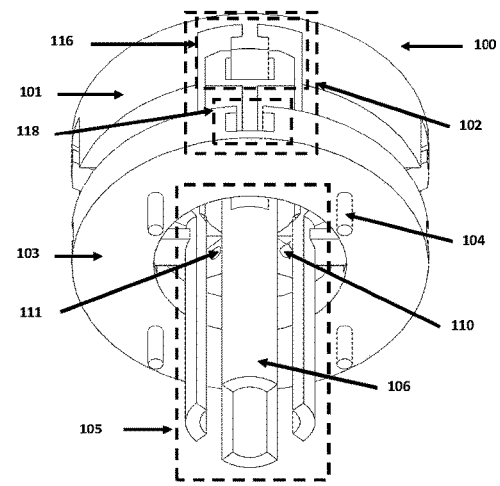
FIG. 23 is an isomeric view of the example expandable cannula device of FIGS. 20-22 in an expandable state.
Figure 24:
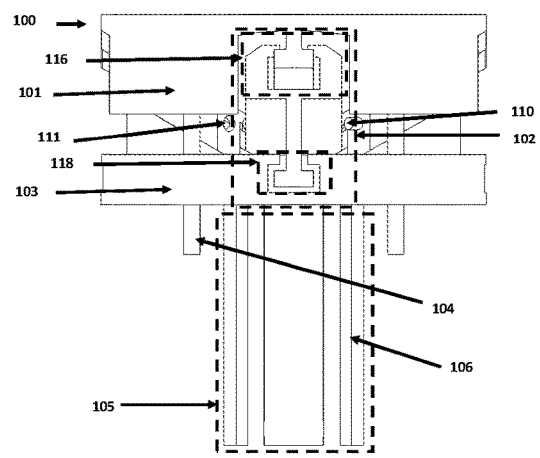
FIG. 24 is side view of the example expandable cannula device of FIGS. 20-23 in the expandable state.
Figure 25:
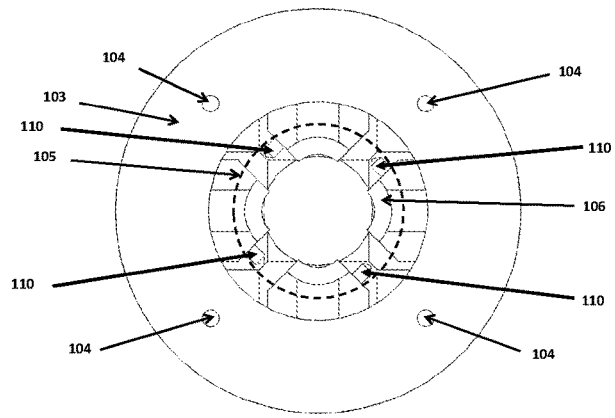
FIG. 25 is bottom view of the example expandable cannula device of FIGS. 20-24 in the expandable state.

FIG. 16 is an isometric view of an alternative example embodiment of the cannula device of FIG. 1 with a tube 113 with a gasket 114 at the distal end of the tube 113. The second ring 103, elongate rigid members 106 forming a cannula 105 are shown at the unexpanded state.

The tube 113 can be a telescoping tube that adjusts its length according to the preference of surgeon or according to how much of the trocar is inserted through the tissue.

Another example embodiment has a chamber (not shown) located either on top of the first ring or top of second ring 103, or below it or somewhere else on the cannula device 100. Such a chamber is filled with a fluid and linked to a piston where the expansion motion of the second ring 103 causes the piston to pressurize the chamber, thereby, emptying the fluid from the chamber into several linked balloon structures or one or more fluid filled or inflatable sacs (not shown), that may be of a suitable material that is relatively difficult to stretch, e.g. have a modulus of elasticity in the range of 12-2000 MPa, that are initially tucked in-between and sealed to the long axis of the rigid members 106. The inflation of these structures by the fluid creates a barrier or seal against gas leakage from the body or skin through the gaps between the expanded rigid members 106. The pressure in the balloon structures is maintained due to activation of one of the locking mechanisms mentioned previously on the second ring 106.

Fabric or polymer material (not shown), that are relatively difficult to stretch, e.g. can have a modulus of elasticity in the range of 12-2000 MPa, bonded or woven in-between the rigid member 106 gaps along the length of their long axis, such that when at the unexpanded state, these pieces of material are accordioned and do not obstruct the space within the lumen of the cannula 105. When at the expanded state, the accordioned material unravels and creates a barrier/curtain against leaking of fluids through the gaps between the expanded rigid members 106.

In some examples, a check valve is connected to the cannula 100 and is configured for releasing gas from the expandable cannula device.

The aforementioned gas loss prevention tube 113 and gasket 114 also acts as a mechanism of vertically supporting the trocar and anchoring it in one position.

A check-valve (not shown) is implemented within the inner side of the cannula 105 or first ring 101 of the cannula device 100, such that this valve would bleed gas from trocar and keep the insufflated region at a particular range of acceptable pressure that does not push the trocar out of the body.

A reduction of thickness or tapering (not shown) of a region of the cannula device's 100 rigid members 106 such that the internal diameter is maintained throughout the long axis of rigid members 106, but the outer diameter is decreased at this region. This reduction of outer diameter is created such that the pushed/compressed tissue would relax in this region and form an anchor point that reduces vertical motion of the cannula device 100.

A number of such reductions can be used to create a series of anchor points. Note this is not considered a thread-like or screw-like features, in some example embodiments.

In the following descriptions, the term proximal refers to a region closer to the housings of the expandable cannula device 100 located outside of the tissue, and the term distal refers to furthest point of the expandable cannula device 100 which is inside the tissue.

With reference to FIGS. 26-42: Push/pull mechanism.

An embodiment of an expandable cannula device 100 is shown comprising a first housing 1101 defining a first throughbore 1103; a plurality of elongate rigid members 1301 cooperatively defining a passage axially aligned with the first throughbore 1103, the plurality of elongate rigid members 1301 are connected to the first housing 1101; a second housing 1201 defining a second throughbore 1206, the second housing 1201 moveable in an axial direction with respect to the first housing 1101, the second housing 1201 being operably connected to the elongate rigid members 1301 so that axial movement of the second housing 1201 with respect to the first housing 1101 causes the plurality of elongate rigid members 1301 to move away from each other and increase a size of the passage. In some embodiments, the expandable cannula device 100 comprises a second housing 1201 that is configured to at least partially surround the first housing.

In some embodiments, the expandable cannula device 100 is comprised of a first housing 1101, a second housing 1201, a plurality of elongate rigid members 1301 and an obturator 1001. The first housing 1101 defines a throughbore 1103 and the second housing 1201 defines a second throughbore 1206, the throughbores are axially aligned and are also axially aligned with the unexpanded passage 1308 defined by the unexpanded elongate rigid members 1301, as well as the expanded passage 1309 defined by the expanded elongate rigid members 1301.

In some embodiments, the second housing 1201 is configured to surround the first housing 1101.

The inner diameter of the expandable cannula device 100 can be increased by moving the elongate rigid members 1301 away from each other in order to create a passage with a second diameter that is larger than the first. In this embodiment, this is performed by changing the axial position of the second housing 1201 relative to the first housing 1101. This change in the relative axial position causes each of the plurality of first tongue feature 1302 of each of the plurality of elongate rigid members 1301 to slide within each of the plurality of guide grooves 1102 of the first housing 1101. Each of the plurality of elongate rigid members 1301 also comprises a second tongue feature 1303, and the second housing 1201 has a plurality of guide grooves 1204, in which each of the second tongue features 1303 can slide.

The first tongue feature 1302 of each of the plurality of the elongate rigid members 1301 and the plurality of guide grooves 1102 of the first housing 1101 are configured at the same angle relative to the central axis of the expandable cannula device 100. Likewise, the second tongue features 1303 of the elongate rigid members 1301 and the plurality of guide grooves 1204 of the second housing 1201 are configured at the same angle relative to the central axis of the expandable cannula device 100.

In some embodiments (not shown), the angles of the plurality of first tongue features 1302 and plurality of guide grooves 1102 and the angles of the plurality of second tongue features 1303 and plurality of guide grooves 1204 can be configured to select the direction of axial motion of the second housing 1201 relative to the first housing 1101 that causes the elongate rigid members 1301 to expand. In some embodiments, the direction of motion that causes expansion is the movement of second housing 1201 towards the first housing 1101. In some embodiments (not shown), the direction of motion of second housing 1201 is away from the first housing 1101.

The second housing may be manufactured in one-piece by established means, for example, extrusion or molding. In some embodiments, the second housing 1201 is assembled from two parts, each has mating grooves 1202 and mating tongues 1203, where the mating tongues 1203 of one piece are inserted into the mating grooves 1202 of the second piece.

In some embodiment, the elongate rigid members 1301 have an outer surface taper 1304 that improves the structural rigidity of the elongate rigid members 1301 and prevents a deeper than necessary insertion of the expandable cannula 100 into the tissue.

The elongate rigid members 1301 may comprise a distal tip 1306, which may be blunt to prevent injury of tissue during insertion of expandable cannula device 100 into the tissue. The distal tip 1306 may be tapered to facilitate insertion.

With reference to FIGS. 43-49: a twisting push/pull mechanism.

An embodiment of the previously described expandable cannula device 100 is shown. Wherein the axial movement of the second housing 1501 relative to the first housing 1401 is effected by rotation.

In this embodiment, the first housing 1401 comprises threaded features 1404 on its external surface. It also contains a plurality of guiding grooves 1402 for sliding of the plurality of elongate rigid members 1301 and a throughbore 1403.

The second housing 1501 also comprises a plurality of guide grooves 1502 for sliding of elongate rigid members 1301. In this embodiment, it is comprised of a rotatable threaded part 1504 that contains threaded features 1503 on its internal surface. The rotatable threaded part 1504 rotates about the central long axis of the expandable cannula device 100 by sliding on rotation guide track 1505 which remains stationary because it is connected to a non-rotating part 1506 of the second housing 1501. The non-rotating part 1506 also contains a plurality of guide grooves 1502 for sliding of the plurality of elongate rigid members 1301 during expansion or contraction.

Expansion of the elongate rigid members 1301 is caused by rotation of the rotatable threaded part 1504 about the central long axis of the throughbore 1403 while being threadedly mated to the threaded features 1404 of the first housing 1401, which causes the rotatable threaded part 1504 to move the non-rotating part 1506 of the second housing 1501 in an axial motion relative to the first housing 1401 and thus cause the elongate rigid members to move away from each other and thus expand the passage of the expandable cannula device 100 from an unexpanded passage 1308 to an expanded passage 1309.

In some embodiments (not shown), the first housing 1401 and second housing 1501 further comprising a centering mechanism for axially aligning the first throughbore and the second throughbore, the centering mechanism configured between the first housing 1401 and the lower portion of the second housing 1501.

In some embodiments (not shown), the centering mechanism comprises a plurality of pins and receptacles for receiving the plurality of pins, wherein the receptacles (or pins) are configured in the lower portion of the second housing 1501.

In some embodiments (not shown), the centering mechanism further comprising a one-way ratchet configured between the first housing 1401 and the second housing 1501 to constraint movement of the second housing 1501 to one axial direction.

With reference to FIGS. 26-42: centering mechanisms.

In some embodiments, the expandable cannula device 100 further comprises a centering mechanism for axially aligning the first throughbore 1103 and the second throughbore 1206. In some embodiments, the centering mechanism comprises a plurality of concentricity features 1205 and a plurality of complimentary concentricity features 1104. In some embodiments, the concentricity features 1205 comprise a plurality of pins, and the complimentary concentricity features 1104 comprise a plurality of receptacles for receiving the plurality of pins. In some embodiments (not shown), the centering mechanism further comprises a one-way ratchet.

In some embodiments, the first housing 1101 and second housing 1201 are kept concentric, for example, by concentricity features 1205 in the second housing 1201 mated to the complimentary concentricity features 1104 in the first housing 1101. In some embodiments, the concentricity features 1205 and complimentary concentricity features 1104 comprise tongues and grooves or vice versa.

In the expandable cannula device 100 embodiment, where relative movement of the second housing 1501 to the first housing 1401 is achieved by rotation of the rotatable threaded part 1504, similar concentricity features 1205 and complimentary concentricity features 1104 (not shown) may be located on the inner surface of the non-rotating part 1506 and the first housing 1401.

In some embodiments (not shown), concentric alignment of the first housing 1101 or 1401 and the second housing 1201 or 1501 is achieved via a plurality of elongate guiding pins 104. In some embodiments, the plurality of guiding pins 104 extend from the first housing 1101 or 1401 and are received by the second housing 1201 or 1501. In some embodiments, the guiding pins 104 extend from the second housing 1201 or 1501 and are received by the first housing 1101 or 1401.

In some embodiments (not shown), the concentricity features 1205, complimentary concentricity features 1104 or guiding pins 104 comprise one-way movement locking features, such that the movement of the second housing 1201 or 1501 relative to the first housing 1101 or 1401 may occur in one direction only. In some embodiments, the locking features, comprise complimentary one-way ratchet features on the moving parts.

With reference to FIGS. 50-52: a telescoping mechanism for insertable member.

In some embodiments, the expandable cannula device 100 further comprises an insertable member 4901 housed in the first housing 1101, said insertable member 4901 attached via an actuation mechanism to the second housing 1201 such that movement of the second housing 1201 relative to the first housing 1101 causes the insertable member 4901 to move along the central axis of the expandable cannula device 100. In some embodiments, the actuation mechanism comprises a telescoping mechanism. In some embodiments, the telescoping mechanism may be mechanical, hydraulic or pneumatic.

In some embodiments, the insertion of an insertable member 4901 into the expanded passage 1309 of the expandable cannula device 100 may occur simultaneously while the expandable cannula device 100 is expanded, instead of having to insert said insertable member 4901 after the expandable cannula is expanded, thus saving time and making the process more streamlined for the user.

In order to do this, in some embodiments, an insertable member 4901 is housed within the throughbore 1103 of the first housing 1101, wherein the insertable member 4901 is connected by at least one actuation mechanism to the second housing 1201, such that the movement of the second housing 1201 relative to the first housing 1101 causes the actuation mechanism to move the insertable member 4901 in an axial direction relative to the central axis of the expandable cannula device 100.

In some embodiments, the axial movement of the second housing 1201 relative to the first housing 1101 causes the elongate rigid members 5101 to expand and therefore alter the unexpanded passage 1308 to an expanded passage 1309. In some embodiments, the axial movement of second housing 1201 relative to the first housing 1101 causes the actuation mechanism to propel the insertable member 4901 into a distal direction and into the expanded passage 1309.

In some embodiments, the actuation mechanism may be a telescoping mechanism. In some embodiments, the telescoping mechanism may be mechanical, such as spring-based, or pneumatic or hydraulic.

In some embodiments, where the actuation mechanism is a telescoping mechanism, the insertable member 4901 is housed within the first housing 1101 however is not inside the unexpanded passage 1308 defined by the plurality of the elongate rigid members 5101. The at least one telescoping mechanism is connected to the insertable member 4901 via a pivot pin 5302 from one end and connected to the second housing 1201 via another pivot pin 5301. The axes of the pivot pin 5301 and pivot pin 5302 are perpendicular to the central axis of the expandable cannula device 100. When the expandable cannula device 100 is configured to have an unexpanded passage 1308, the telescoping mechanism is unexpanded, and the axes of the pivot pin 5301 and pivot pin 5302 are offset by a first distance, relative to the central axis of the expandable cannula device 100. When the second housing 1201 moves in a direction relative to the first housing 1101 to cause expansion of the elongate rigid members 5101, the axes of the pivot pin 5301 and pivot pin 5302 become further offset by a second distance, relative to the central axis of the expandable cannula device 100, such that the second distance is greater than the first distance. The increase of the offset distance between pivot pin 5301 and pivot pin 5302 causes the unexpanded telescoping mechanism 5303 to become an expanded telescoping mechanism 5304. In the expanded configuration, the insertable member 4901 is advanced into the expanded passage 1309 of the expandable cannula device 100.

With reference to FIGS. 53-58: actuating member causing expansion.

Another mechanism for expanding the expandable cannula device 100 is provided; a first housing 1801 defining a first throughbore; a plurality of elongate rigid members 2001 cooperatively defining a passage axially aligned with the first throughbore, and the plurality of elongate rigid members 2001 are connected to the first housing 1801; an actuating member 1901 defining a second throughbore 1903 axially aligned with the passage, such that the axial movement of the actuating member 1901 causes the plurality of elongate rigid members 2001 to move radially relative to each other.

In this embodiment the device is comprised of a first housing 1801, an actuating member 1901 that when inserted from a proximal region to a distal region of the first housing 1801 causes the elongate rigid members 2001 to move away from each other.

The first housing 1801 comprises a plurality of guide grooves 1802 that each receives a tongue feature 2004 of the plurality elongate rigid members 2001 to slide away from each other during expansion and to slide toward each other during contraction. In some embodiments, the first housing 1801 comprising threaded features 1803 on its internal surface and the actuating member 1901 has a threaded feature 1902 on its external surface such that the actuating member 1901 can be threadedly rotated into the threaded features 1803 of the first housing 1801 in order to move the actuating member 1901 into a distal position inside the first housing 1801.

In some embodiments (not shown), the actuating member 1901 may comprise a portion having an exterior shape complementary to an interior shape of at least a portion of the first housing 1801. These complimentary portions may be tapered.

In some embodiments, the plurality of elongate rigid members 2001 cooperatively define a first inner surface portion 2003 proximal to the first housing 1801, and the actuating member 1901 comprises a second exterior portion 1904 complementary to the first inner surface portion 2003. In some embodiments, said portions 2003 and 1904 comprise complimentary tapers. In some embodiments, the second exterior portion 1904 is frustoconical.

In some embodiments the first housing 1801 may comprise complimentary features 1804 to the outer surface 2002 of the elongate rigid members 2001 that can support the elongate rigid members 2001 when they are in an expanded position. These complimentary surfaces may be tapered.

In some embodiments, the actuating member 1901 comprises a throughbore 1903. In some embodiments, the throughbore 1903 comprises a central lumen. In some embodiments, the throughbore 1903 may be cylindrical.

In some embodiments, the actuating member 1901 comprises a generally circular or oval cross-section perpendicular to an axis of the passage of the expandable cannula device 100.

The actuation member 1901 may comprise a handle 1905 that can be used for rotating or pushing the actuation member.

In some embodiments, the actuating member 1901 comprises an insertable member 4901.

In some embodiments, the insertable member 4901 comprises an actuating member 1901.

Expansion of the expandable cannula device 100 passageway occurs when the inner surface portion 2003 of the elongate rigid members 2001 is subject to a force by the second exterior portion 1904 of the actuating member 1901 that is caused by inserting the actuating member 1901 distally into the first housing 1801. In some embodiments, the distal motion of the actuating member 1901 into the first housing 1801 is achieved by threaded rotation (or insertion) of the actuating member 1901.

In some embodiments, the expandable cannula device 100 further comprises a locking mechanism (not shown) for preventing or restricting the actuating member 1901 from axially moving relative to the first housing 1801.

In some embodiments, insertion of the actuation member 1901 distally into the expandable cannula, causes the elongate rigid members 2001 become expanded wherein a locking mechanism is activated such that the elongate rigid member 2001 are locked into their expanded state, and the actuating member 1901 may be removed from the expandable cannula. Examples of locking mechanisms may be found in other described embodiments and may be utilised in these embodiments as well. An example of locking mechanism comprises one-way ratchet features on between the plurality of the guide grooves 1802 of the first housing 1801 and each of the of tongue features 2004 of the plurality of elongate rigid members 2001.

With reference to FIGS. 59-62: insertable member.

In some embodiments of the same invention, an insertable member 4901 and an obturator 5001 are inserted through the throughbore 1903 of the actuating member 1901 and through the expanded passage 1309 of the expandable cannula device 100. The obturator 5001 and the insertable member 4901 are used in similar fashion as in other described embodiments.

With reference to FIGS. 63-66: twisting pin embodiment.

An alternative mechanism of an expandable cannula device 100 is illustrated. In this embodiment, a first housing 1801 contains a spiral track 2304 and a plurality of guide grooves 1802 for guiding the movement of each of the tongue features 2004 of the plurality of elongate rigid members 2001. A pin 2301 having a shaft 2302 is disposed within the spiral track 2304, wherein the shaft terminates with a tip 2303. In some embodiments, the tip 2303 may be complimentary to the inner surface portion 2003 of any of the elongate rigid members 2001. The tip 2303 and the inner surface portion 2003 may comprise complimentary tapers.

By sliding the pin 2301 from a first position close to the central axis of the first housing 1801 along the spiral track 2304 towards a second position that is radially distant position than the first position, the pin's tip 2303 sequentially forces the plurality of elongate rigid members 2001 to move away from each other, from an unexpanded passage 1308 and create an expanded passage 1309.

In some embodiments, the pin 2301 may be removed from the spiral track 2304 of the first housing 1801 after the elongate rigid members 2001 are expanded.

In some embodiments (not shown), the shaft 2302 of the pin 2301 and the spiral track 2304 comprise a locking mechanism such that the pin 2301 may only move in direction along the spiral track 2304. For example, the locking mechanism may comprise complimentary one-way ratchet features on the spiral track 2304 and the shaft 2302.

With reference to FIGS. 67-74: twist introduced/conveyor belt insert system.

An alternative mechanism of an expandable cannula device 100 is illustrated. The expandable cannula device 100 is comprised from a first housing 2401 with a first throughbore 2404, a hub defining a second throughbore that is continuous with the first throughbore, and comprising at least one rotatable member 2501, a plurality of elongate rigid members 2701 housed and movable within the first housing 2401 and comprising a continuous passage of the expandable cannula device 100, and at least one rigid member 2601 having an outer circumference larger than an inner circumference of a cross-section of the unexpanded passage 1308 defined by the plurality of unexpanded elongate rigid members 2701, wherein the said at least one rigid member 2601 may be housed within the first housing 2401, a coupling mechanism between the at least one rotatable member 2501 and the at least one rigid member 2601 such that the rotation of the at least one rotatable member 2501 causes the at least one rigid member to move into a distal region of the cannula, and cause the elongate rigid members 2701 to move away from each other and thus form an expanded passage 1309.

In some embodiments, the at least one rigid member 2601 comprises a lumen. In some embodiments, the lumen comprises a circular cross-section.

With reference to FIGS. 67-70: wires embodiment.

In this embodiments, the at least one rotatable member 2501 comprises a rotating component that rotates about a central axis of the first housing 2401, the at least one rigid member 2601 is coupled to the rotating component 2501 by a coupling mechanism that comprises a plurality of wires 2801, which extend from the at least one rigid member 2601 to at one of the plurality of wire threading guide features 2503 which are disposed onto the rotatable member 2501.

The first housing 2401 comprises a plurality of guide grooves 2402 for allowing the proximal portion of each of the plurality of elongate rigid members 2701 to slide through each of the plurality of guide grooves 2402 when said members move away from the central axis of the first housing 2401. The first housing 2401 also comprises a sliding track 2403 onto which the rotatable member 2501 can freely slide/glide when it rotates about the central axis of the first housing 2401. The first housing 2401 also comprises a throughbore 2404 that creates a passage that connects to the passage creates by the plurality of elongate rigid members 2701.

An at least one rigid member 2601 is initially disposed in the throughbore 2404 of the first housing 2401 when the device has an unexpanded passage 1308. The at least one rigid member 2601 has a distal edge that is complimentary to the inner tapered surface of the elongate rigid members 2701 (as shown in previous embodiments). The distal edge may be tapered.

The at least one rigid member 2601 has a plurality of holes 2603 through which the plurality of wires 2801 can be threaded and anchored tightly through these holes 2603.

The plurality of said wires 2801 extend from the lumen of the expandable cannula device 100 (on the inner surface of the elongate rigid members 2701) towards a distal section of the elongate rigid members 2701 and exit the lumen of the expandable cannula device 100. The wires 2801 then are disposed along the outer surface of elongate rigid members 2701 and on the external surface of the first housing 2401 and are then connected and affixed to at least one of the plurality of wire threading guiding features 2503 which are located on the rotatable member 2501. In some embodiments (not shown), the wires may exit the lumen of the expandable cannula device 100 at more proximal section of the elongate rigid members 2701, through holes (not shown).

In other embodiments (not shown) The wires may also be housed within a lumen formed along the inner surface of the elongate rigid members 2701, wherein said lumen travels and extends towards the outer surface of the elongate rigid members and may extend to the first housing 2401 as well.

The rotation of the rotatable member 2501 about the central axis of the first housing 2401 causes the plurality of the wires 2801 to become tensioned and pulled. This in turn causes the at least one rigid member 2601 to advance into a distal position in the expandable cannula device 100, thereby pushing the plurality of elongate rigid members 2701 away from each other towards an expanded state.

In some embodiments, the at least one rigid member 2601 has central throughbore that creates a lumen that is continuous with the lumen created by the plurality of the elongate rigid members 2701 and with the lumen of the first housing 2401 that is created by the throughbore 2404.

With reference to FIGS. 71-74: conveyor belt mechanism.

In this embodiment, the at least one rotatable member 2501 comprises a system of mechanical gears with at least one handle extending outside of the first housing 2401. In some embodiments, the system of mechanical gears comprises a system of worm-drives, such that the rotation of a first rotatable member 2501, causes the rotation of a first worm wheel 2504 along an axis perpendicular to the axis of the first rotatable member 2501. The first worm wheel 2504 further comprises a shaft and threads (worms) that are configured to cause rotation of a second worm wheel 2505 and a third worm wheel 2506 in opposite directions, wherein the axes of the second worm wheel 2505 and third worm wheel 2506 are perpendicular to the axis of the first worm wheel 2504. Disposed onto the shaft of the second worm wheel 2505 is a first roller drum 2507, and onto the shaft of the third worm wheel 2506 is a second roller drum 2508, wherein the first roller drum 2507 and second roller drum 2508 rotate in opposite directions to each other when the rotatable member 2501 is rotated.

In some embodiments (not shown), there may be more or less worm-drive mechanisms to produce a similar effect. In some embodiments (not shown), there may be a different system of mechanically driven components to effect a similar result onto the first roller drum 2507 and second roller drum 2508. In some embodiments (not shown), there may be more roller drums.

A coupling mechanism is disposed between each of the first roller drum 2507, the second roller drum 2508 and the at least one rigid member 2601. In some embodiments, the coupling mechanism comprises at least one conveyor belt. In this embodiment, a first conveyor belt 2802 is connected to the first roller drum 2507, and a second conveyor belt 2803 is connected to the second roller drum 2508.

Each of the first conveyor belt 2802 and second conveyor belt 2803 comprise a loop that extends from the inner surface of the elongate rigid members 2701, and then to the outside surface of the elongate rigid members, and back to the first housing 2401. In some embodiments (not shown), the conveyor belts may exist the elongate rigid members 2701 at a more proximal region through holes in the body of the elongate rigid members 2701 (not shown).

In some embodiments, the first housing 2401 comprises an opening 2405 for introducing the at least one rigid member 2601 into its throughbore 2404.

In some embodiments (not shown), the at least one rigid member 2601 may be introduced into the housing via removable cartridge insertion mechanism such that the cartridge can be removed after the at least one rigid member 2601 is introduced into the throughbore 2404 of the first housing 2401.

The at least one rigid member 2601 becomes sandwiched between the first conveyor belt 2802 and second conveyor belt 2803, wherein a frictional connection is formed between the first conveyor belt 2802 and second conveyor belt 2803 and the at least one rigid member 2601, such that the rotation of the rotatable member 2501 causes the first conveyor belt 2802 and second conveyor belt 2803 to move into a distal direction, and forces the at least one rigid member 2601 to move along with it due to friction.

The advancement of the at least one rigid member 2601 towards a distal region of the unexpanded passage 1308 causes the plurality of elongate rigid members 2701 to move away from each other and form an expanded passage 1309 that has a cross-sectional inner diameter equivalent to the cross-sectional outer diameter of the at least one rigid member 2601.

Rotation of the rotatable member 2501 in an opposite direction causes the first roller drum 2507 and second roller drum 2508 to rotate in an opposite direction, and thus the first conveyor belt 2802 and second conveyor belt 2803 move from a distal to proximal direction, therefore, bringing the at least one rigid member 2601 towards throughbore of the first housing 2401.

In some embodiments, the first conveyor belt 2802 and second conveyor belt 2803 are made from a stretchable elastic material, such that the total length of each belt may be extended.

In some embodiments (not shown), the first conveyor belt 2802 and second conveyor belt 2803 may comprise a derailleur-like system that maintains a level of tension of each of the belts by adjusting their effective length while the elongate rigid members 2701 are moving away from each other.

In some embodiments (not shown), the first conveyor belt 2802 and second conveyor belt 2803 may comprise chains. In some embodiments, at least one rigid member 2601 may comprise an outer surface with gear features that are complimentary with said chains.

In some embodiments (not shown), an expandable cannula device 100 comprises a similar mechanism of the one above wherein the first conveyor belt 2802 and second conveyor belt 2803 comprise wires that are attached to the at least one rigid member 2601, wherein said wires extend through the passage defined by the elongate rigid members 2701, and extend towards the external surface of the elongate rigid members and up to the first housing, where they are then are attached to the first roller drum 2507 and second roller drum 2508, such that the rotation of the rotatable member 2501 causes the first roller drums 2507 and second roller drum 2508 to tension the wires and wound them, thereby pulling the at least one rigid member 2601 distally into the unexpanded passage 1308, causing the elongate rigid members 2701 to move away from each other and form an expanded passage 1309.

With reference to different embodiments of the at least one rigid member 2601, in some embodiments, it may comprise a lumen with a generally circular cross-section.

With reference to different embodiments of the at least one rotatable member 2501, in some embodiments (not shown), may comprise a locking mechanism for preventing or restricting the at least one rotatable member 2501 from causing the at least one rigid member 2601 from axially moving relative to the first housing 2401. In some embodiments (not shown), the locking mechanism may comprise one-way rotational movement locking mechanisms, such as one-way ratchet gears, or other rotational locking mechanisms known to the those familiar with mechanical arts.

In some embodiments (not shown), the at least one rotatable member 2501 may be driven by a motor. In some embodiments, the motor may be electrically operated, battery operated or pneumatically operated.

With reference to FIGS. 75-81: retractable pin/receptacle for locking.

In some embodiments, the first housing 3501 comprises a plurality of pin grooves 3502 and a plurality of additional pin grooves. In some configurations, a pin 3401 is placed into the pin groove 3502 Such that a portion of it is protruding outside of the pin groove 3502. In some embodiments, the pin 3401 is removable. The protruding portion of the pin 3401 prevents the stopping face 3602 of the second housing 3601 from moving in an axial direction relative to the central axis of the first housing 3501 and thus controls the level of expansion of the elongated rigid members 3701 away from each other.

In some embodiments, the pin 3401 can be further inserted into the pin groove 3502 or can be removed entirely from the pin groove 3502 such that the second housing 3601 is permitted to move in an axial direction relative to the central axis from the first housing 3501 in order to further expand the expandable cannula device 100 by moving the elongate rigid members 3701 further away from each other.

In some embodiments a system of pin 3401 and pin groove 3502 and additional pin 3402 and additional pin groove provide a stepwise control for the expansion of the expandable cannula device 100.

In other embodiments (not shown), the pin 3401 and pin grooves 3502 comprise a "retractable pen" mechanism such that the pins 3401 can be pushed into the pin grooves 3502 by a pressing action, and then retracted by another pressing action in order for the device to be reused.

In some embodiments (not shown), the pins 3401 and pin groove 3502 may be located on the proximal surface of the first housing 1801, in order to control the level of threaded rotation (and thus distal insertion) of the actuating member 1901, and thus the amount of expansion of the expanded passage 1309. In some other embodiments (not shown), the pins 3401 and pin grooves 3502 may be located on the inner surface of the first housing 1801 in order to limit the distal insertion of the actuating member 1901 and thus control the amount of expansion of the expanded passage 1309.

In some embodiments, the expandable cannula device 100 may be configured to be in an initial expanded passage 1309 state, and there is a need to contract it. The pins 3401 and pin groove 3502 embodiments described above may be used to provide step-wise contraction control as well.

In some embodiments, the expandable cannula device 100 may be configured to be in an initial expanded passage 1309 state, and there is a need to contract it towards an unexpanded passage 1308, wherein the above mechanism can be used to provide a controlled step-wise contraction.

With Reference to FIGS. 82-85: spring-loaded pins.

In another embodiment showing a different mechanism controlling the expansion of an expandable cannula device 100, the first housing 3801 comprises a pinhole 3802, and the second housing 3901 comprises a pinhole 3902. When the expandable cannula device 100 has an unexpanded passage 1308 defined by unexpanded elongate rigid members 4101, the pinhole 3802 of the first housing 3801 and the pinhole 3902 of second housing 3901 have axes that are parallel but are at an offset distance from each other. This forces the pin 4001 which is attached to a compression spring to remain inside the first housing 3801 pinhole 3802 and causes the compression spring to become a compressed compression spring 4002, when the second housing 3901 is moved in an axial direction relative to the central axis of the first housing 3801, the offset distance between the axis of pinhole 3802 and pinhole 3902 is reduced until they become collinear which allows the compressed compression spring 4002 to release its energy and become an uncompressed compression spring 4003 which further moves the pin 4001 from the pinhole 3802 which is in the first housing 3801 towards the pinhole 3902 in the second housing 3901 while having a portion of it remaining in the pinhole 3802 and therefore locks the axial movement of the second housing 3901 relative to the first housing 3801, which controls the amount of expansion of the elongate rigid members 4101 away from each other.

In some embodiments, the pins 4001 and the uncompressed compression spring 4003 may be pushed manually towards the first housing 3801 pinhole 3802, where the compression spring becomes a compressed compression spring 4002 again, and motion of the second housing relative to the first housing is permitted. In some embodiments (not shown), a system of a plurality of pins 4001, springs, and pinholes 3802 on the first housing 3801 and pin holes 3902 on the second housing 3901, allows for a step-wise expansion.

In some embodiments (not shown), the location of the pins 4001 and the springs can be reversed from the first housing 3801 pinhole 3802 to the second housing 3901 pinholes 3902. For example the compressed compression springs 4002 and pin 4001 may be located on the pinholes 3902 of the second housing 3901. The spring becomes an uncompressed compression spring 4003 when the axes of the pinholes 3802 and 3902 are collinear, such that the pin 4001 is advanced from the second housing 3901 pinhole 3902 to the first housing 3801 pinhole 3802, while having a portion of it remaining in the second housing 3901 pinhole 3902 in order to relative prevent axial movement between the first housing 3801 and second housing 3901.

Control of Contraction:

In some embodiments, the expandable cannula device 100 may be configured to be in an initial expanded passage 1309 state, and there is a need to contract it towards an unexpanded passage 1308. The spring and pin hole embodiments described above may be used to provide step-wise contraction control as well.

With reference to FIGS. 86-91: spring-loaded elongate rigid members.

Another embodiment of an expandable cannula device 100 further comprises a biasing mechanism for biasing the plurality of elongate rigid members 4301.

In some embodiments, the first housing 4201 (in other embodiments can be the second housing or both the first and second housing) comprises a biasing mechanism mounting wall 4202 at position in the groove 4203 where elongate rigid members 4301 slide relative to central axis of the expandable cannula device 100. Disposed between the outer surface of the elongate rigid members 4301 and the biasing mechanism mounting wall 4202 is a biasing mechanism. In some embodiments, the biasing mechanism comprises an uncompressed compression spring 4401, which causes the elongate rigid members 4301 to remain in an unexpanded position and close to each other thus create an unexpanded passage 1308. This prevents accidental sliding of the elongate rigid members 4301 in the grooves of the first housing 4201 and thus accidental expansion of the passage.

Only when the user applies a sufficient force to expand the elongate rigid members 4301 by methods described in previous embodiments of this description, then the external surface of the elongate rigid members 4301 apply a force onto the uncompressed compression spring 4401 and make it a compressed compression spring 4402 when the elongate rigid members 4301 are away from each other and comprising an expanded passage 1309.

In some embodiments (not shown), the biasing mechanism may be comprised of a compressible foam material.

In some embodiments (not shown), the spring is a tension spring, configured to bias the elongate rigid members 4301 to a position away from central axis of the expandable cannula device 100.

With reference to FIGS. 92-95: ratchet features to force 1-way movement of elongate rigid members.

Another embodiment showing a different mechanism controlling the expansion of an expandable cannula device 100, wherein the expandable cannula device 100 further comprises a guiding mechanism for preventing the elongate rigid members 4601 from moving radially. In some embodiments, the guiding mechanism comprises complimentary one-way ratchet features, such that the movement of elongate rigid members 4601 is constrained to one radial direction.

In some embodiments, the first housing 4501 (in other embodiments this may be can be the first and/or the second housing) comprises ratchet features 4502 in the guiding grooves 4503 where the elongate rigid members 4601 can slide to expand the unexpanded passage 1308 of the expandable cannula device 100 and move away from each other and from an expanded passage 1309. The elongate rigid members 4601 in this embodiment have complimentary ratchet features 4602, such that once they are expanded from a first position to a second position, the ratchet features 4502 and complimentary ratchet features 4602 prevent the elongate rigid members 4601 from returning to the first position. This embodiment forces a one-way expansion for the expandable cannula device 100.

In some embodiments (not shown), the ratchet features 4502 and complimentary ratchet features 4602 are located on the outer surface of the first housing 1101 and the inner surface of the second housing 1201.

In some embodiments (not shown), the concentricity features 1205 and complimentary concentricity features 1104 described in previous embodiments, may further comprise ratchet features 4502 and complimentary ratchet features 4602 respectively.

In some embodiments (not shown), the ratchet features 4502 and complimentary ratchet features 4602 may be placed on the threaded features 1404 of the first housing 1401 and the threaded features 1503 of the second housing 1501 of an embodiment of the expandable cannula device 100.

In some embodiments (not shown), the ratchet features 4502 and complimentary ratchet features 4602 may be placed on the threaded features 1803 of the first housing 1801 and the threaded features 1902 of an actuating member 1901.

In another embodiment (not shown), the ratchet features 4502 and complimentary ratchet features 4602 can be reversed in direction, such that an expanded expandable cannula device 100 with an expanded passage 1309 may only be contracted to an unexpanded passage 1308 where the elongate rigid members 4601 come close to each other.

With reference to FIGS. 96-103: hinged elongate rigid members.

An alternative mechanism of an expandable cannula device 100 is illustrated. Where in this embodiment, the expandable cannula device 100 is composed of a first housing 2901 with a central throughbore similar to previous embodiments, a plurality of hinged elongate rigid members 3001 which are connected via hinges 3101 to the first housing 2901 and via another set of hinges 3101 to another set of plurality of hinged elongate rigid members 3001, wherein the plurality of hinged elongate rigid members 3001 cooperatively define a passage that is aligned with the central throughbore of the first housing 2901. A compressive sleeve 3201 surrounds outer circumference of the plurality of hinged elongate rigid members 3001 and restricts their radial movement. In some embodiments, the compressive sleeve 3201 causes the plurality of hinged elongate rigid members 3001 to come in close proximity together and form an unexpanded passage 1308.

The insertion of an expansion insert 3301 into the expandable cannula device 100 causes the hinged elongate rigid members 3001 to move away from each other, while the compressive sleeve 3201 prevent them from becoming loose and conforming to shape dictated by the forces of gravity. The expansion insert 3301 may comprise a central lumen that has a diameter that is larger than the diameter formed by the unexpanded passage 1308 and permits the passage of instruments and specimen through it.

In some embodiments, the hinges 3101 comprise ratchet features 3102 such that movement of hinged elongate rigid members 3001 is possible in only one direction. In some embodiments, the ratchet features 3102 may prevent collapse of expanded hinged elongate rigid members 3001 from a larger diameter to a smaller diameter due to the compressive sleeve 3201, especially after the removal of an expansion insert 3301 from the expanded passage 1309 of the expandable cannula device 100.

In some embodiments, the expansion insert 3301 is an insertable member 4901 similar to other insertable members of other embodiments in this disclosure.

In some embodiments the compressive sleeve 3201 is comprised of an elastic polymer. In some embodiments, the compressive sleeve 3201 is also a fluid leakage prevention seal that prevents any media to be transmitted through the gaps between the expanded hinged elongate rigid members 3001.

With reference to FIGS. 104-111: an insertable member with an obturator.

In this embodiment, the expandable cannula device 100 further comprises an insertable member 4901 insertable into the central passage by an elongate device.

In some embodiments, the insertable member 4901 comprises a short axial length and a central lumen 4903. In some embodiments, the elongate device comprises an obturator 5001.

In some embodiments, a distal portion of an obturator 5001 is insertable into the lumen 4903 of said insertable member 4901. In some embodiments, the outer diameter cross-section of the insertable member 4901 comprises a diameter that is larger than the diameter comprised by the internal diameter cross-section of the unexpanded passage 1308 of an expandable cannula device 100.

The assembly of obturator 5001 and insertable member 4901 may be advanced into an unexpanded passage 1308 of an expandable cannula device 100. The insertion of the insertable member 4901 distally into the expandable cannula device 100, causes the plurality of elongate rigid members 2001 to move away from each other by sliding into the guide grooves 1802 of the first housing 1801 and creating an expanded passage 1309.

In this embodiment the elongate rigid members 2001 comprise an inner surface portion 2003 and the insertable member 4901 comprises a complimentary external surface 4906 that facilitates its insertion towards a distal portion and facilitates the transmission of forces in order to slide the plurality of elongate rigid members 2001 away from each other. In some embodiments, the complimentary surfaces comprise complimentary tapers In some embodiments, after the insertable member 4901 is delivered towards a distal position of the expandable cannula device 100, it is in contact and is held firmly by the elongate rigid members 2001, especially if the expandable cannula device 100 is expanded inside a subject's tissue, where the tissue may also add a compressive force onto the external surface of the elongate rigid members 2001. Since the insertable member 4901 is held firmly, the obturator 5001 can be removed from the expandable cannula device 100, which leaves the expanded expandable cannula device 100 having a continuous lumen from the first housing 1801 down towards the expanded passage 1309 defined by the plurality of expanded elongate rigid members 2001.

In some embodiments (not shown), the short insertable member 4901 and the obturator 5001 may be coupled by threads or by reversible coupling mechanisms that are known to the experienced in the mechanical arts, such as spring-loaded pins.

Similarly, in some embodiments (not shown), the external surface of the short insertable member 4901 may be coupled to the internal surface of the elongate rigid members 2001 by threaded mechanism or by other reversible coupling mechanism that are known to the experienced in the mechanical arts.

In some embodiment, the obturator 5001 comprises a hollow shaft, wherein said shaft is terminated distally by the obturator tip 5004. In some embodiments, the obturator 5001 is made from optically transparent or translucent material. In some embodiments, a medical imaging probe, such as a laparoscope may be inserted into the said hollow shaft of the obturator but may not protrude past the tip 5004.

With reference to FIGS. 104-111: insertable member into the passage.

In some embodiments, the expandable cannula device 100 further comprises an insertable member 4901 configured to be inserted into the passage of the expandable cannula device 100 that is defined by the plurality of elongate rigid members 2001. In some embodiments, the insertable member 4901 is inserted into an unexpanded passage 1308 or an expanded passage 1309.

With reference to FIGS. 104-111: insertable member causes expansion and has a lumen.

In some embodiments, the insertion of the insertable member 4901 into the passage of the expandable cannula device 100 causes the plurality of elongate rigid members 2001 to move away from each other if a cross-section of the unexpanded passage 1308 is smaller than a cross-section of the insertable member 4901.

In some embodiments, the insertable member 4901 defines a lumen 4903. In some embodiments, the lumen is generally cylindrical.

Figure 114:
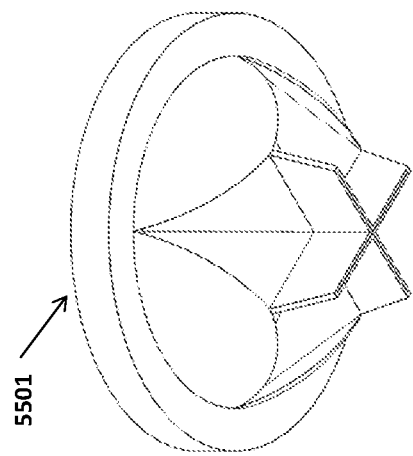
FIG. 114 is an isometric view of an example embodiment of a one-way fluid valve.
Figure 113:
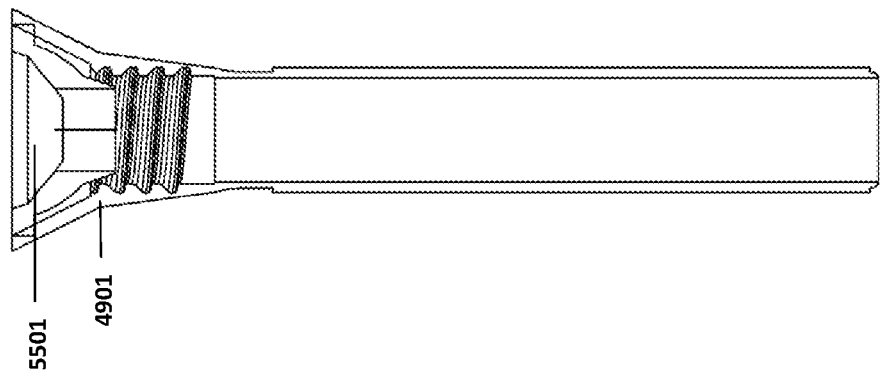
FIG. 113 is a cross-sectional side view of the embodiment of FIG. 112.
Figure 112:
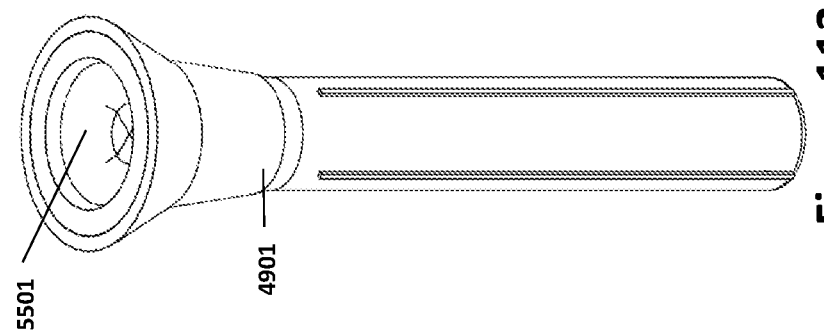
FIG. 112 is an isometric view of an example embodiment of an insertable member comprising a one-way fluid valve in its proximal region.
Figure 118:
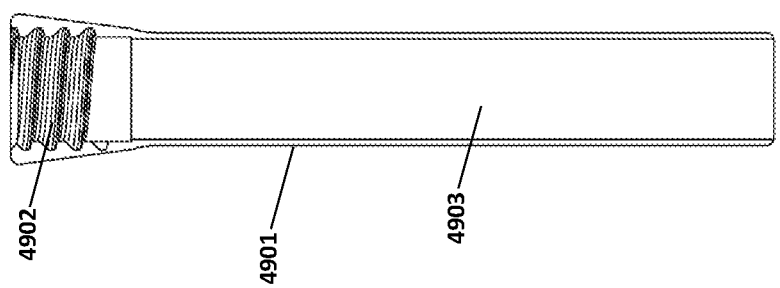
FIG. 118 is a cross-sectional side view of the embodiment shown in FIG. 117.
Figure 117:
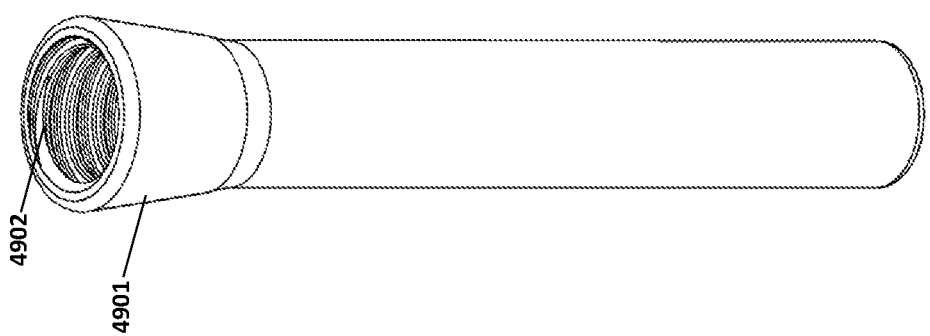
FIG. 117 is an isometric view of an embodiment of an insertable member with internal threaded features.

With reference to FIGS. 112-114: the insertable member with valves.

This embodiment shows an insertable member 4901 comprising at least one valve disposed in its lumen 4903. In some embodiments, the valve comprises a one-way fluid valve 5501

In some embodiments, the least one one-way fluid valve 5501 is disposed at a proximal region of the insertable member 4901. Said one-way fluid valve 5501 function is to prevent backflow of injected fluids from a proximal region of the insertable member towards the distal region of the insertable member.

Many examples of one-way fluid valves 5501 are known to the skilled in the art and can be used here.

With reference to FIGS. 115-118: insertable member with obturator.

The expandable cannula device 100 further comprises a first obturator 5001 insertable through the lumen 4903 of the insertable member 4901. In some embodiments, the first obturator 5001 and the lumen 4903 cooperatively define a threaded fit such that the first obturator 5001 is capable of threaded movement relative to the insertable member 4901.

In some embodiments, the insertable member 4901 comprises a lumen 4903. In some embodiments, there may be internal threaded features 4902 on the internal surface of the insertable member 4901. In some embodiments, an obturator 5001 maybe inserted through the lumen 4903 of the insertable member 4901 and the obturator-insertable member assembly can be inserted into the passage of the expandable cannula device 100 The obturator 5001 comprises a proximal handle 5002 that can be manipulated by the user. In some embodiments, the obturator 5001 may comprise threaded features 5003 on the external surface of the obturator that allow the obturator 5001 to become threadedly coupled to the insertable member 4901.

In some embodiments, the obturator 5001 comprises a distal tip 5004. In some embodiments, the distal tip 5004 may be blunt. In some embodiments, the obturator may comprise a tapered distal tip 5005. In some embodiments, the tapered distal tip 5005, may be sharp.

With reference to FIGS. 119-122:

In some embodiments, the insertable member 4901 may be inserted through the expanded passage 1309 of an expandable cannula device 100. In some embodiments, the insertable member 4901 may be inserted through the unexpanded passage 1308 of an expandable cannula device 100. In some embodiments, the lumen 4903 of the insertable member 4901 may comprise a larger cross section than cross section of an unexpanded passage 1308. Thus, by inserting said insertable member 4901 into the unexpanded passage 1308, the elongate rigid members 1301 move away from each other and create an expanded passage 1309 that has a diameter at least equivalent to the outer diameter of the insertable member 4901 that is in contact with the internal surface of the plurality of elongate rigid members 1301. In some embodiments, the size of the expanded passage 1309 can be selected by selecting an insertable member 4901 of a specific outer diameter.

In some embodiments, the obturator 5001 may be coupled to the insertable member 4901, wherein the assembly of both the obturator 5001 and insertable member 4901 are inserted into the passage of the expandable cannula device 100, such that when the insertable member 4901 is in the passage, the obturator 5001 may be removed, such that the lumen 4903 of the insertable member 4901 creates a passage that is concentric with the passage of the expandable cannula device 100.

With reference to FIGS. 123-126: non-smooth features of the insertable member.

This embodiment shows an insertable member 4901 with a plurality of frictional surface reliefs (non-smooth features 5601) disposed onto the exterior surface of the insertable member 4901. In some embodiments, said non-smooth features 5601 create better retention and stability of expandable cannula device 100 in the tissue and prevent accidental dislodgment of the expandable cannula device 100 outside of the tissue.

In some embodiments the non-smooth features 5601 comprises ratchet features. In some embodiments (not shown), the non-smooth features 5601 may comprise pattern of pins, threaded features, and ribbed walls.

In some other embodiments (not shown), the non-smooth features 5601 are housed within the walls of the insertable member 4901 and may be ejected outwards by an actuation mechanism. The actuation mechanism may be reversible such that the non-smooth features 5601 are retracted back into the walls of the insertable member 4901.

In some embodiments, said actuation mechanism comprises obturator 5001 insertion distally into the lumen 4903 of the insertable member 4901. In some embodiments (not shown), the actuation mechanism comprises obturator 5001 removal from a distal position within the lumen 4903 of the insertable member 4901 towards a proximal region. In some embodiments (not shown), the actuation mechanism comprises rotation of an obturator 5001 in the lumen 4903 of the insertable member 4901.

In some embodiments (not shown), the actuation mechanism comprises rotation the insertable member 4901 about the central axis of the expandable cannula device 100. In some embodiments, the actuation mechanism comprises insertion of an additional insertable member 4901 which does not have non-smooth features 5601 inside the lumen of the first insertable member 4901 that comprises the non-smooth features 5601.

In some embodiments, the movable non-smooth surface features and mechanisms for moving them may be utilized in existing cannulas or trocars (not shown).

Figure 116:
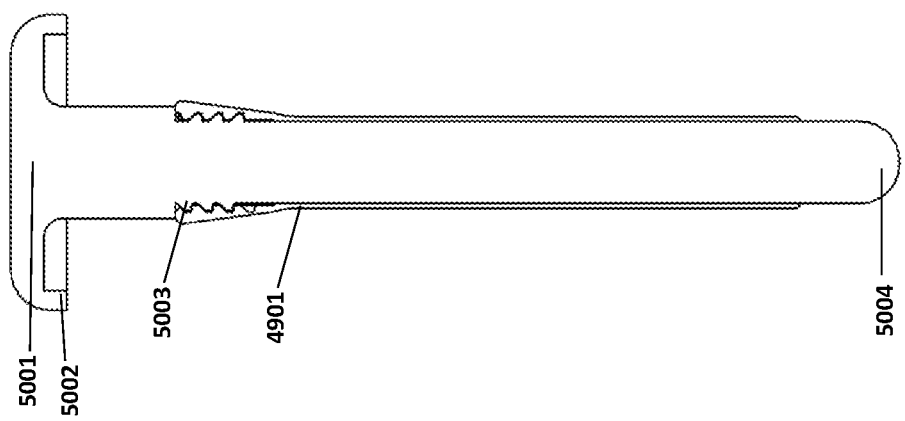
FIG. 116 is a cross-sectional side view of the embodiments shown in FIG. 115.
Figure 115:
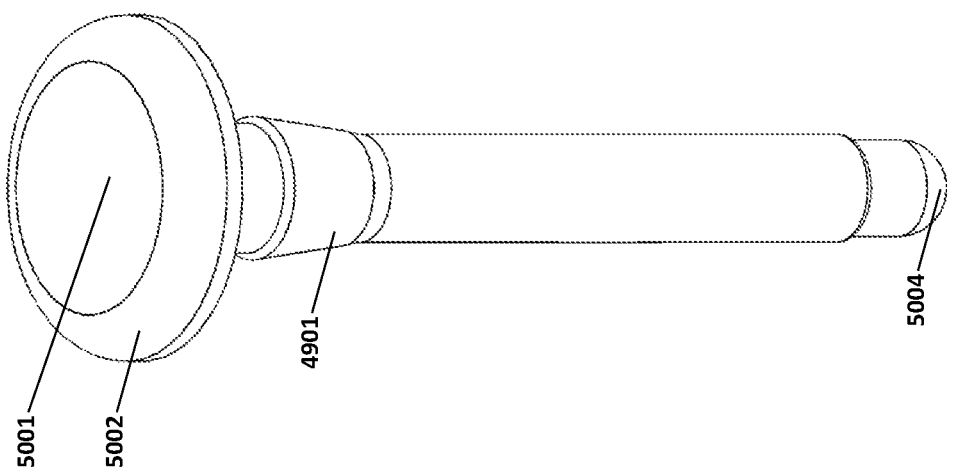
FIG. 115 is an isometric view of an example embodiment of an obturator threadedly coupled to an insertable member.
Figure 126:
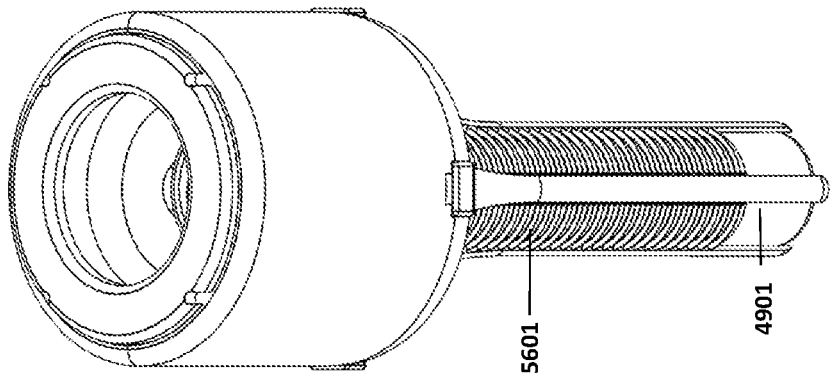
Figure 125:
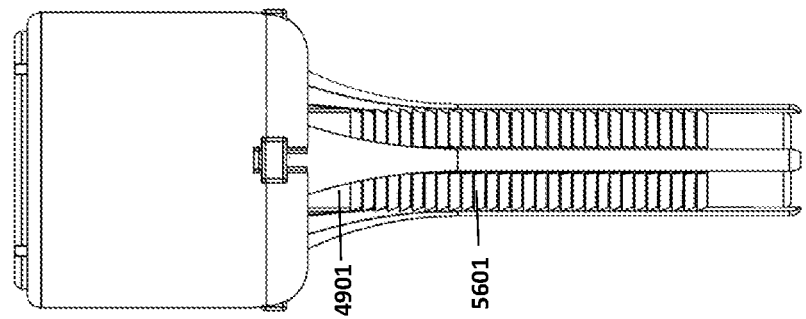
Figure 124:
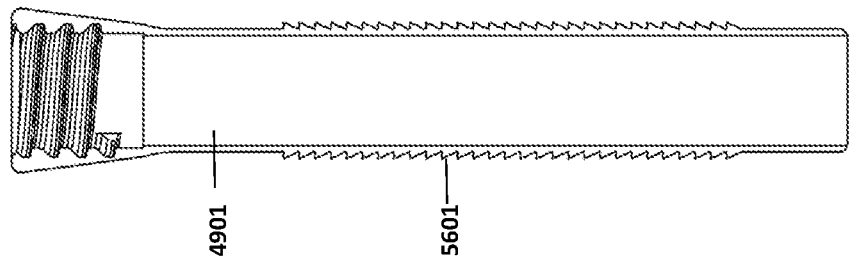
FIG. 124 is a cross-sectional side view of the embodiment of an insertable member as shown in FIG. 123.
Figure 123:
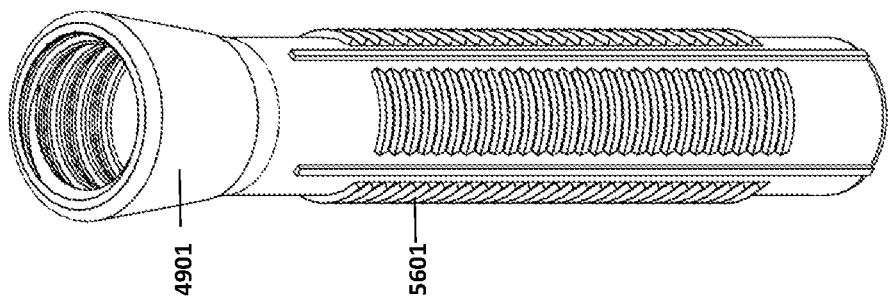
FIG. 123 is an isometric view of an example embodiment of an insertable member comprising non-smooth features on its external surface.

With reference to FIGS. 115-116:

In some embodiments, the first obturator 5001 comprises a distal tip 5004 that is not sharp (blunt).

With reference to FIGS. 115-121: insertable member has circular cross section.

In some embodiments, the insertable member 4901 comprises a generally circular or oval cross-section that transverses a length of the insertable member 4901.

With reference to FIGS. 127-130: threaded connection, handle, complimentary shapes.

In a different embodiment, the insertable member 4901, has at least one handle 4904. In some embodiments, the handle 4904 may be used to push the insertable member 4901 into a distal part of the expandable cannula device 100. In some embodiments, the handle 4904 may be used to apply a rotational or pushing motion or a combination of rotation and pushing motions onto the insertable member 4901.

In some embodiments (not shown), the insertable member 4901 has an external surface that is complimentary to the internal surface of at least a portion of the first housing. In some embodiments, the complimentary surfaces comprise complimentary tapers.

In some embodiments (not shown), the insertable member 4901 and the first housing cooperatively define a threaded connection such that the insertable member 4901 may threadedly move relative to the first housing when the insertable member 4901 is rotated.

In some embodiment (with reference to FIG. 108), the insertable member 4901 has an external surface 4906 that is complimentary to the inner surface portion 2003 of some embodiments of the elongate rigid member 2001. In some embodiments, the complimentary surfaces comprise complimentary tapers.

In some embodiments, the insertable member 4901 may comprise external threaded features 4907 for being threadedly coupled and advanced distally into the first housing of some previous embodiments.

With reference to FIGS. 59-62:

In some embodiments, a first insertable member 4901 comprises an actuating member 1901 with a throughbore 1903; the throughbore 1903 further comprises an internal surface 4905 complimentary to a second insertable member 4901 that is insertable through the throughbore 1903, wherein the second insertable member 4901 comprises a portion with an external shape complimentary to the internal surface 4905 of the actuating member 1901. In some embodiments, the complimentary surfaces comprise complimentary tapers.

With reference to FIGS. 127-130:

In some embodiments, wherein the actuating member 1901 comprises a first insertable member 4901 with a first lumen 4903. In some embodiments, the first lumen 4903 comprises an internal surface 4905 complimentary to a second insertable member 4901 (not shown) that is insertable through the first 4903 lumen, wherein the second insertable member 4901 comprises an external shape complimentary to the internal surface 4905 of the first insertable member 4901. In some embodiments, the complimentary surfaces comprise complimentary tapers.

With reference to FIGS. 131-139: elongate rigid member/insertable member guidance mechanisms and angular rotation locks.

The expandable cannula device 100 of any of previous embodiments wherein the plurality of elongate rigid members 5101 and the insertable member 4901 cooperatively define a stopping mechanism for preventing or restricting movement of the insertable member 4901 beyond a predetermined position.

In some embodiments, the plurality of elongate rigid members 5101 and the insertable member 4901 cooperatively define a guidance mechanism for limiting an angular position of the insertable member 4901 relative to the plurality of elongate rigid members 5101.

In some embodiments, the guidance mechanism is configured to stop the insertable member 4901 from extending in the passage beyond a predetermined position.

In some embodiments, the guidance mechanism comprises at least one tongues and at least one groove between the insertable member 4901 and the plurality of elongate rigid ember 5101.

In some examples, the insertable member 4901 comprises at least one feature 4908 that is complimentary to feature 5102 on the internal surface of the elongate rigid members 5101. In some embodiments, the feature 4908 comprises a tongue and the feature 5102 comprises complimentary groove.

In some embodiments, the feature 5102 comprise a limited depth 5103 along the length of the elongate rigid member 5101, such that the insertable member 4901 may not be inserted past a more distal region into the expanded passage 1309 of the expandable cannula device 100.

In some embodiments, the features 4908 and features 5102 are reversed such that features 4908 comprise grooves and feature 5102 comprise complimentary tongues.

With reference to FIGS. 140-142: a spring-loaded insertable member mechanism.

In some embodiments, the expandable cannula further comprises a second biasing mechanism for biasing the insertable member 4901 toward the plurality of elongate rigid members 1301.

In some embodiments, the biasing mechanism causes an increase of an overlap between the insertable member 4901 and the elongate rigid members 1301, such that expansion of the elongate rigid members 1301 is effected.

In some embodiments, the insertion of an insertable member 4901 into the expanded passage 1309 of the expandable cannula device 100 may occur simultaneously while the expandable cannula device 100 is expanded, instead of having to insert said insertable member 4901 after the expandable cannula device 100 is expanded, thus saving time and making the process more streamlined for the user.

In some embodiments, an insertable member 4901 is housed within the throughbore 1103 of the first housing 1101 such that the insertable member 4901 is in a proximal region to the unexpanded passage 1308 that is defined by the plurality of elongate rigid members 1301. In some embodiments, the first housing 1101 further comprises a member 5201 attachable to the proximal surface region of the first housing 1101. In some embodiments, the member 5201 further comprises a central lumen. In this embodiment, the insertable member comprises at least one biasing member connected from insertable member 4901 to the member 5201. In some embodiments, the biasing member comprises a compression spring. The cross-section of the outer diameter of the insertable member 4901 is larger than the cross-section of the inner diameter of unexpanded passage 1308 of the expandable cannula, which prevents the insertable member 4901 from being able to advance into the unexpanded passage 1308 defined by the plurality of elongate rigid members 1301. This causes the at least one spring to become a compressed spring 5202 such that the insertable member remains proximal to the unexpanded passage 1308. When the unexpanded passage 1308 of the expandable cannula device 100 is expanded to an expanded passage 1309, such that the cross-sectional of the inner diameter of the expanded passage 1309 is at least equal or larger than the cross-section of the outer diameter of the insertable member 4901, the insertable member 4901 is inserted into the expanded passage 1309 by the at least one compressed spring 5202 releasing its potential energy and becoming an uncompressed spring 5203.

With reference to FIGS. 143-146: an insertable member with an expandable accordioned sleeve on its proximal side.

The insertable member 4901 further comprises a flexible sealing member, wherein the movement of the insertable member 4901 relative to the first housing causes the flexible sealing member to expand or retract.

In this embodiment the flexible sealing member with a central lumen is attached to the proximal part of the insertable member 4901, such that when the insertable member 4901 is in the first housing, the flexible sealing member is axially contracted 5401, and when the insertable member 4901 is inserted distally to cause the unexpanded passage 1308 of the expandable cannula device 100 to become an expanded passage 1309, the flexible sealing member becomes an axially expanded member 5402. In some embodiments, the axially expanded member 5402 creates a sealing mechanism against fluid leakage through expanded passage 1309 of the expandable cannula device 100.

In some embodiments, the flexible sealing member is made from a thin but difficult to stretch polymeric material, such as Polyether block amide (PEBAX). In some embodiments, it is made from nylon. In some embodiments, the flexible sealing member is made from hard material such as plastic or metals and is comprised from a plurality of hinged disks (not shown).

Insert Increases Stability of Passage:

With reference to the expandable cannula device 100 of any one of previous embodiments (such as in FIGS. 119-122), the insertion of the insertable member 4901 into the passage of the cannula enhances the stability and load-bearing capacity of the plurality of elongate rigid members 1301 that define said passage by comprising an additional load-bearing member along the inner surface and a portion of the length of the elongate rigid members 1301. In some embodiments, where the elongate rigid members 1301 are subject to external surface compressive pressure from the tissue, the additional load-bearing provided by the insertable member 4901 may prevent the elongate rigid members 1301 from bending towards the central axis of the expandable cannula device 100.

With reference to FIGS. 147-150: elongate rigid members having non-smooth features actuated by an insertable member.

In some embodiments of an expandable cannula device 100, the elongate rigid members 4701 comprise a plurality of frictional surface reliefs (non-smooth features) on its external surface.

In some embodiments, the non-smooth features comprise stability features 4801. In some embodiments, the stability features 4801 comprise patterns comprising at least one of ratchets, ribbed surfaces, threaded surfaces and pins.

In some embodiments, the stability features 4801 are reversibly movable away from the exterior surface of the at least one of the elongate rigid members 4701 via an actuation mechanism.

In some embodiments (not shown), the actuation mechanism comprises the insertion, or removal or rotation of an insertable member 4901 or of an obturator 5001 through the passage defined by the plurality of elongate rigid members 4701.

In some embodiments, the stability features 4801 are retractable. In some embodiments, the retractable features are disposed in a pattern of holes that traverse the cross section of the elongate rigid member 4701:

In some embodiments, the holes for stability features 4801 are situated at an angle relative to the long axis of the elongate rigid member 4701. In some embodiments, there is at least one stability feature 4801 in each hole.

In some embodiments, the stability features 4801 comprise a stopping feature 4802. In some embodiments, the stopping feature 4802 comprises an enlarged portion that is larger than the diameter of the hole to ensure that the stability feature 4801 does not pass entirely through the hole. In some embodiments, there is at least two stopping features 4802, an outer stopping feature 4802 disposed at a region further outward away from the outer surface of the elongate rigid member 4701, and the second, an inner stopping feature 4802 disposed at a region that is further inward from the inner surface of the elongate rigid member 4701.

In some embodiments, stopping features 4802 are made from substantially flexible material that may change its original shape when subject to particular mechanical pressure. In some configurations, the stopping features 4802 may be comprised of a fluid filled sac.

At the retracted position, all stability features 4801 are configured such that their distal stopping ends are flush with the outer surface of the elongate rigid member 4701. In some embodiments, the stability features 4801 are configured in an initial retracted position. In some embodiments, the stability features 4801 are pushed back towards the retracted position by the tissue. In some embodiments, the stability features 4801 are biased towards the retracted position. In some embodiments, the biasing mechanism comprises springs.

In some embodiments, the inner ends of the stability features 4801 comprise a circular pattern in the passage defined by the plurality of elongate rigid members 4701.

In some embodiments, the stability features 4801 are ejected in an outwards direction by an actuation mechanism. In some embodiments, the actuation mechanism comprises an actuation member.

In some embodiments, the actuation member comprises an insertable member 4901. In some embodiments, the actuation member comprises an obturator 5001. In some embodiments, the actuation member is an assembly comprised of both the insertable member 4901 and the obturator 5001.

In some embodiments, the insertion of an actuation member from a proximal point towards a distal point through the unexpanded passage 1308 or expanded passage 1309) defined by the plurality of elongate rigid members 4701, causes the stability features 4801 to be ejected outwards. In some embodiments, the removal of an actuation member causes the stability features 4801 to become retracted.

In some embodiments, where the holes are angled in direction that is defined from inner surface distal point of an elongate rigid member 4701 towards an outer surface proximal point of the same elongate rigid member 4701.

When an obturator 5001 and an insertable member 4901 are inserted into the cavity the tip of the obturator 5001 contacts the inner stopping feature 4802 of the stability feature 4801. The insertion force of the obturator pushes the stopping parts out of the central cavity and towards the holes in which the members are disposed. The stability features 4801 are pushed up at an angle through the angled holes. The obturator is removed from the cavity, and the stability features are held in this deployed position by the remaining insertable member 4901.

When insertable member 4901 is removed, the pressure against the inner stopping feature 4802 is also removed. In some configuration gravity, or external tissue pressure or a biasing mechanism may cause the stability features 4801 to slide back through the angled holes and come to the retracted position again In some embodiments (not shown), the movement of an actuation member from distal portion of the expandable cannula device 100 towards a proximal portion of the cannula causes the ejection of the stability features 4801. In some embodiments the opposite movement of said actuation member causes the retraction of said stability features 4801.

In some embodiments (not shown), the rotation of an actuation member about the central axis of the expandable cannula device 100 in a first direction causes the ejection of the stability features 4801. In some embodiments, the rotation of said actuation member about central axis of the expandable cannula in an opposite direction of first direction causes the ejected stability features 4801 to become retracted.

With reference to FIGS. 59-62, and FIGS. 119-122: insertable member creates a seal.

In some embodiments, the insertable member 4901 cooperates with, for example, the plurality of elongate rigid members 2001, or 1201, or 4701 to create a seal between each adjacent elongate rigid members 2001, or 1201, or 4701, when the insertable member 4901 is inserted into the expanded passage 1309.

Insert has complimentary shape to the struts:

In some embodiment (with reference to FIG. 108), the insertable member 4901 has an external surface 4906 that is complimentary to the inner surface portion 2003 of some embodiments of the elongate rigid member 2001. In some embodiments, the complimentary surfaces comprise complimentary tapers. In some embodiments, the external surface 4906 is frustoconical. In some embodiments (not shown), the external surface 4906 is located on a proximal region of the insertable member 4901.

Without the Actuation of an Insert:

In some embodiments of an expandable cannula device 100, the elongate rigid members 4701 comprise a plurality of non-smooth features on its external surface.

In some embodiments, the non-smooth features comprise stability features 4801. In some embodiments, the stability features stability features 4801 comprise patterns comprising at least one of ratchets, ribbed surfaces, threaded surfaces and pins.

In some embodiments, the stability features 4801 are move away from the exterior surface of the at least one of the elongate rigid members 4701 when the plurality of elongate rigid members when the plurality of elongate rigid members 4701 define an expanded passage 1309. In some embodiments, the stability features 4801 retract when the plurality of elongate rigid members define an unexpanded passage 1308.

Balloon at the distal end of the struts, inflatable:

In some embodiments of the expandable cannula (not shown), at least one inflatable balloon is disposed at an end, away from the housing(s), of at least one of the plurality of elongate rigid members 5101. In some embodiments, the inflatable balloon is configured to be inflated after the expandable cannula device 100 is inserted into a subject.

In some embodiments (not shown), each of the elongate rigid members 5101 comprise an inflatable balloon. In some embodiments, the inflatable balloon is disposed near the distal end of the elongate rigid members 5101.

In some embodiments, the each of the inflatable balloons are connected in a parallel configuration to an inflation port that is disposed on the proximal part of the expandable cannula device 100.

In some embodiments, the expandable cannula device 100 is inserted into a subject's tissue while the plurality of inflatable balloons are uninflated, and after the distal ends of the elongate rigid members 5101 have penetrated the tissue, the inflatable balloons are inflated by injecting fluid through the inflation ports. In some embodiments, the inflatable balloons may be inflated when the expandable cannula device 100 is unexpanded. In some embodiments, the inflatable balloons may be inflated after the expandable cannula device 100 is expanded in the tissue.

The inflated balloons prevent accidental retrieval or dislodgement of the expandable cannula device 100. The inflated balloons may be deflated by the user through the inflation port, and the cannula may be removed from the subject's tissue.

In some embodiments, the balloons are made from nylon or PEBAX.

In some embodiments, the inflation fluid may be gaseous or liquid.

In some embodiments (not shown), at least one proximal slider are disposed on the proximal part of the plurality of elongate rigid members 5101, such that the proximal slider is brought distally to sandwich the tissue between the proximal slider and the inflated inflatable balloons.

With reference to FIGS. 26-42: external surface of elongate rigid members are tapered.

In some embodiments, a portion of each of the elongate rigid members 1301 defines an outer surface taper 1304 extending from the first housing 1101.

Figure 28:
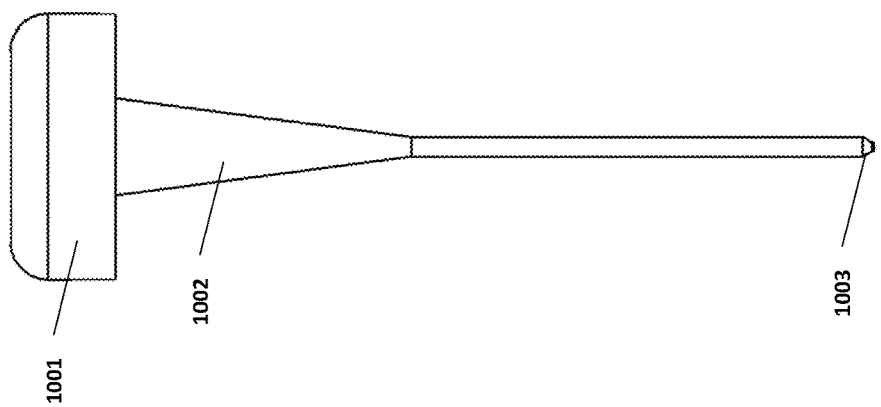
FIG. 28 is side view of the obturator depicted in the example embodiment shown in FIGS. 26-27.
Figure 27:
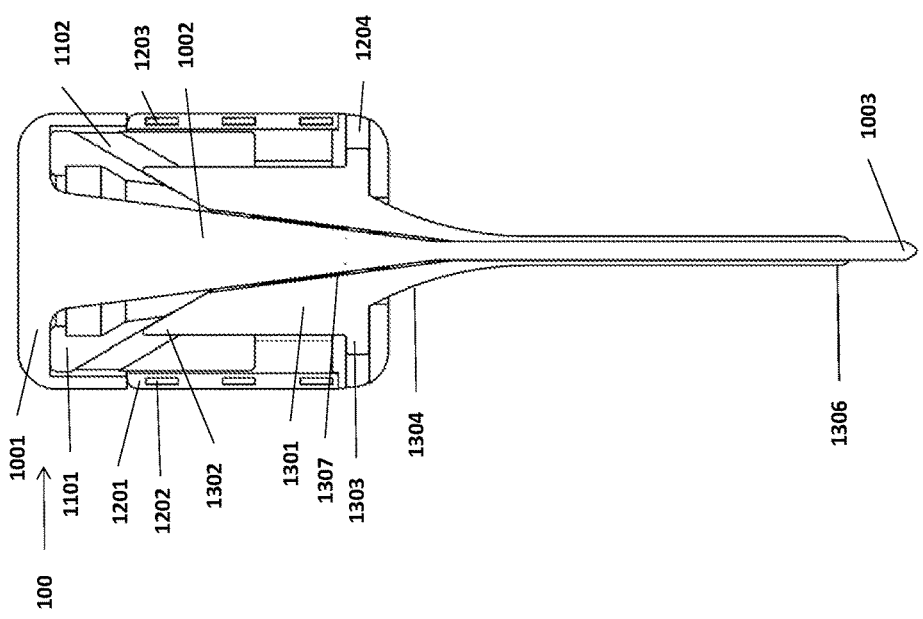
FIG. 27 is a cross sectional view of example embodiment of FIG. 26, showing internal mechanism of the expandable cannula.
Figure 26:
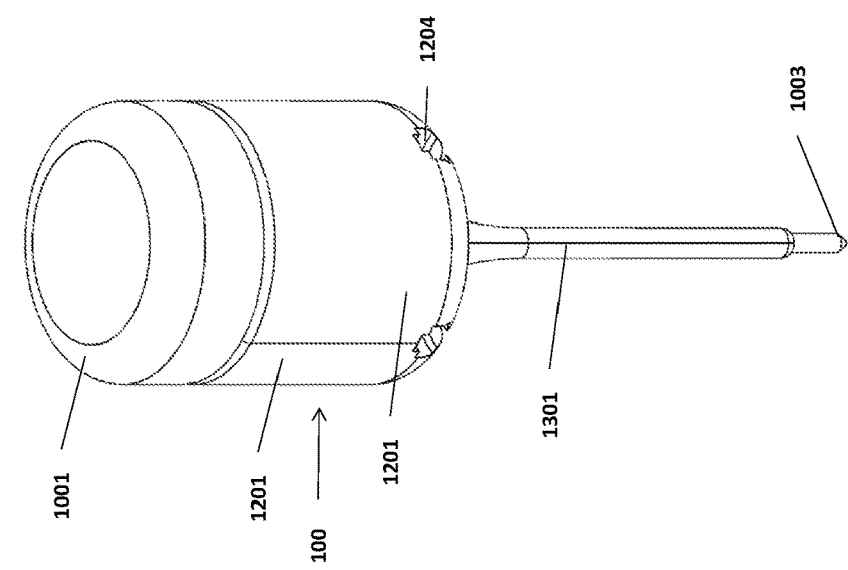
FIG. 26 is an isomeric view of an expandable cannula device with an obturator inserted through said device's passage.
Figure 31:
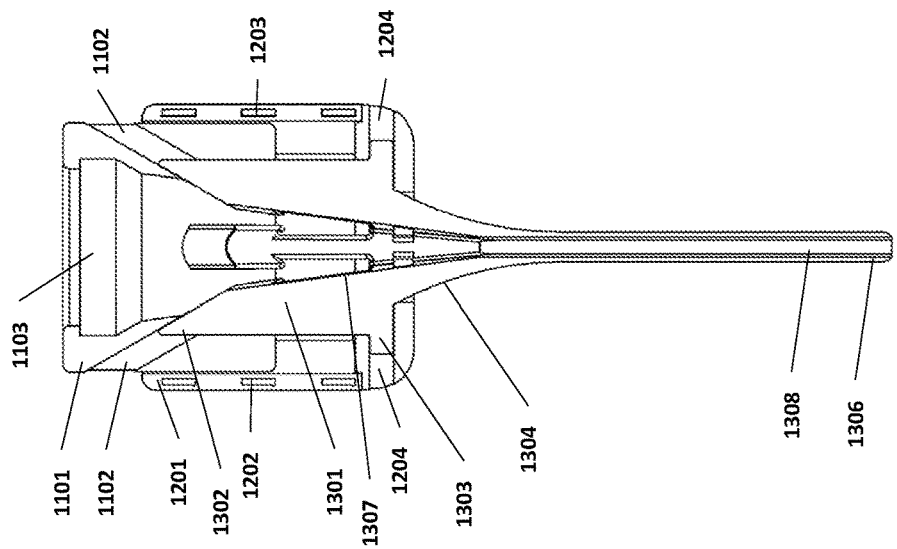
FIG. 31 is a cross-sectional view of example embodiment shown in FIG. 30.
Figure 30:
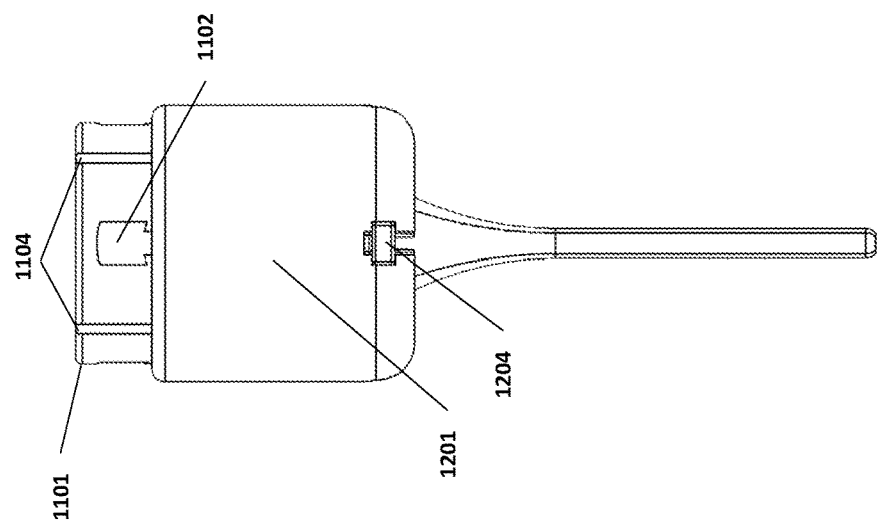
FIG. 30 is a side view of example embodiment shown in FIG. 29.
Figure 29:
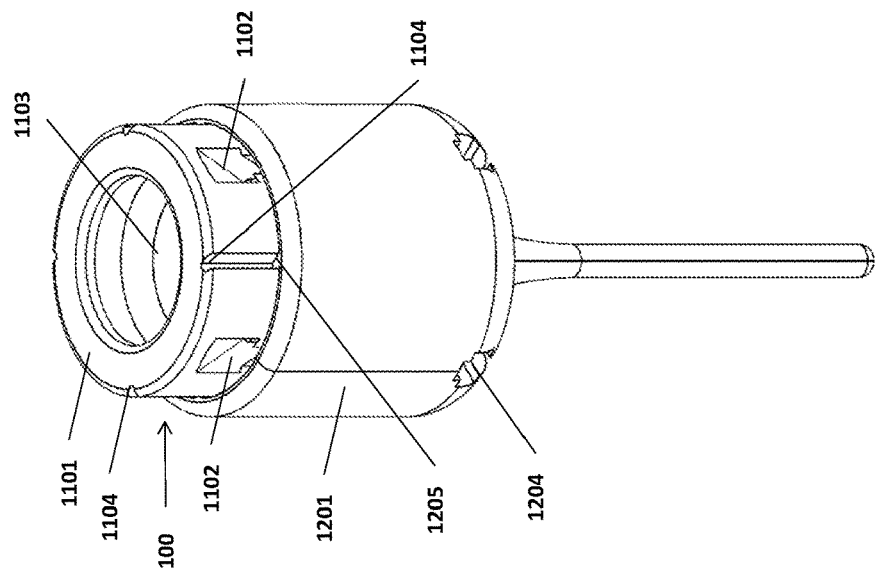
FIG. 29 is an isomeric view of an expandable cannula device embodiment comprising two housings and elongate rigid members, at an unexpanded state, wherein the second housing is farther away from the first housing and the elongate rigid members comprise an unexpanded passage of the cannula.
Figure 34:
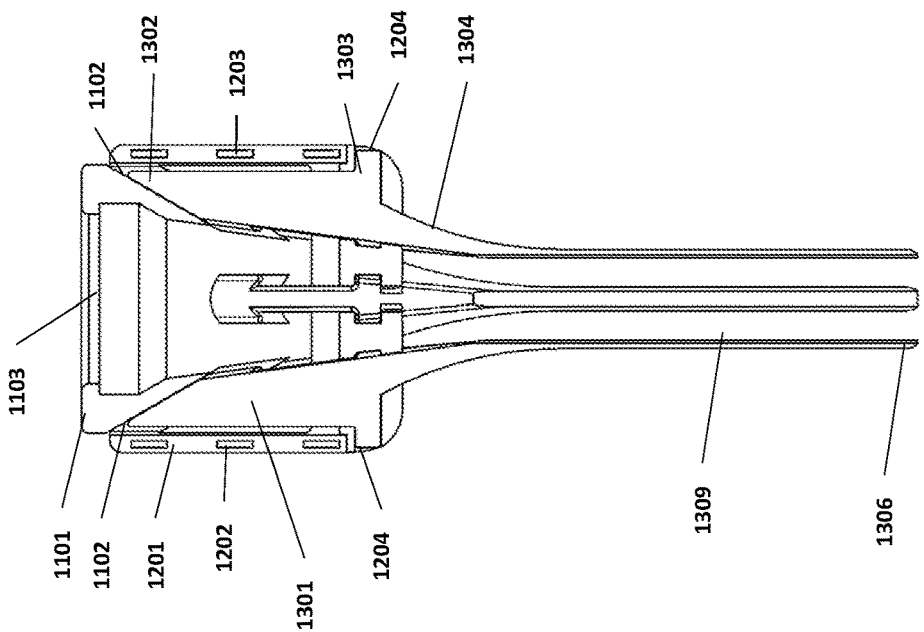
FIG. 34 is a cross-sectional view of example embodiment shown in FIG. 33.
Figure 33:
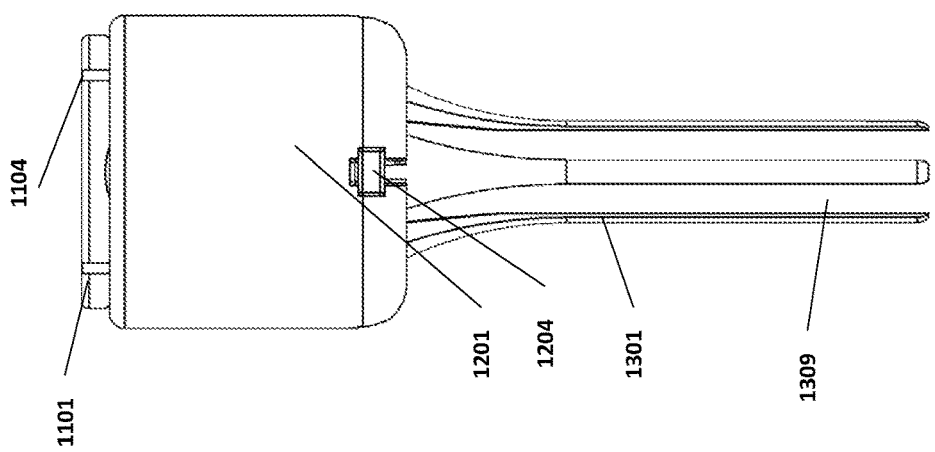
FIG. 33 is a side view of example embodiment shown in FIG. 32.
Figure 32:
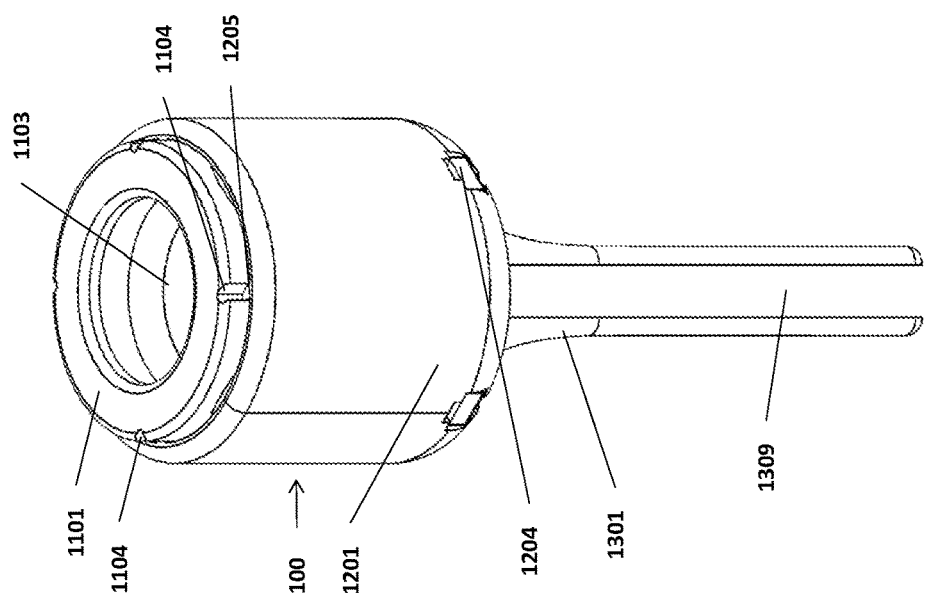
FIG. 32 is an isometric view of an expandable cannula device embodiment shown in FIGS. 29-31, at an expanded state, wherein the second housing is moved proximally closer towards the first housing causing the elongate rigid members to move away from each and comprise an expanded passage of the cannula.
Figure 37:
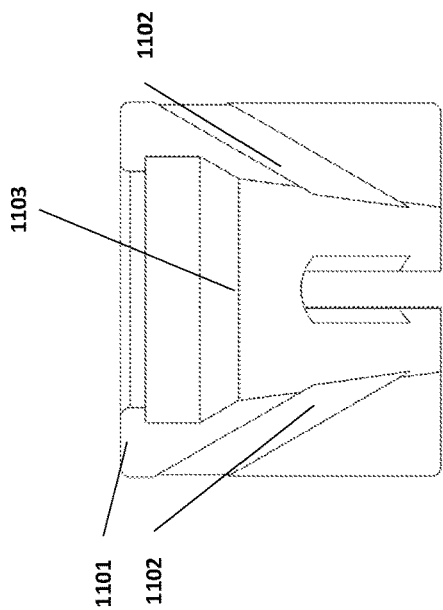
FIG. 37 is a cross-sectional view of example embodiment shown in FIG. 36.
Figure 36:
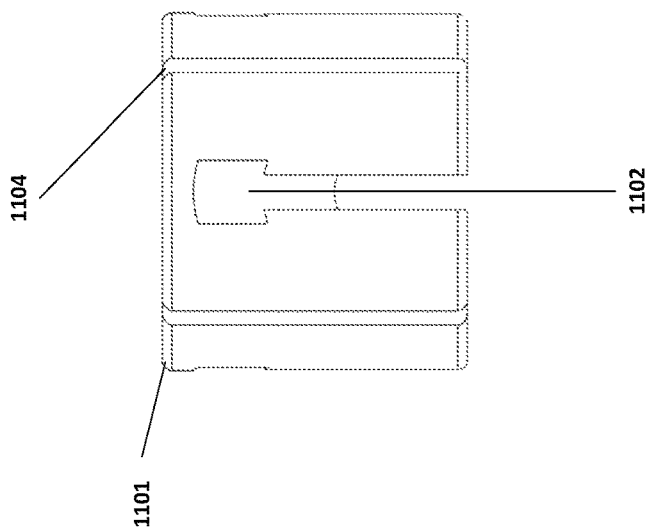
FIG. 36 is a side view of example embodiment shown in FIG. 35.
Figure 35:
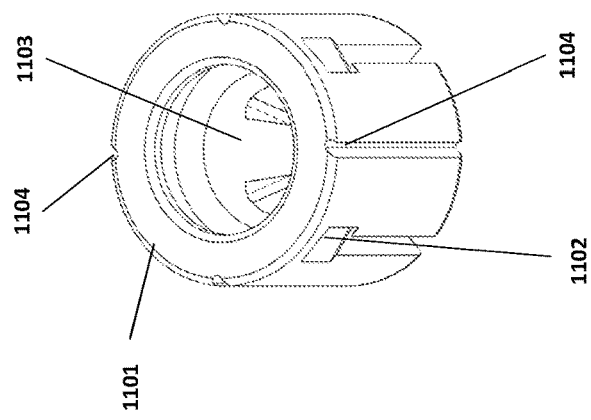
FIG. 35 is an isometric view of the first housing embodiment shown in FIGS. 26-34.
Figure 40:
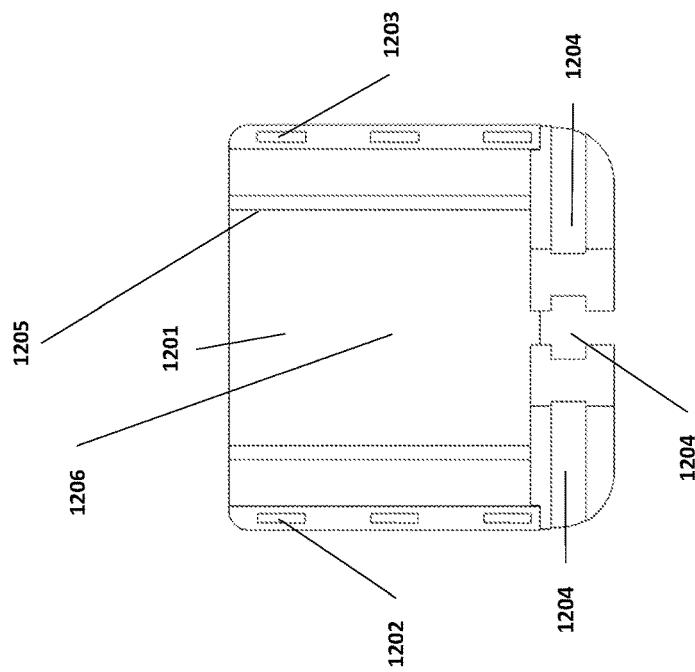
FIG. 40 is a cross-sectional view of example embodiment shown in FIG. 39.
Figure 39:
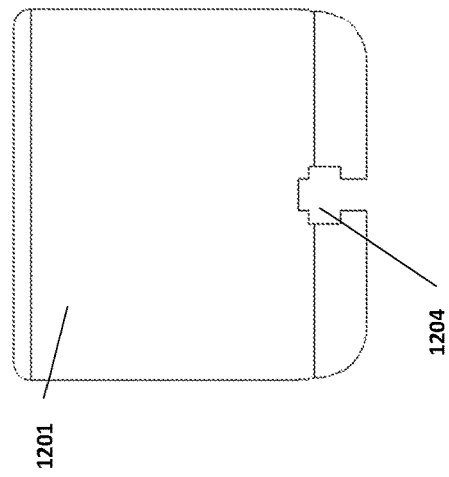
FIG. 39 is a side view of example embodiment shown in FIG. 38.
Figure 38:
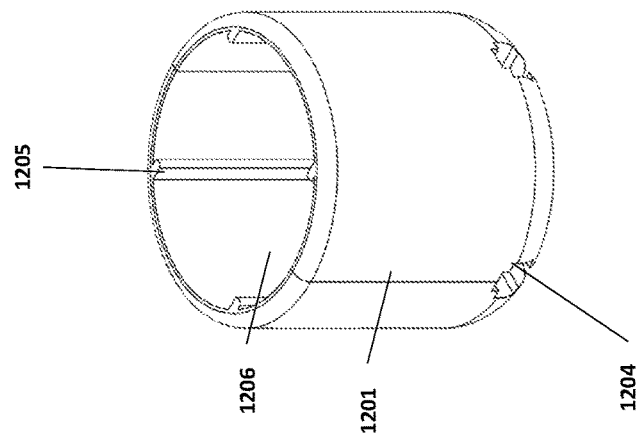
FIG. 38 is an isometric view of the second housing embodiment shown in FIGS. 26-34.
Figure 42:
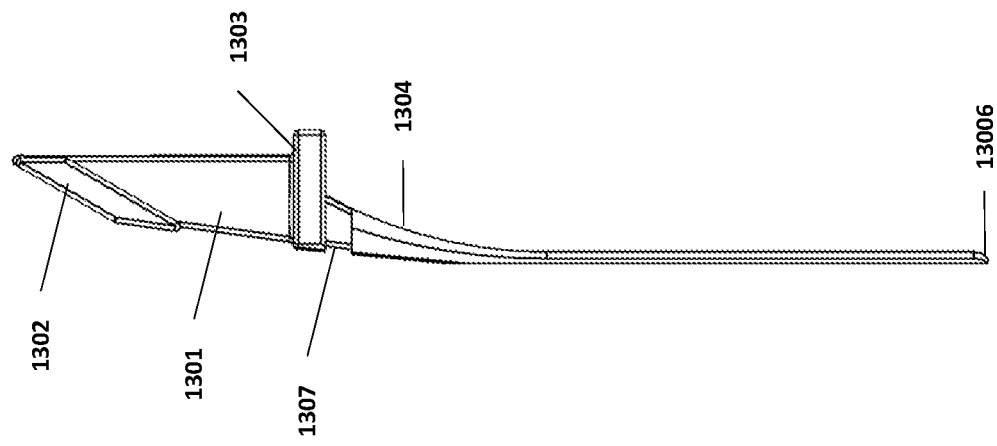
FIG. 42 is a side view of example embodiment shown in FIG. 41.
Figure 41:
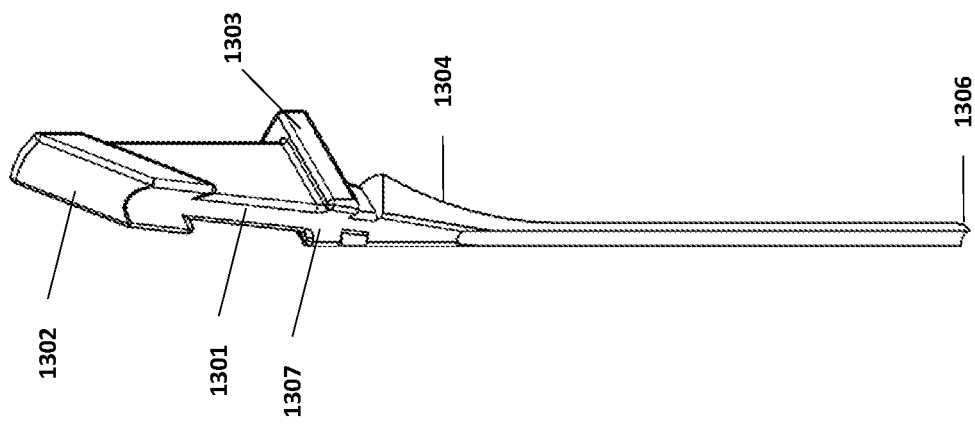
FIG. 41 is an isometric view of an example embodiment of one of the plurality of elongate rigid members in FIGS. 26-34.
Figure 48:
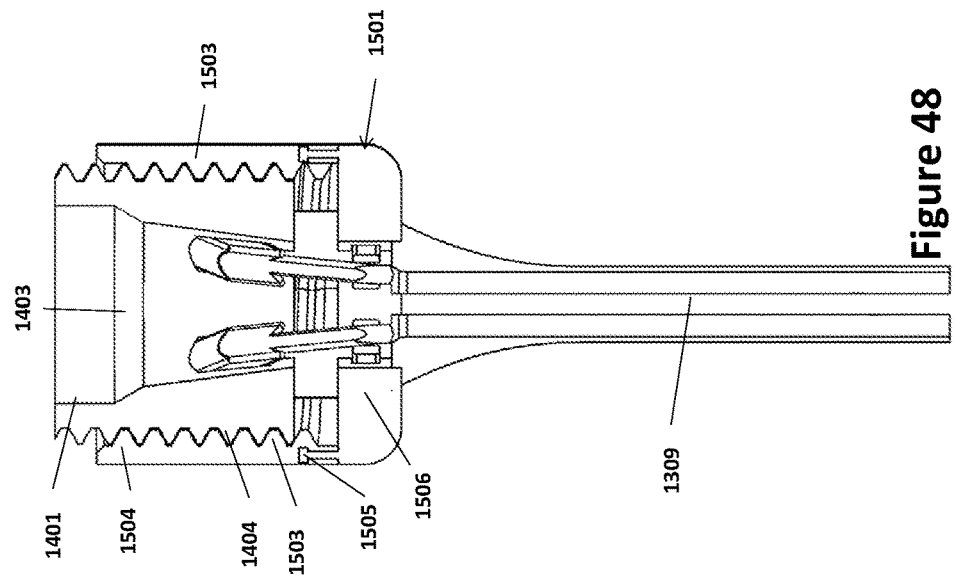
FIG. 48 is a cross-sectional view of example embodiment shown in FIG. 47.
Figure 47:
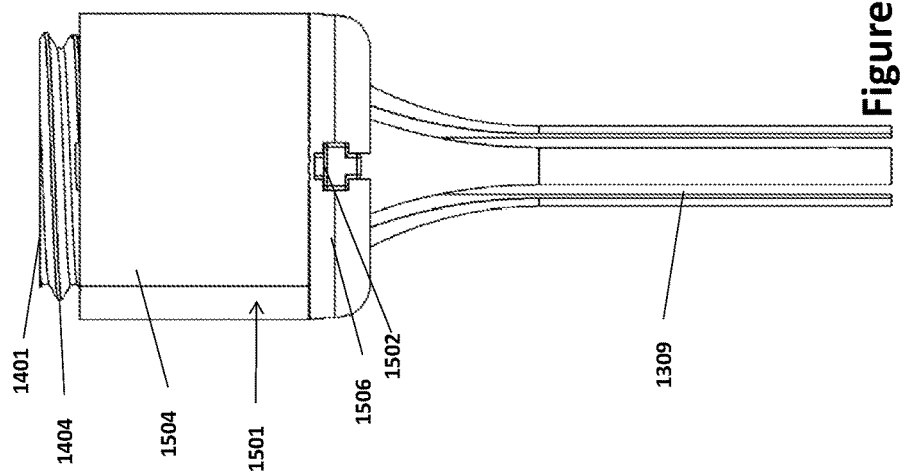
FIG. 47 is a side view of example embodiment shown in FIG. 46.
Figure 46:
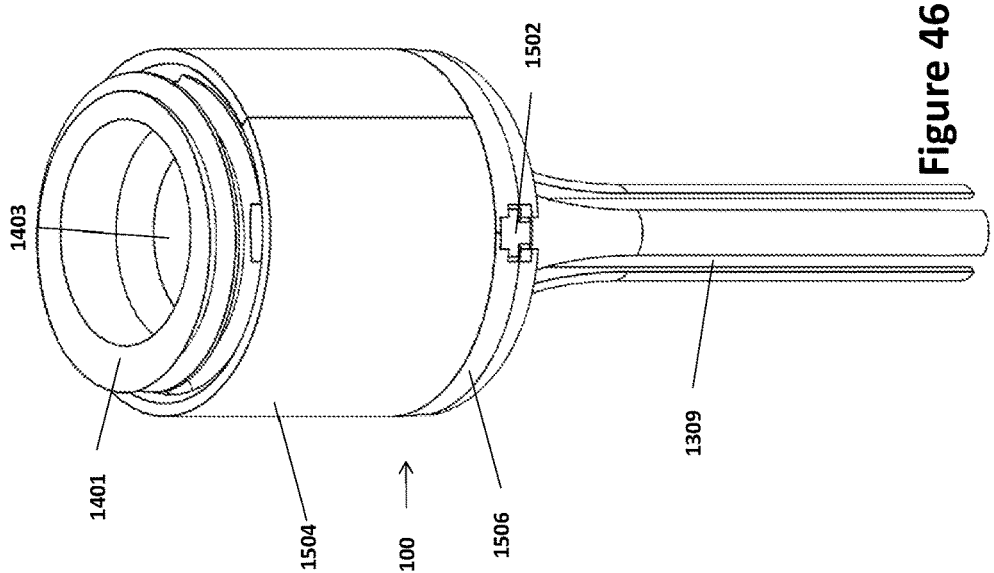
FIG. 46 is an isometric view of the expandable cannula device embodiment shown in FIGS. 43-45, at an expanded state, wherein the second housing is moved proximally closer to the first housing, causing the elongate rigid members to move away from each other and comprise an expanded passage.
Figure 55:
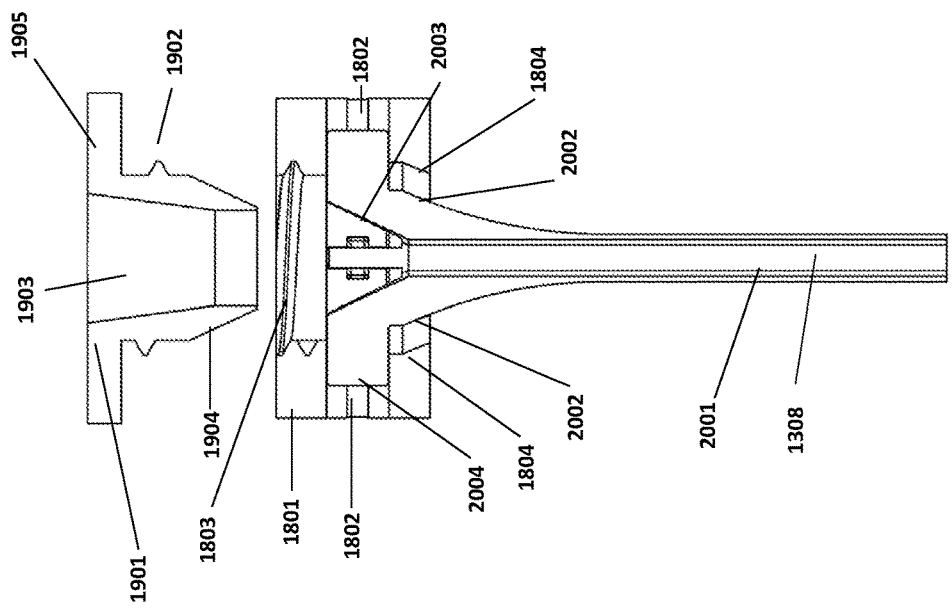
FIG. 55 is a cross sectional view of example embodiment shown in FIG. 54.
Figure 54:
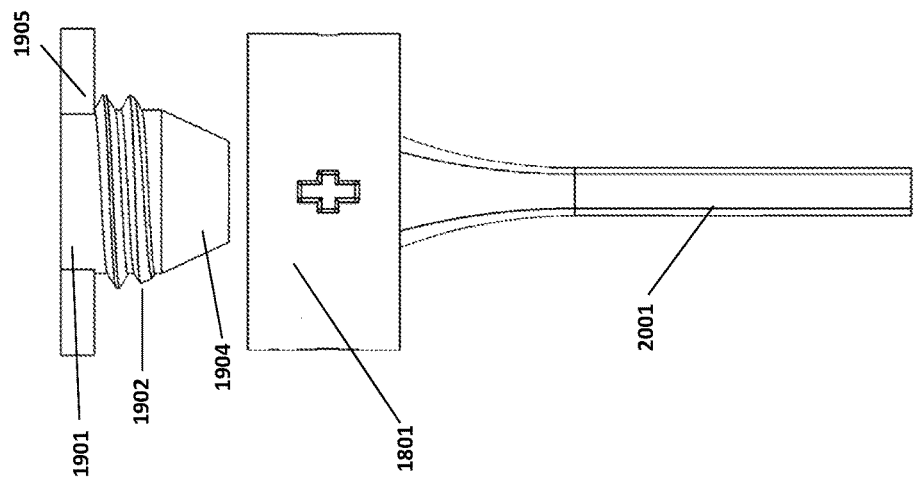
FIG. 54 is a side view of example embodiment shown in FIG. 53.
Figure 53:
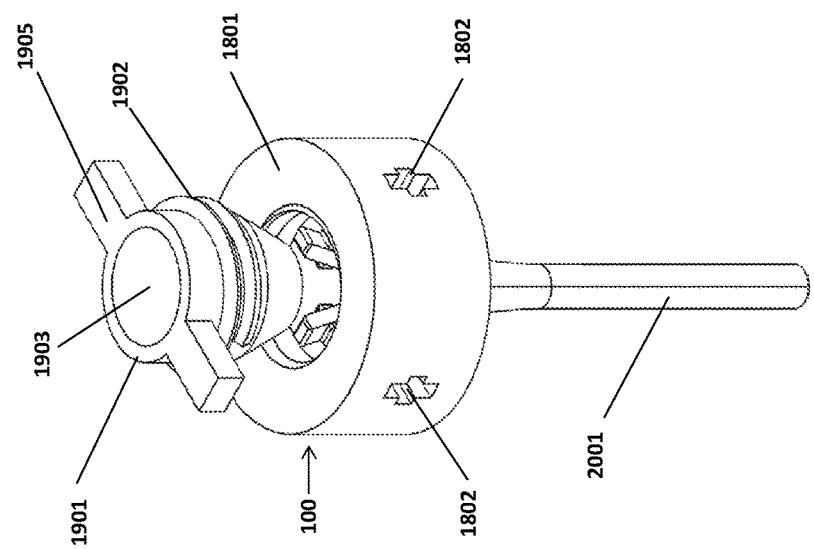
FIG. 53 is an isometric view of an embodiment of an expandable cannula device, comprising an actuation member shown in a position proximal to the first housing of an unexpanded configuration of the expandable cannula device embodiment.
Figure 64:
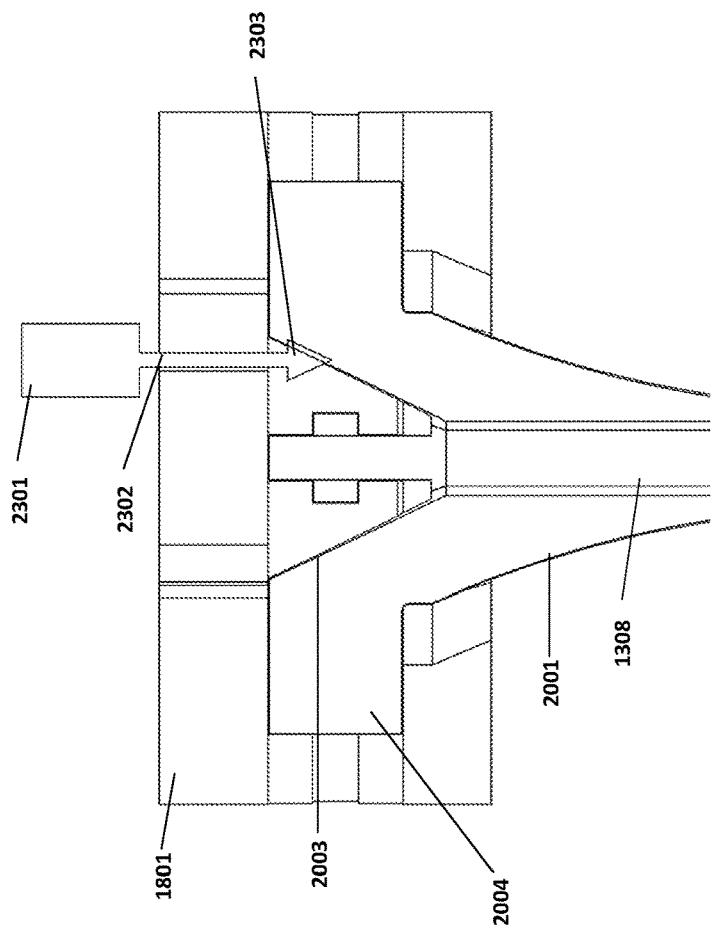
FIG. 64 is a cross-sectional side of view of the example embodiment shown in FIG. 63.
Figure 63:
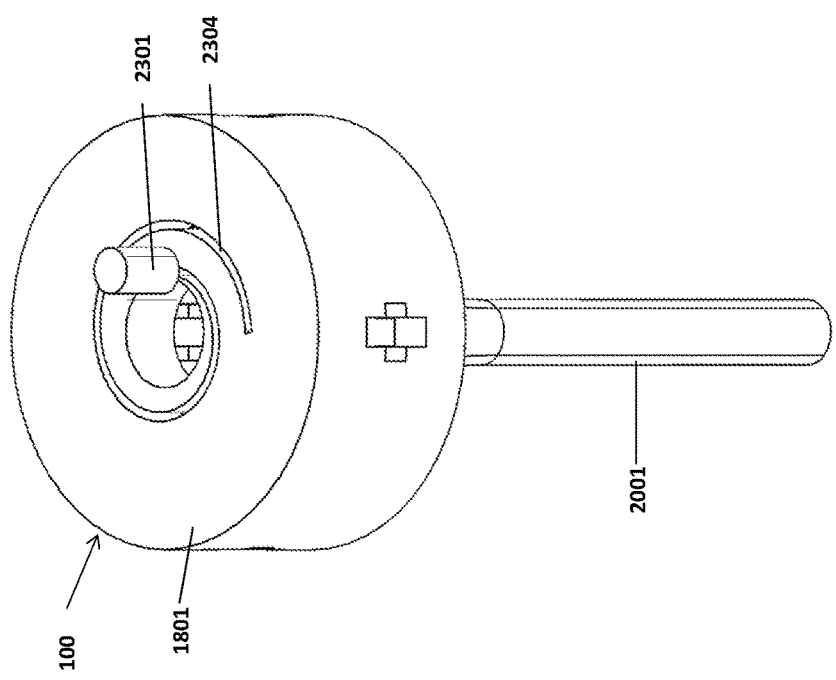
FIG. 63 is an isometric view of an expandable cannula device embodiment, at an unexpanded state, where a pin is located at a radially close position to the central axis of the device, where expansion of the elongate rigid members is effected by movement of the pin along a spiral track in the first housing.
Figure 66:
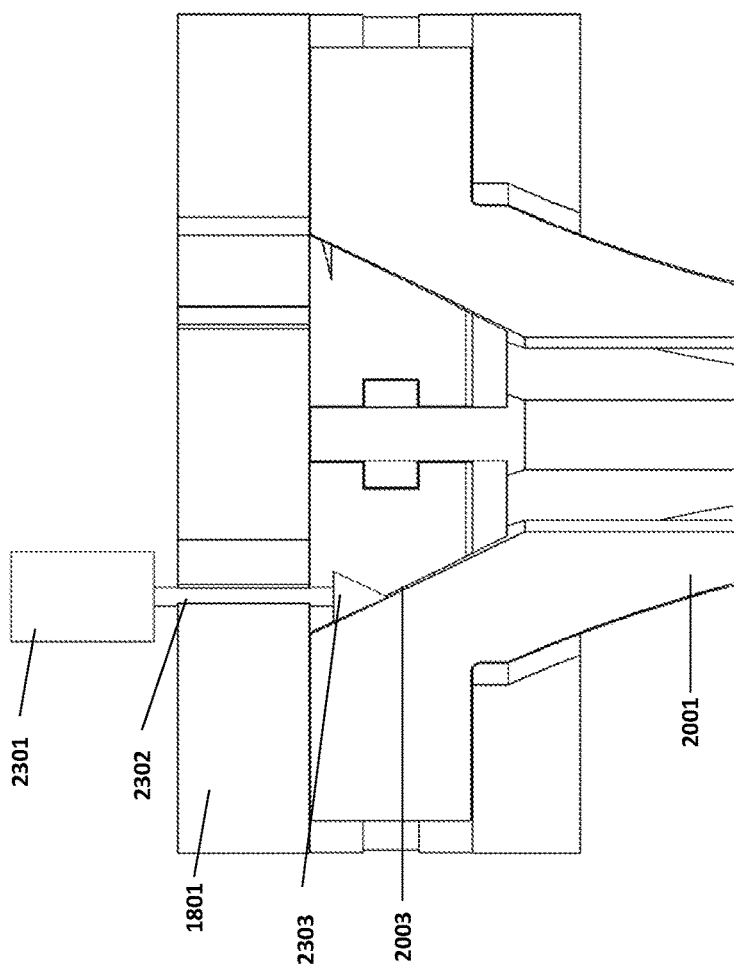
FIG. 66 is a cross-sectional side view of the example embodiment shown in FIG. 65.
Figure 65:
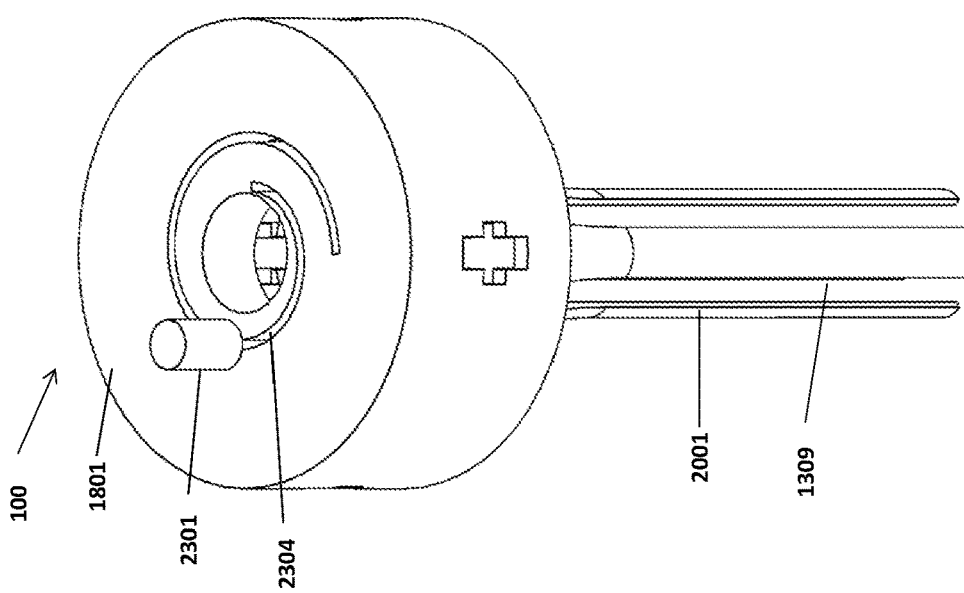
FIG. 65 is an isometric view of example embodiments of FIGS. 63-64, at an expanded state, where the pin is moved to a radially further away point along the spiral track of the first housing
Figure 68:
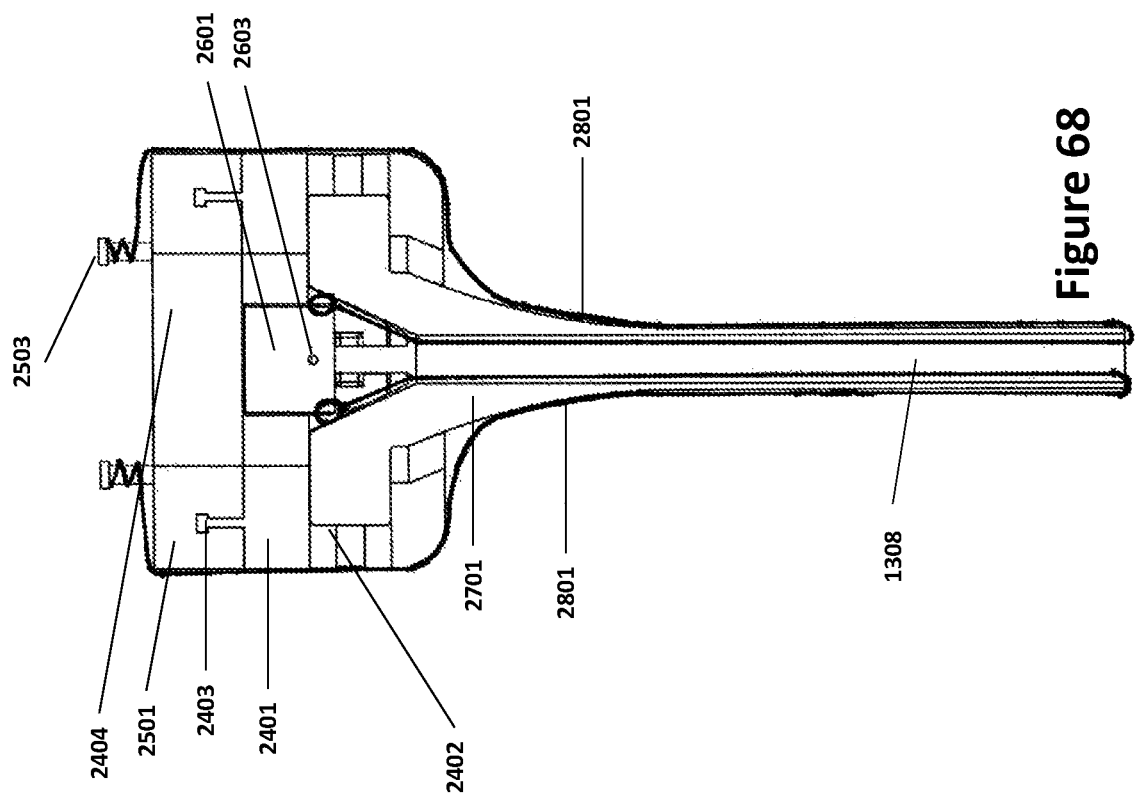
FIG. 68 is a cross-sectional side view of the example embodiment shown in FIG. 67.
Figure 67:
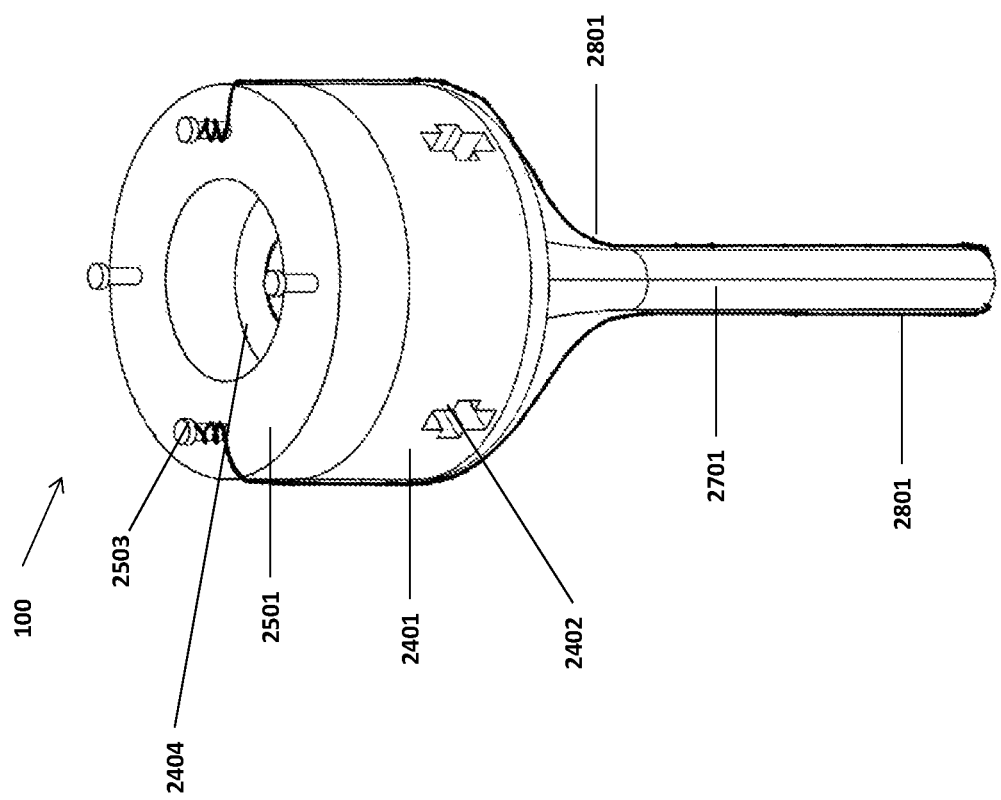
FIG. 67 is an isometric view of an example of an expandable cannula device embodiment, at an unexpanded state, where expansion of the elongate rigid members is effected by rotating a rotatable member located on the first housing and is connected by wires to a rigid member.
Figure 70:
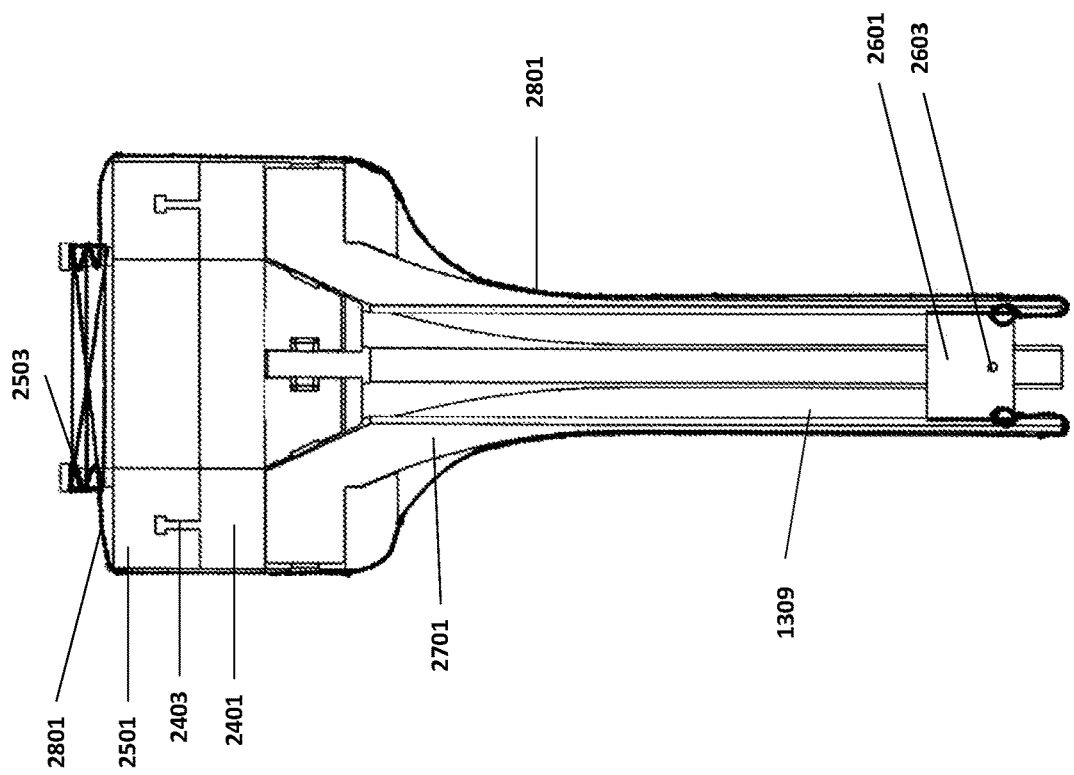
FIG. 70 is a cross-sectional side view of the example embodiment shown in FIG. 69.
Figure 69:
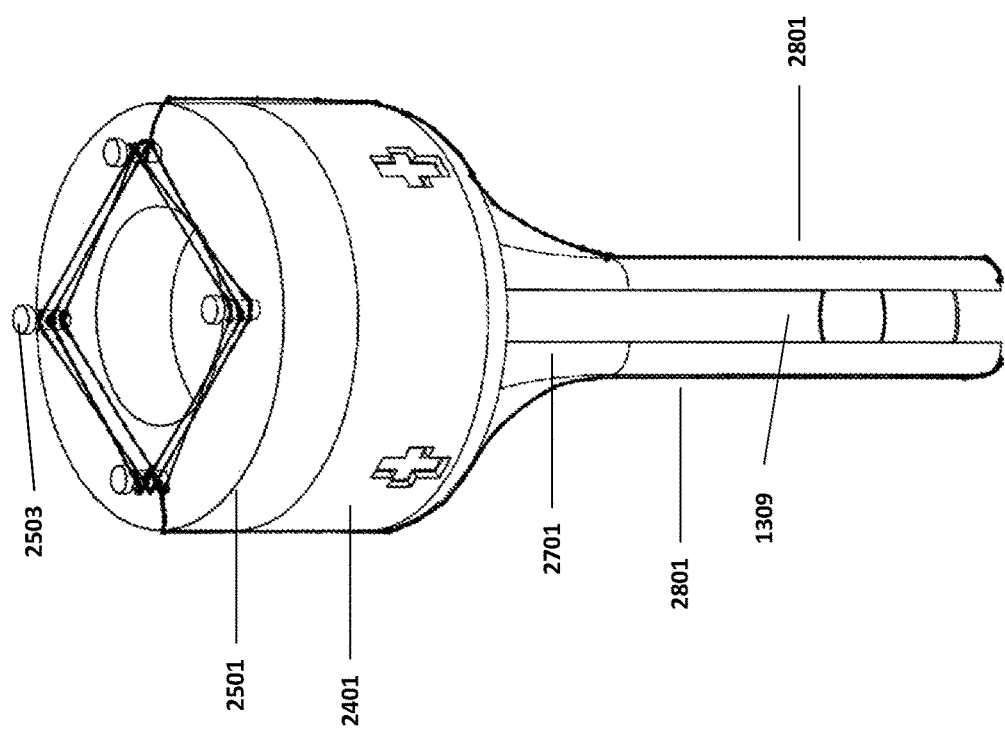
FIG. 69 is an isometric view of the example embodiment of FIGS. 67-68, where the rotatable member is rotated and the cannula is expanded by advancement of a rigid member distally into the passage of the cannula by wires.
Figure 72:
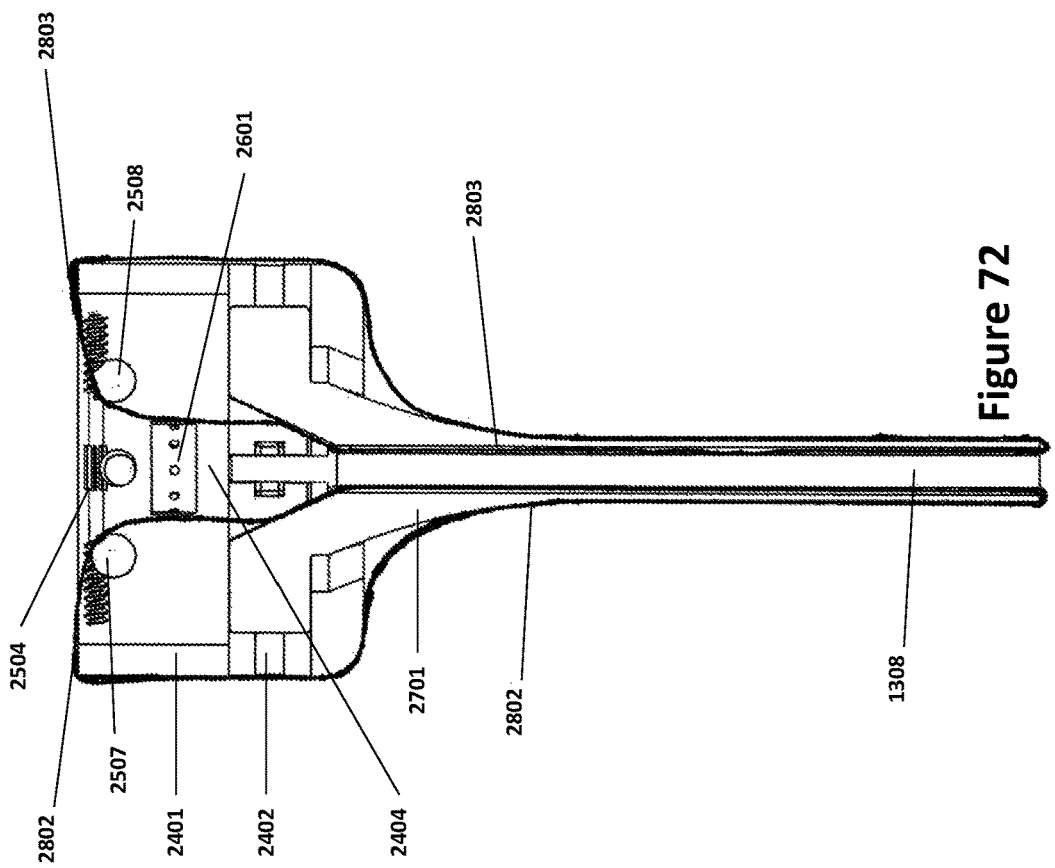
FIG. 72 is a cross-sectional side view of the example embodiment of FIG. 71
Figure 71:
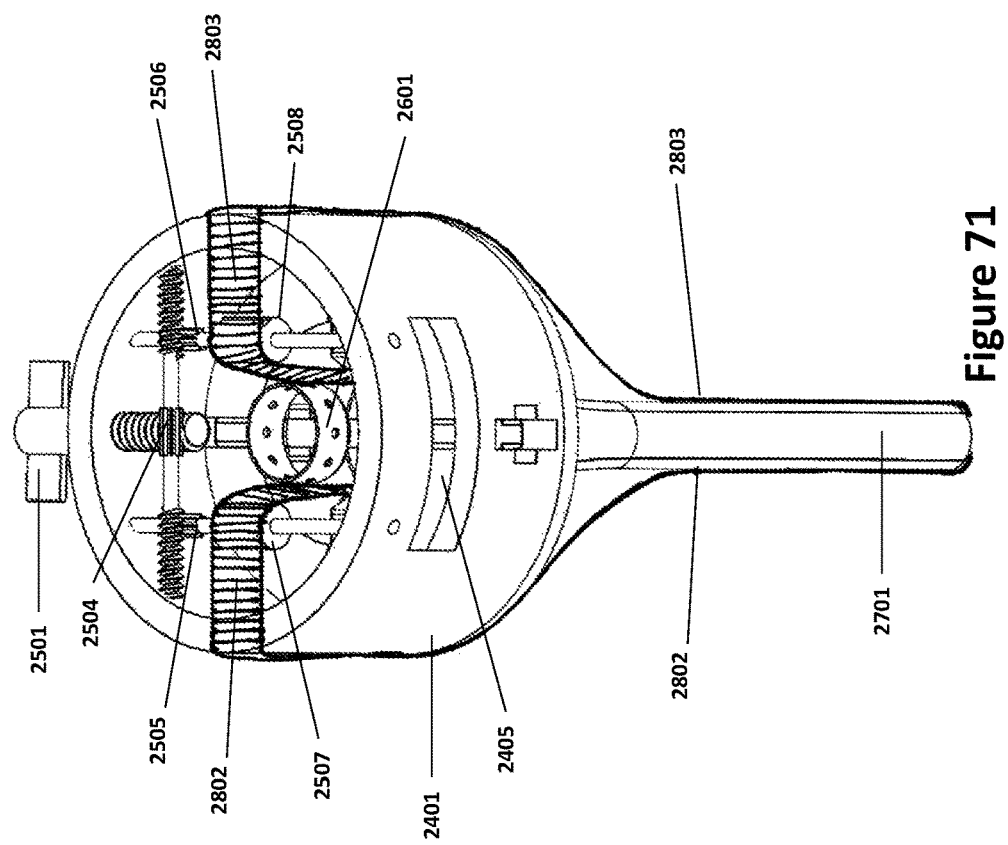
FIG. 71 is an isometric view of an example of an expandable cannula device embodiment, where expansion of the elongate rigid members is effected by rotating a rotatable member located on the first housing and is connected by a mechanical system to conveyor belts which interact with a rigid member to effect expansion of the cannula
Figure 74:
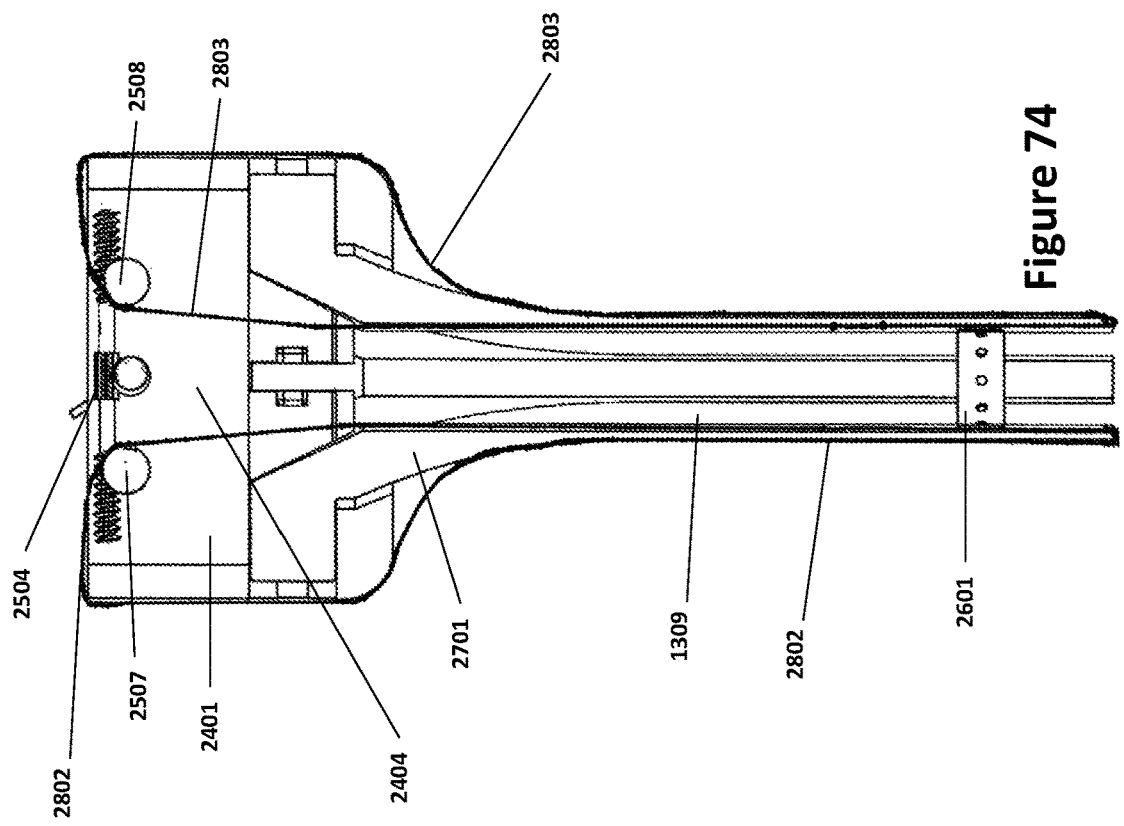
FIG. 74 is a cross-sectional side of view of the example embodiment shown in FIG. 73.
Figure 73:
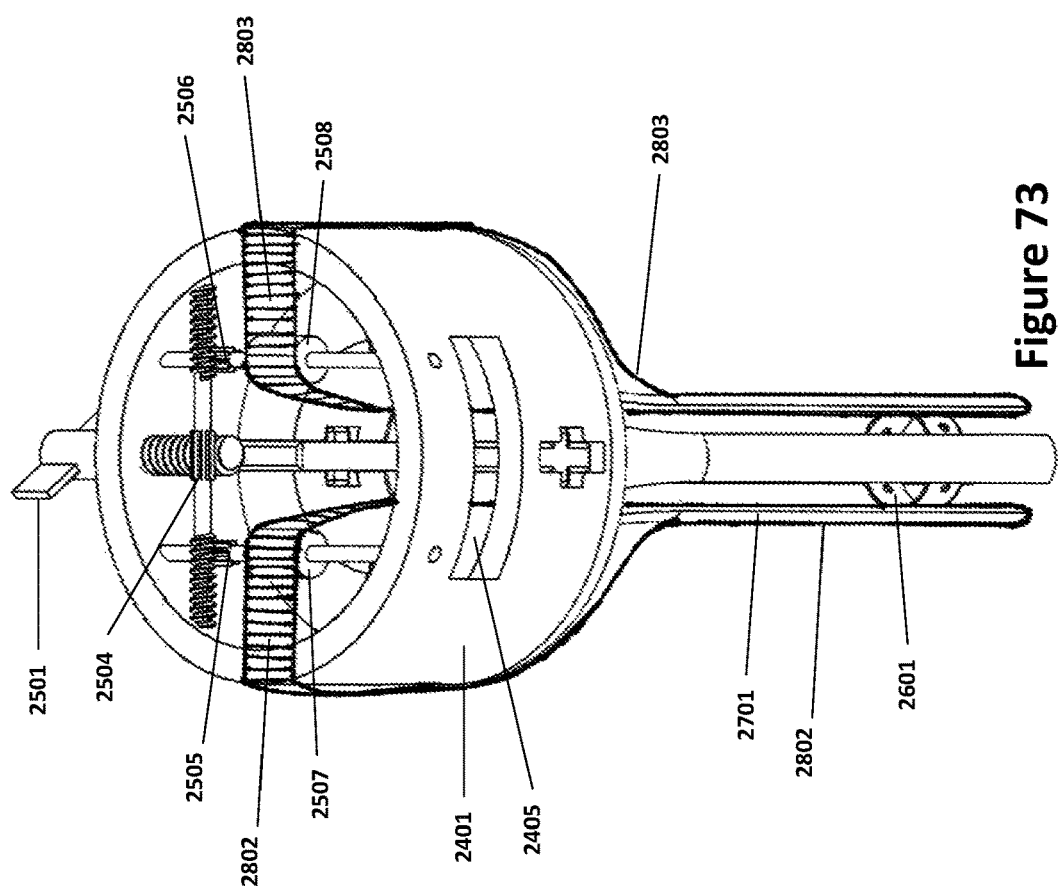
FIG. 73 is an isometric view of the example embodiments shown in FIGS. 71-72, at an expanded state
Figure 76:
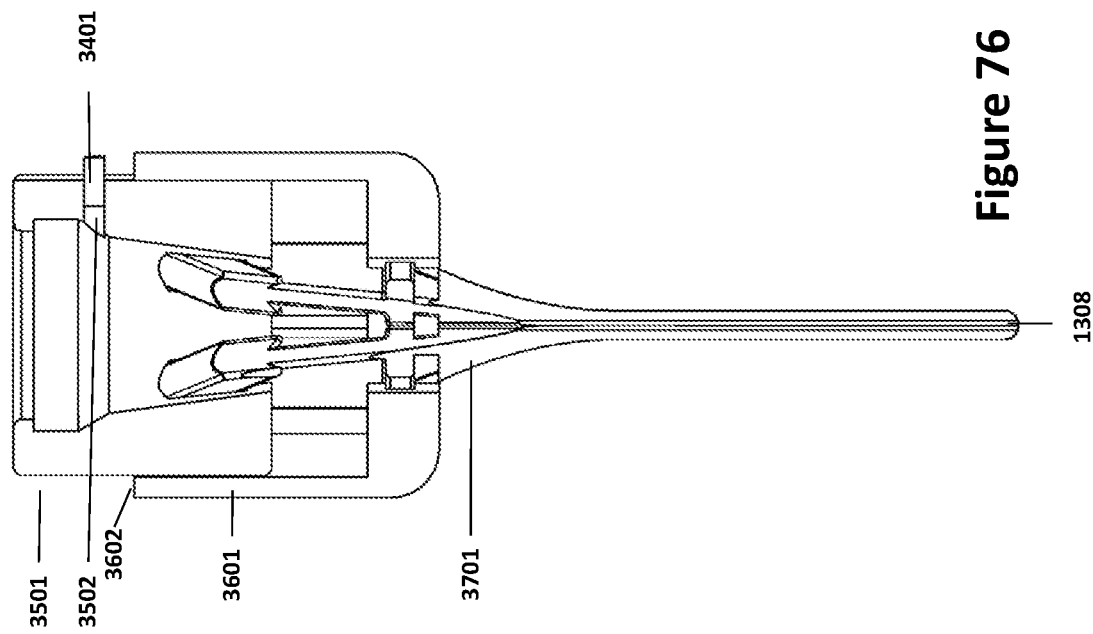
FIG. 76 is a cross-section of the example embodiment shown in FIG. 75.
Figure 75:
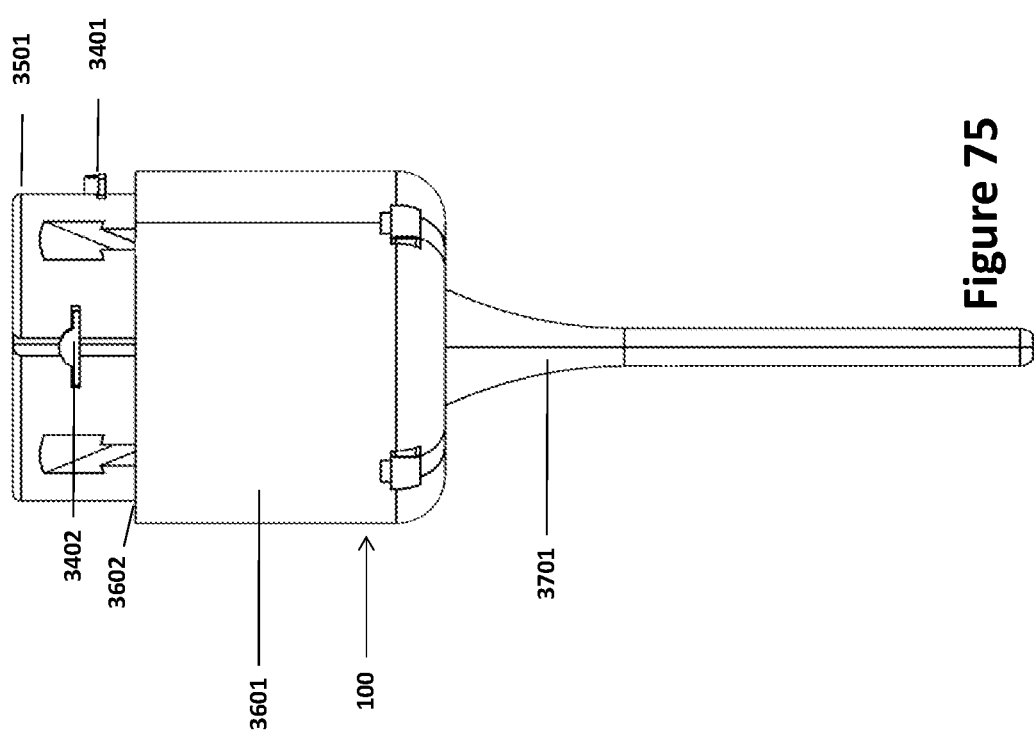
FIG. 75 is a side-view of an example embodiment of an expandable cannula device with a plurality of movable pins in the first housing configured to limit the amount of movement of the second housing relative to the first in order to limit the amount of expansion of the cannula.
Figure 80:
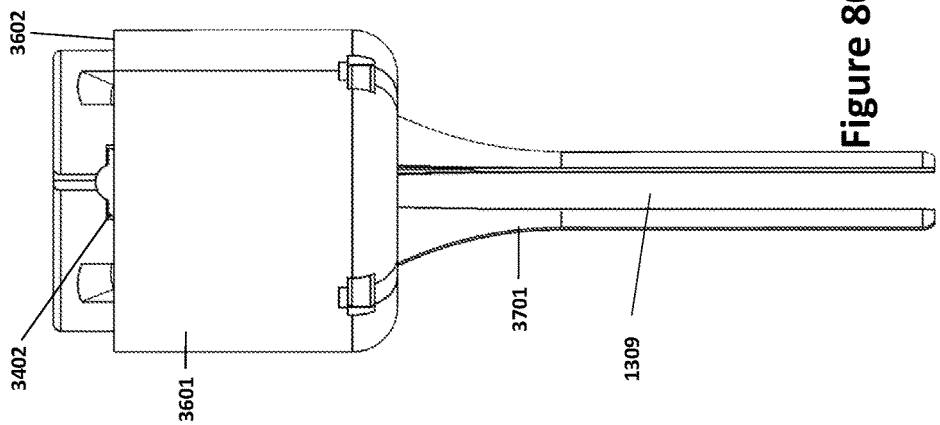
FIG. 80 is a side-view of the example embodiment shown in FIG. 79.
Figure 79:
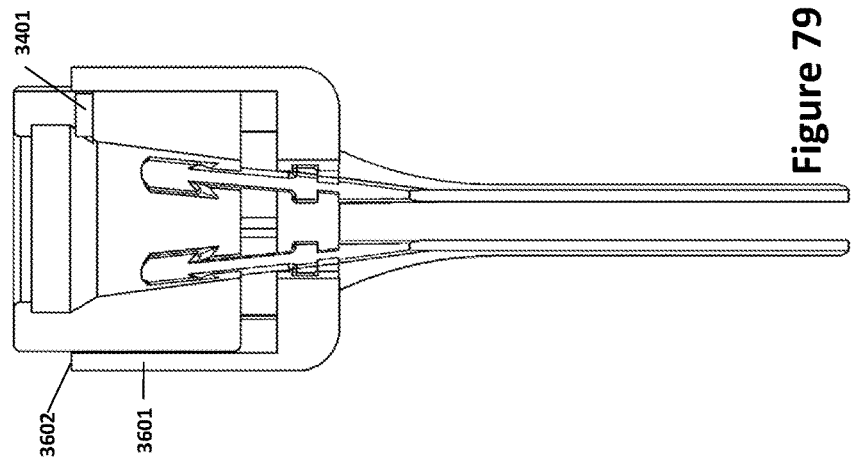
FIG. 79 is a cross-sectional side view of an example of the embodiments shown in FIGS. 77-78, wherein the first pin is either inserted into a groove or removed, such that the second housing is movable to a second position where its motion is constricted by a second pin.
Figure 78:
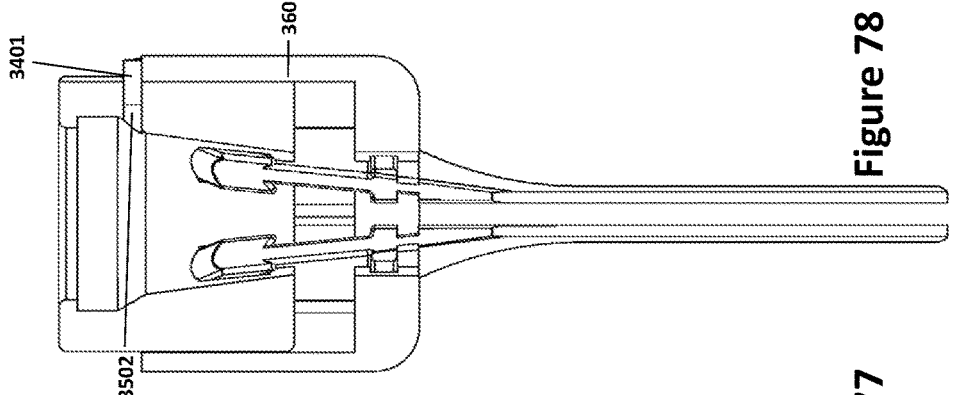
FIG. 78 is a cross-sectional view of the example embodiment shown in FIG. 77.
Figure 77:
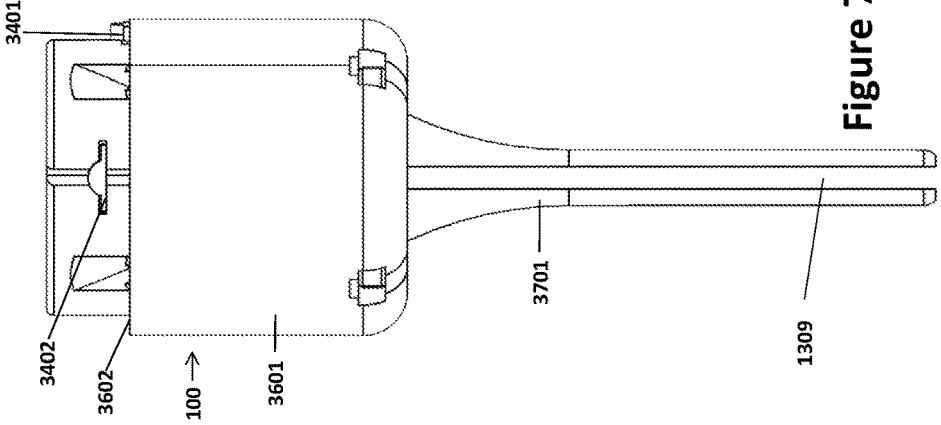
FIG. 77 is a side view of an example of the embodiments shown in FIGS. 75-76, where the second housing is constricted by a first pin to move up to a first position.
Figure 81:
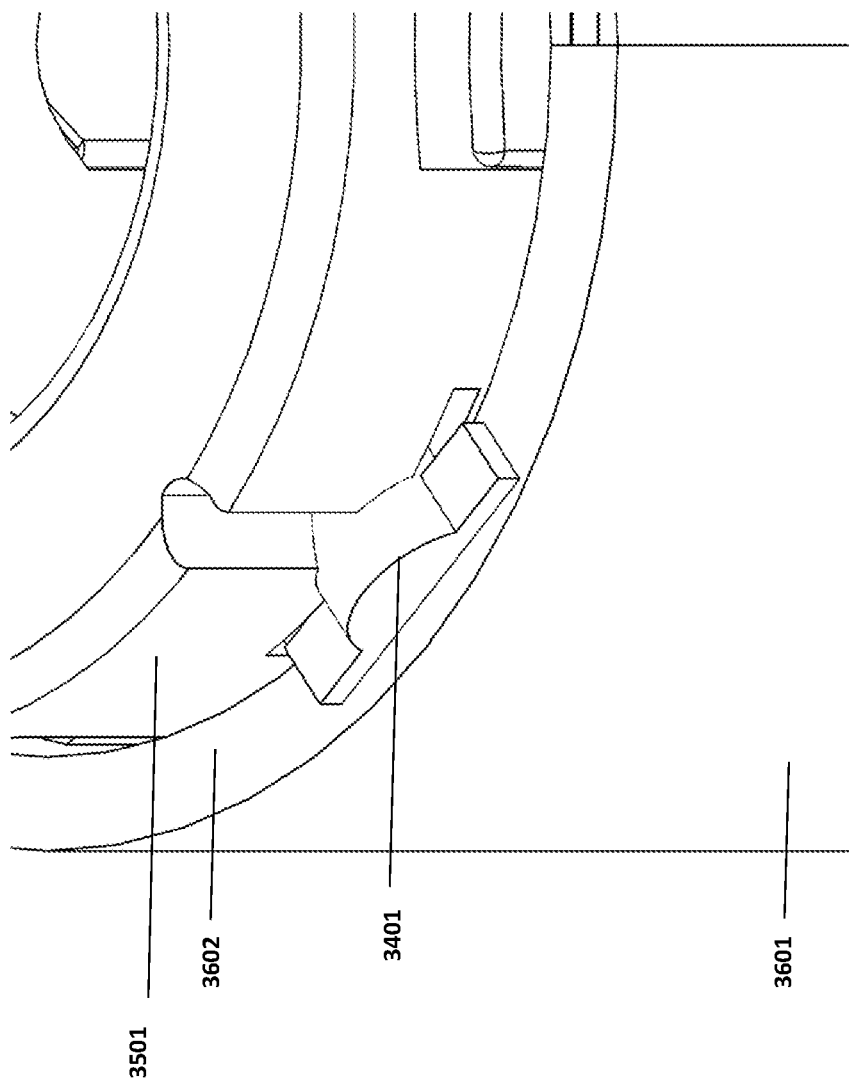
FIG. 81 is a close-up isometric view of the expansion control mechanism shown in FIGS. 75-80.
Figure 83:
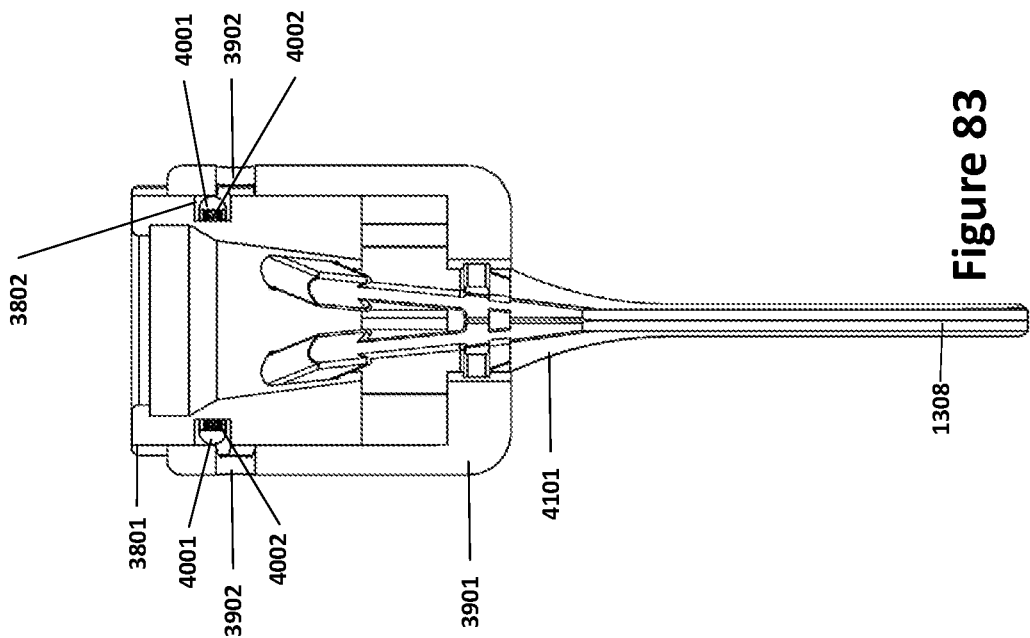
FIG. 83 is a cross-sectional side view of the example embodiment of the device shown is FIG. 82
Figure 82:
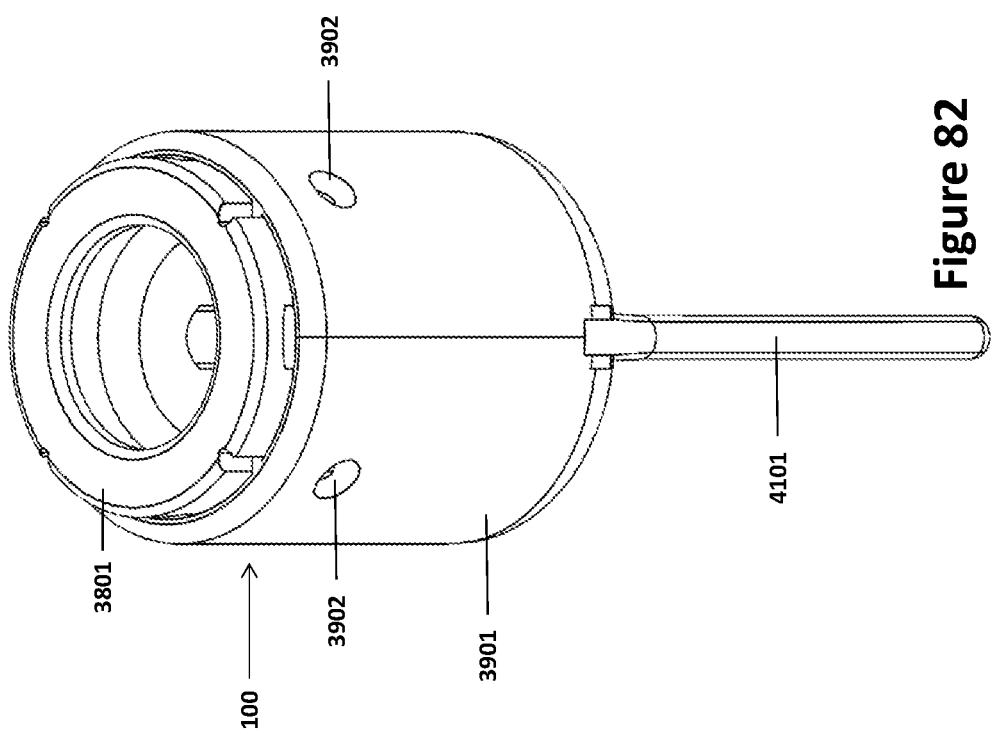
FIG. 82 is an isometric view of an example embodiment of an unexpanded expandable cannula device with a spring-loaded pin method to lock movement of second housing relative to first housing at a specific position.
Figure 85:
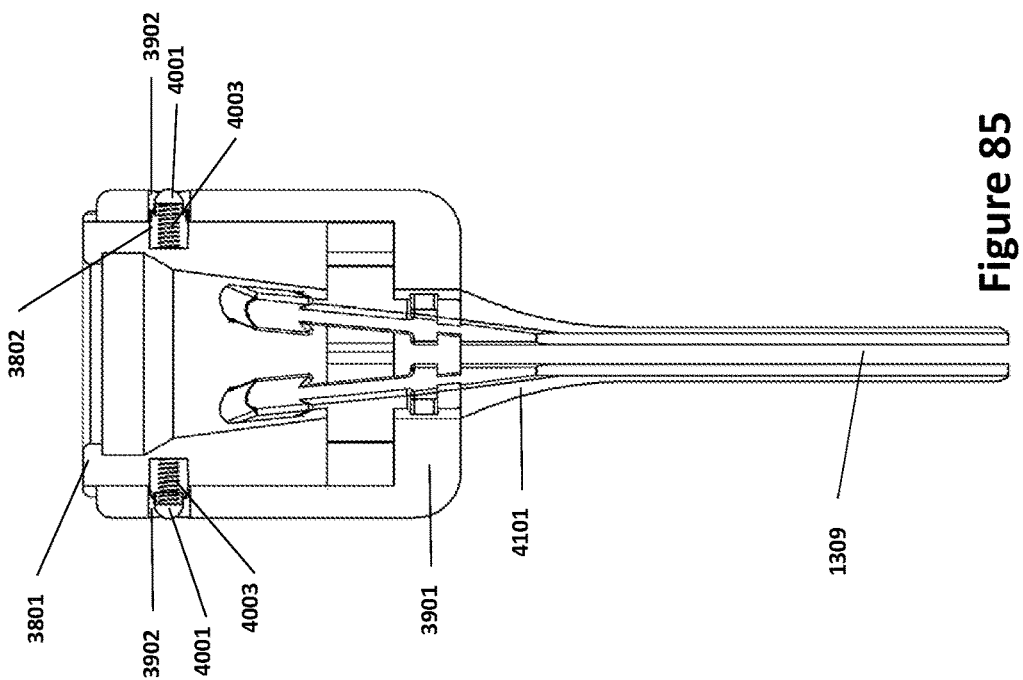
FIG. 85 is a cross-sectional side view of the example embodiment shown in FIG. 84, further illustrating the mechanism.
Figure 84:
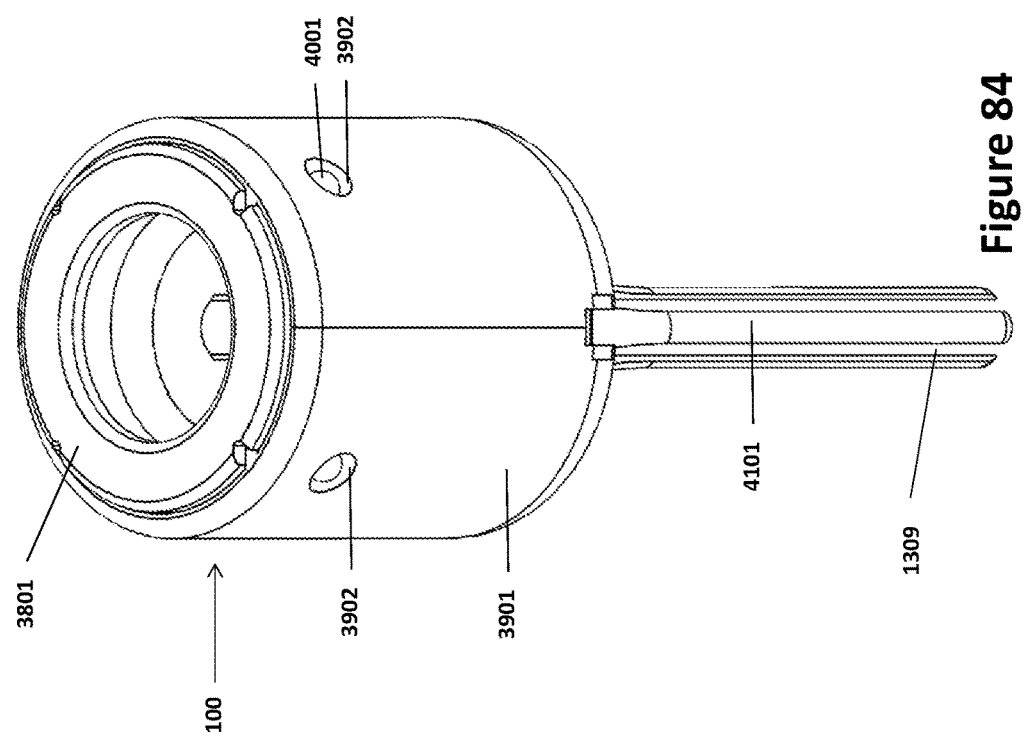
FIG. 84 is an isometric view of the example embodiment of an expanded version of the expandable cannula device in FIGS. 82-83, with the second housing movement being locked at a position that prevents the cannula from being further expanded or contracted.
Figure 88:
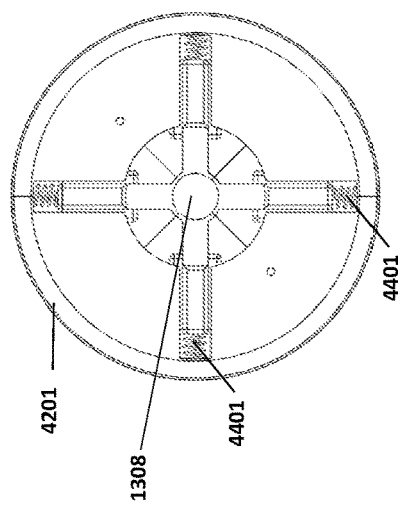
FIG. 88 is a cross-sectional top view of the example embodiment of the device shown in FIGS. 86-87.
Figure 87:
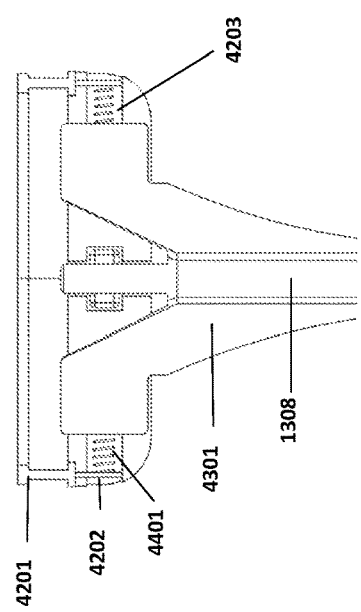
FIG. 87 is a cross-sectional side view of the example embodiment of the device shown in FIG. 86.
Figure 86:
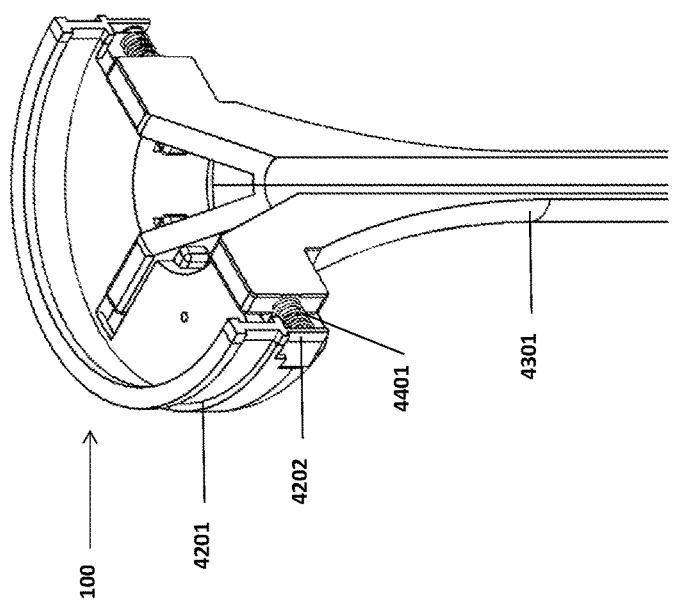
FIG. 86 is a cross-sectional isometric view of an example embodiment of an expandable cannula device with a biasing mechanism, comprising springs, to bias the elongate rigid members towards an unexpanded configuration.
Figure 91:
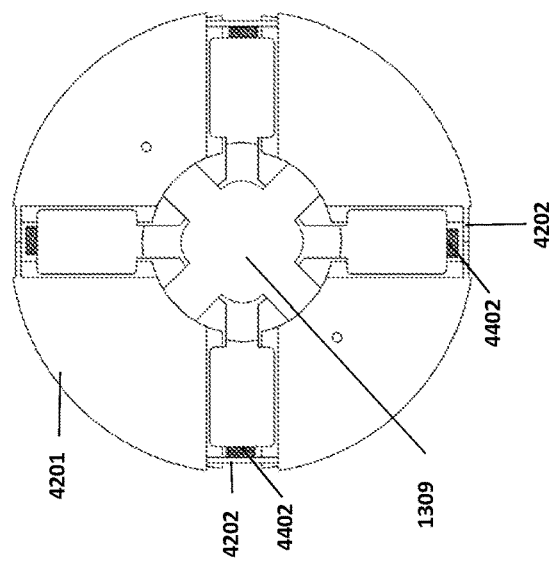
FIG. 91 is a cross-sectional top view of the example embodiment shown in FIGS. 89-90.
Figure 90:
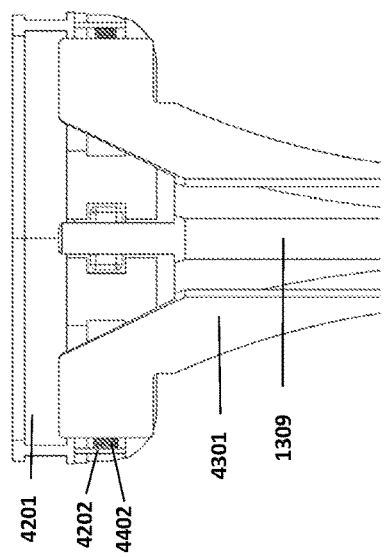
FIG. 90 is a cross-sectional side view of the example embodiment shown in FIG. 89.
Figure 89:
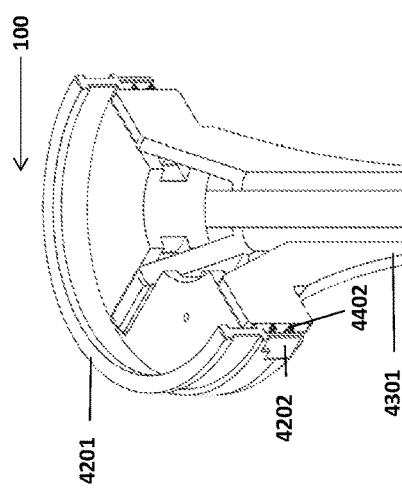
FIG. 89 is a cross-sectional isometric view of the example embodiment of FIGS. 86-88, with the biasing spring being compressed and the elongate rigid members configured in an expanded position.
Figure 93:
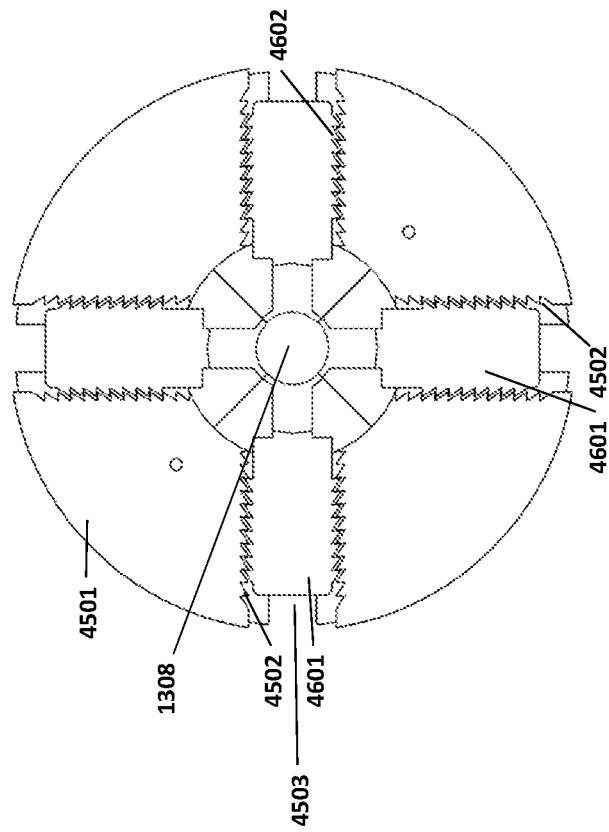
FIG. 93 is a cross-sectional top view of the example embodiment shown in FIG. 92
Figure 92:
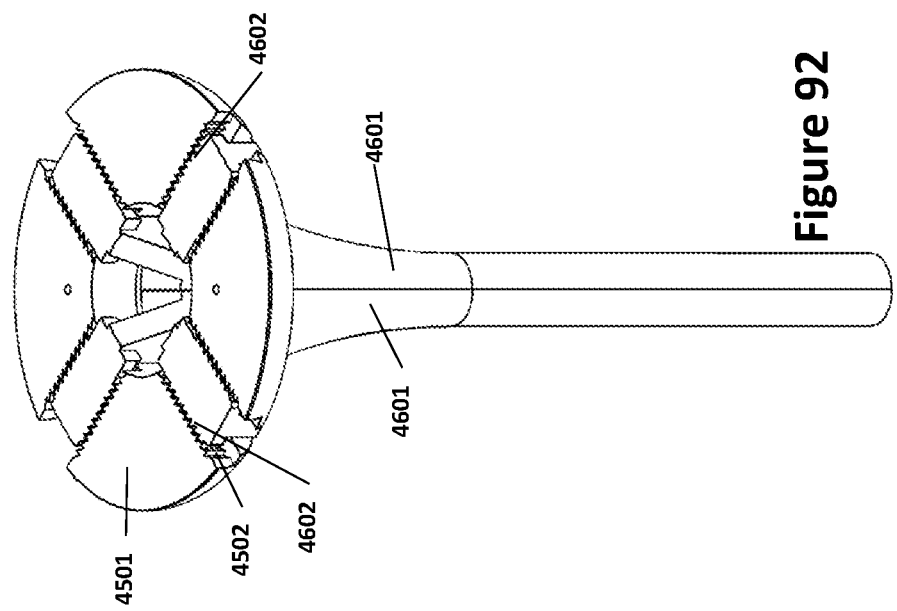
FIG. 92 is an isometric top cross-sectional view of an example embodiment of an expandable cannula device where the plurality of elongate rigid members and the grooves of the housing in which they slide to expand comprise one-way ratchet features that are configured to only allow movement of elongate rigid members in an expanding direction.
Figure 95:
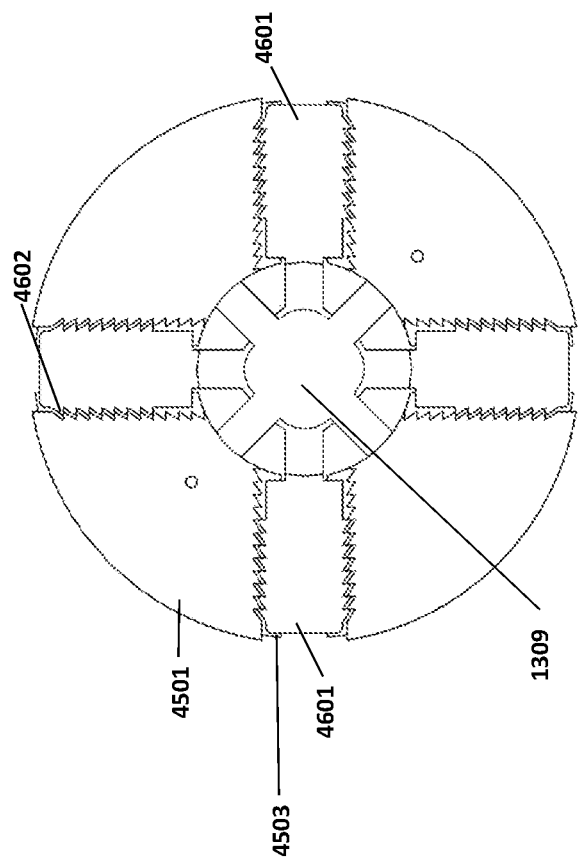
FIG. 95 is a cross-sectional top view of the example embodiment shown in FIG. 94.
Figure 94:
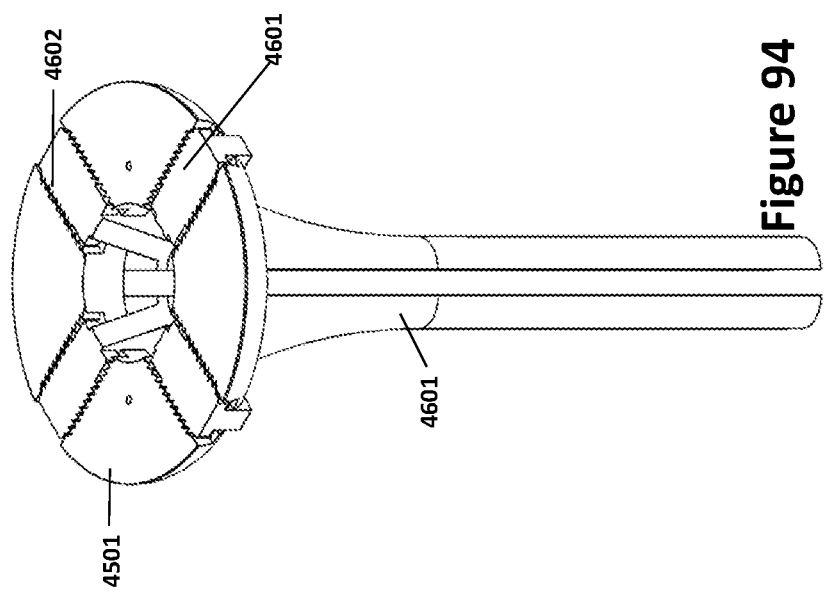
FIG. 94 is an isometric top cross-sectional view of the example embodiment shown in FIGS. 92-93, where the elongate rigid members are expanded.
Figure 98:
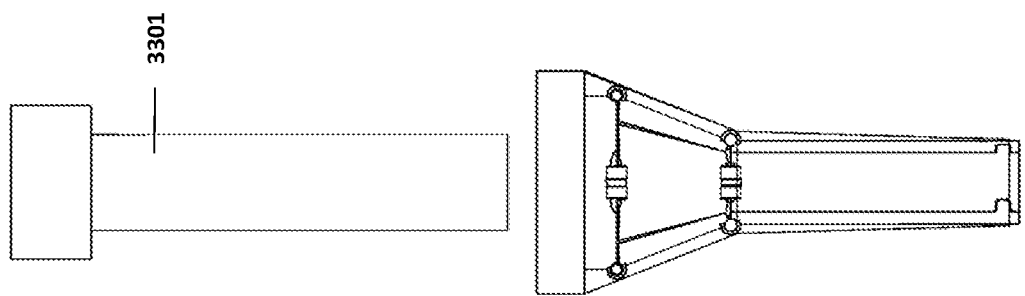
FIG. 98 is a side view of the example embodiment shown in FIGS. 96-97, with an expansion insert, not yet inserted into the passage of the unexpanded cannula device.
Figure 97:
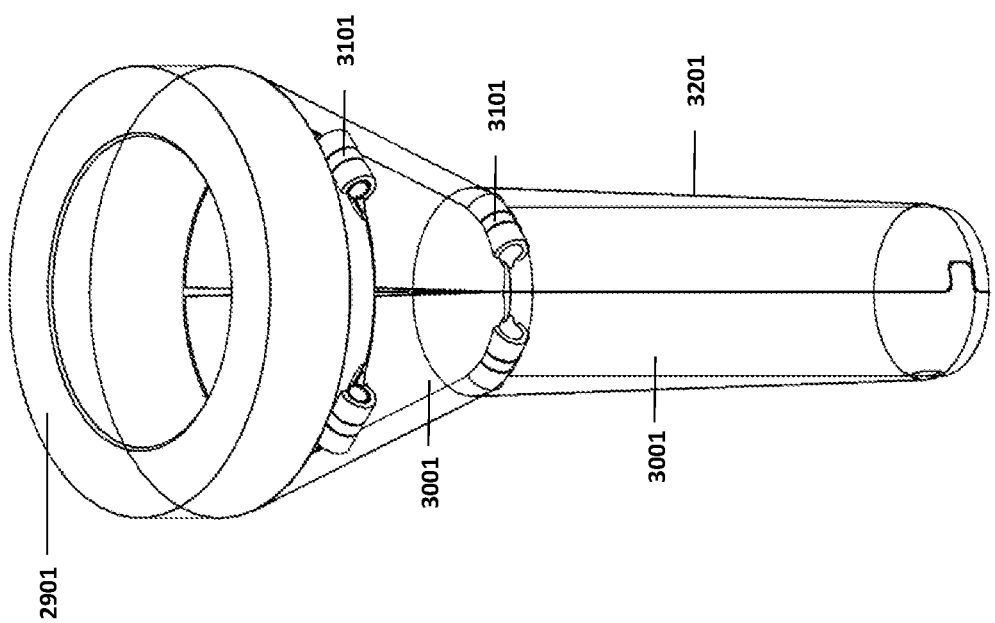
FIG. 97 is an isometric view of the example embodiment shown in FIG. 96.
Figure 96:
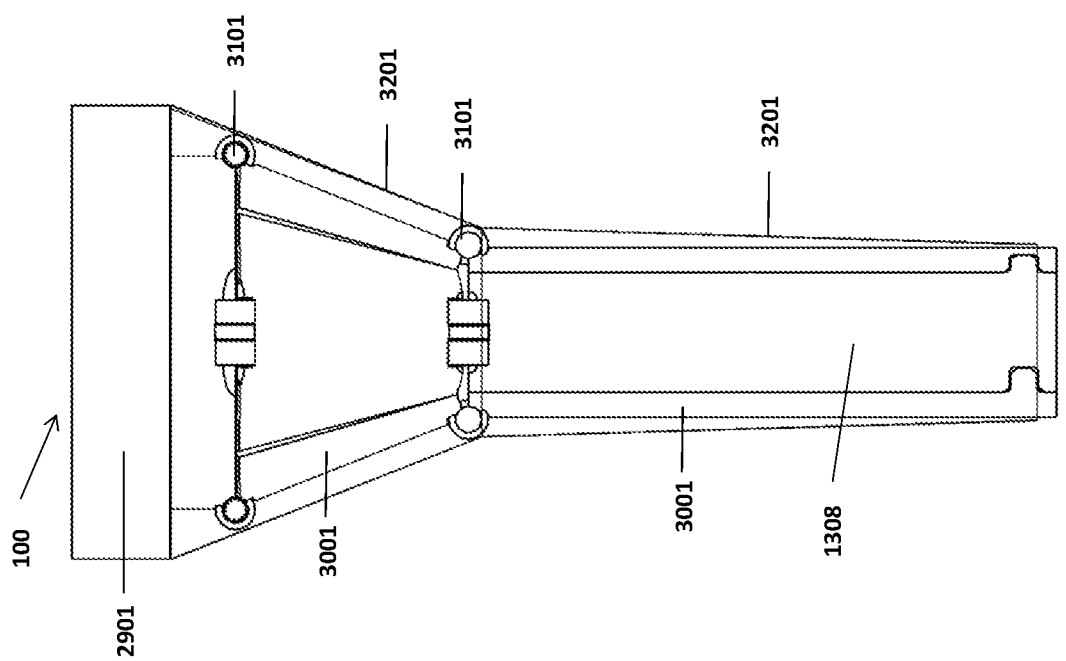
FIG. 96 is a side view of an example embodiment of an expandable cannula device with hinged elongate rigid members, at an unexpanded state.
Figure 101:
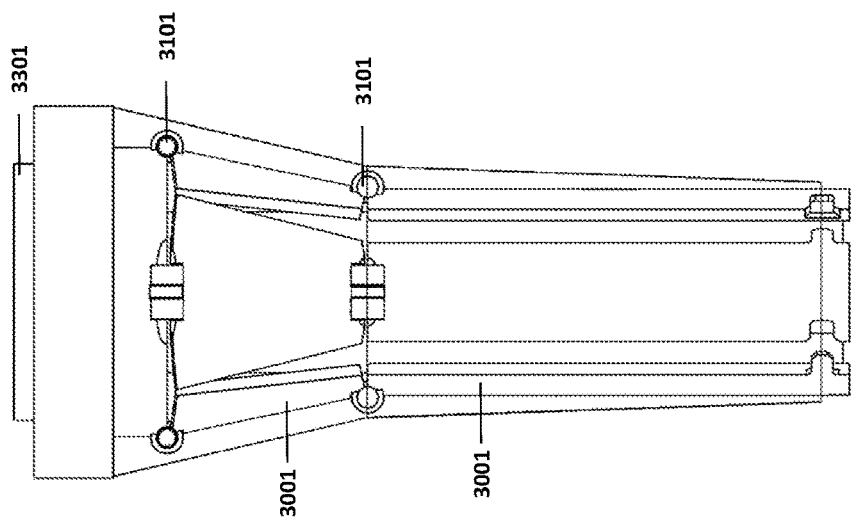
FIG. 101 is a side view of the example embodiment shown in FIG. 100.
Figure 100:
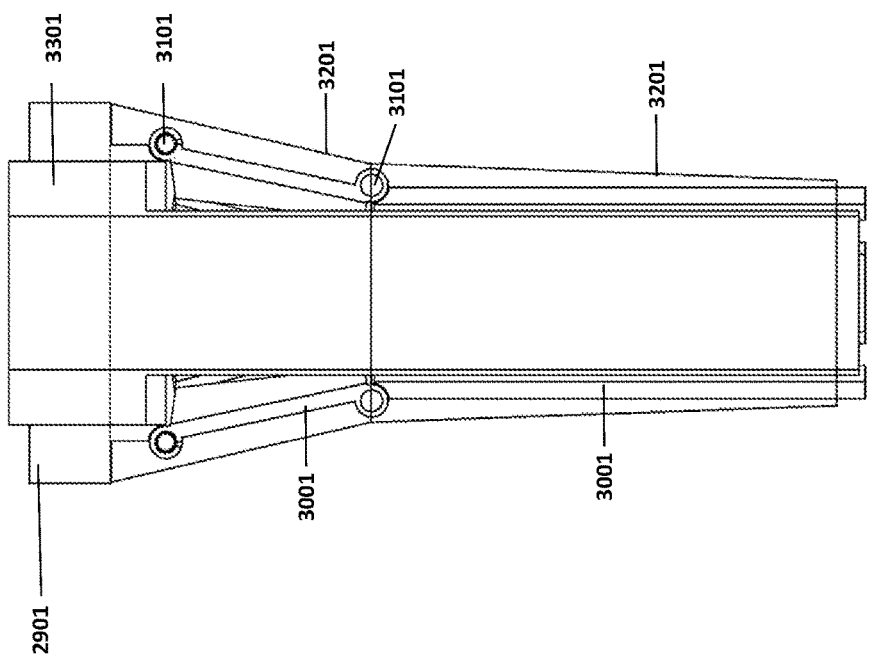
FIG. 100 is a cross-sectional side view of the example embodiment of the expandable cannula device shown in FIG. 99.
Figure 99:
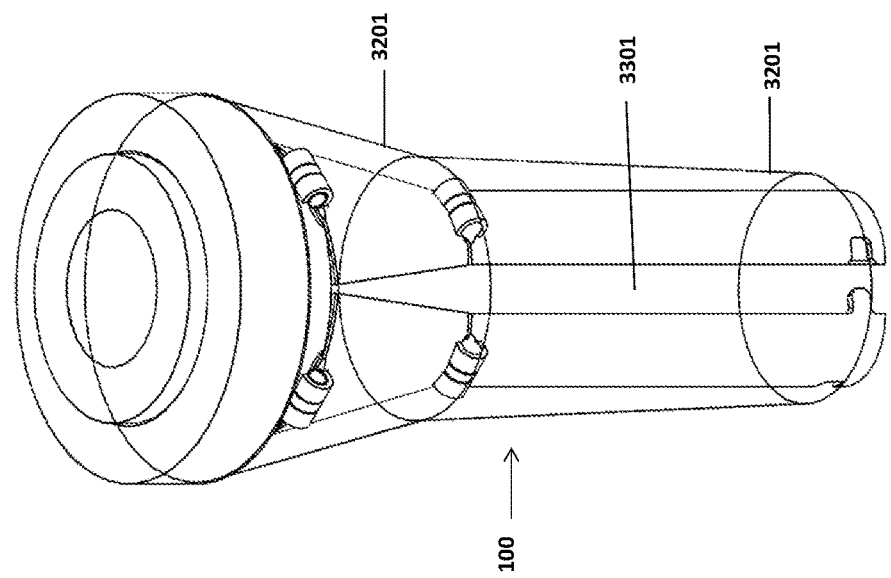
FIG. 99 is an isometric view of the example embodiment shown in FIGS. 96-98, with the expansion insert inserted into the passage of the expandable cannula device causing the plurality of hinged elongate rigid members to expand and create an expanded configuration of the device.
Figure 103:
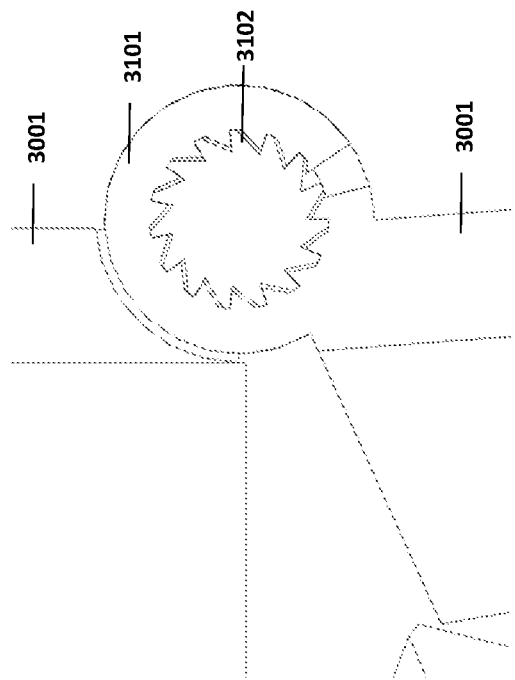
FIG. 103 shows the pair of elongate rigid members being expanded and locked in the expanded position by the hinges comprising rotational one-way ratchet features
Figure 102:
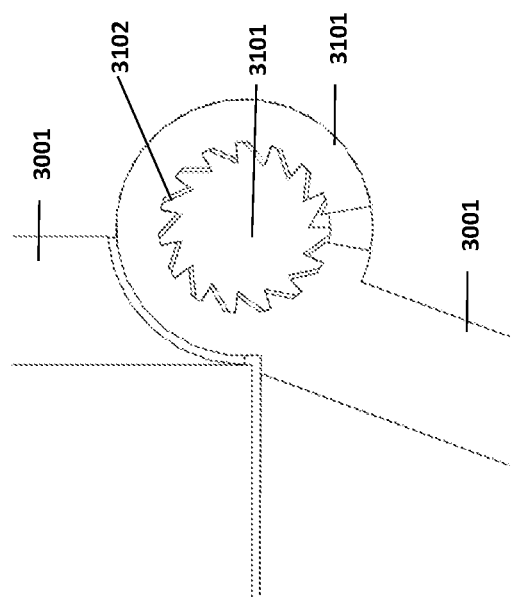
FIG. 102 is a cross-sectional close-up side view of the example embodiment of the hinges depicted in example embodiments shown in FIGS. 94-101, in-which case, the hinge comprises rotational one-way ratchet features, wherein a pair of hinged elongate rigid members are hinged at an unexpanded configuration.
Figure 109:
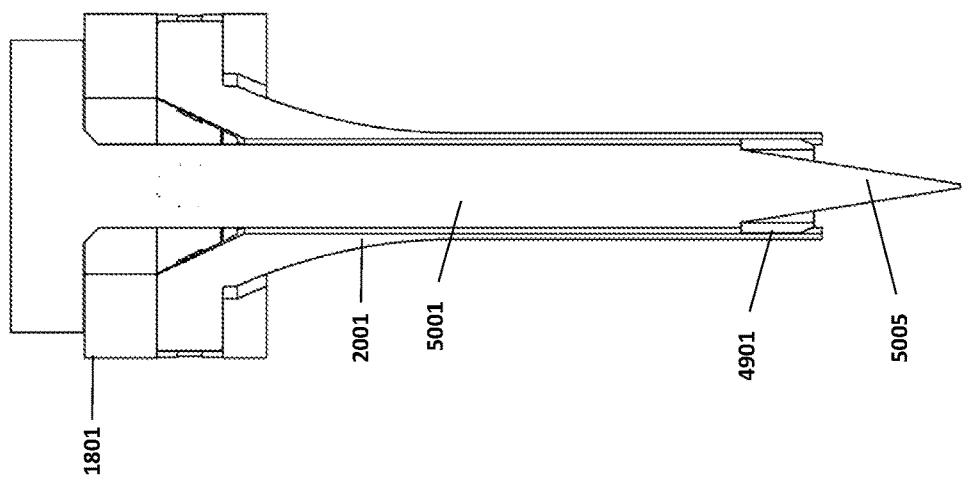
FIG. 109 is a cross sectional side view depicting the obturator being used to insert the insertable member shown in FIGS. 104-108 into a distal region of the expanded expandable cannula device.
Figure 108:
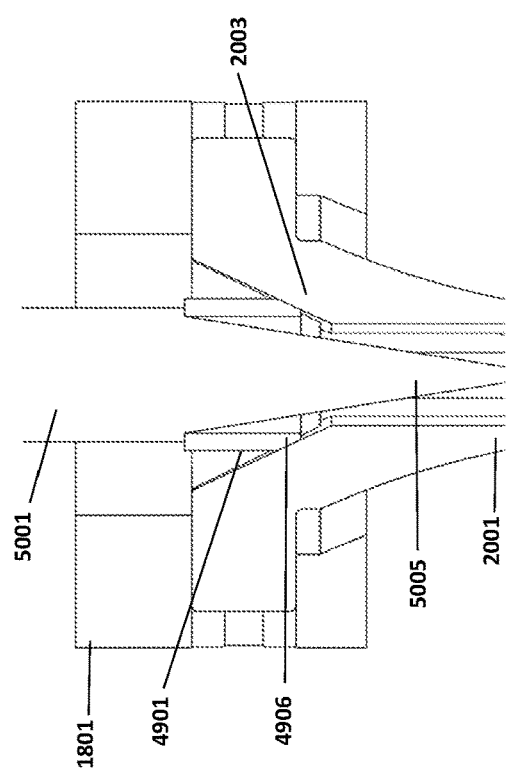
FIG. 108 is a cross sectional side view depicting the mechanism by which the insertable member shown in FIGS. 104-107 moves the elongate rigid members away from each other in order to create an expanded passage, and thus an expanded cannula.
Figure 107:
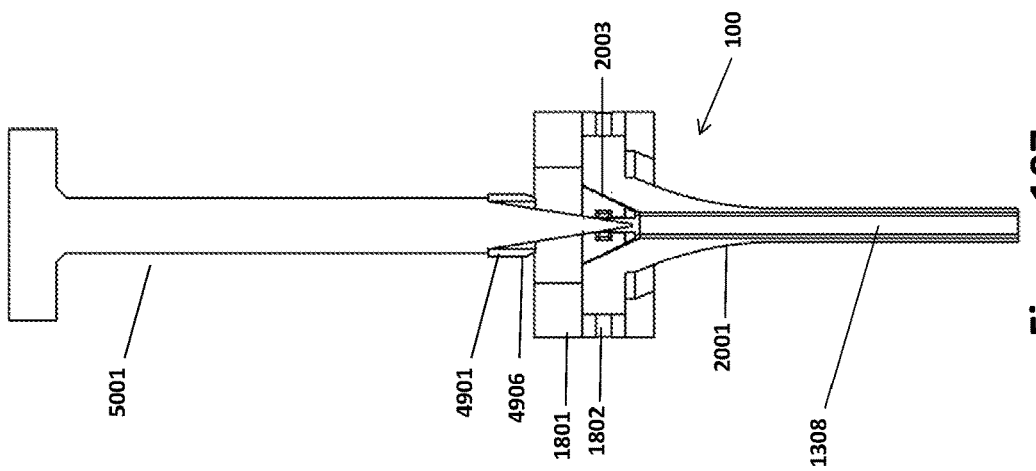
FIG. 107 is a cross-sectional side view of the example embodiments of the obturator and the insertable member as they are being inserted into the passage of an example embodiment of an unexpanded expandable cannula device
Figure 111:
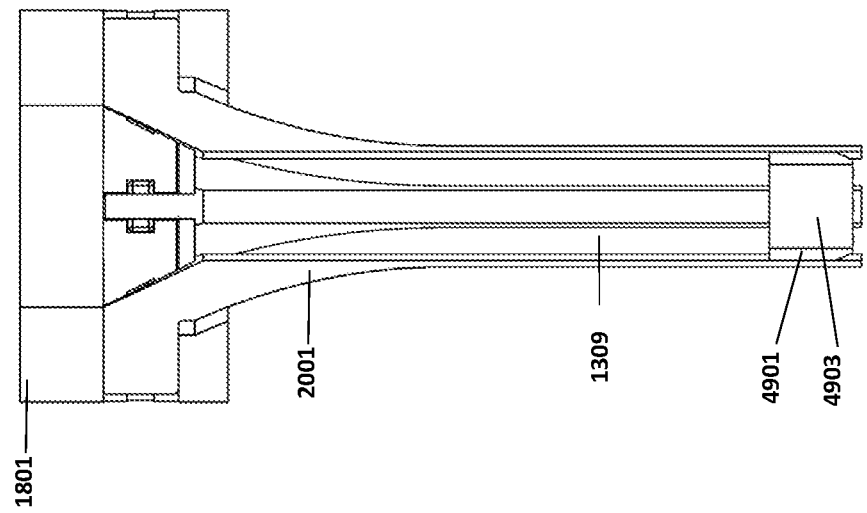
FIG. 111 is a cross-sectional side view of the embodiment device of FIG. 110.

With reference to FIGS. 26-28: obturator for penetrating tissue.

And with reference to previous embodiments, the expandable cannula device 100 may further comprise a second obturator 1001 for penetrating said expandable cannula device 100 into tissue of a subject.

The obturator 1001 is inserted into the first housing throughbore 1103, all the way through the unexpanded passage 1308 so that the obturator tip 1003 is exposed prior to inserting the expandable cannula device 100 into tissue. In some embodiment, the obturator 1001 has an exterior surface 1002 that is complimentary to the interior surface 1307 of the elongate rigid members 1301. The exterior surface 1002 of the obturator 1001 and the interior surface 1307 of elongate rigid members 1301 may be tapered. By applying force onto the obturator 1001, the obturator tip 1003 penetrates the tissue. Once the expandable cannula device 100 has fully penetrated the tissue, the obturator 1001 can be removed such that an unexpanded passage 1308 is created between the external environment and the internal tissue. Surgical instruments, specimens, fluids and other material can be passed back and forth from the external environment and into the tissue or vice versa through the passage unexpanded passage 1308, which may be expanded to larger passage, thus comprising an expanded passage 1309 by expansion mechanisms described earlier.

With reference to FIGS. 151-153: Obturator with insufflation port.

This embodiment shows an expandable cannula device 100 with a second obturator 5801. In some embodiments, the obturator 5801 comprises a first insufflation port for injecting gas into a subject tissue cavity after penetrating the tissue. The insufflation port is comprised of a stopcock 5802 with a stopcock handle 5803 which controls whether gas insufflation is on or off by being rotated by the user. The obturator 5801 comprises a fluid track 5804 that travels from the stopcock 5802 and through the shaft of the obturator towards its distal tip, where the gas would exit.

With reference to FIGS. 154-155: blunt/sharp tipped obturator and retractable bladed obturator.

This embodiment shows an obturator 5801 with at least one of blade 5805 which is located on the shaft of the obturator 5801. In some embodiments, the blade 5805 is located at a proximal position relative to the tip of the obturator 5801. In some embodiments (not shown), the blade 5805 is located adjacent to the tip of the obturator 5801. In some embodiments (not shown) the blade 5805 may protrude from the tip 5806 of the obturator 5801. In some embodiments, the blade 5805 comprises a retractable blade.

In some embodiment the tip 5806 of the obturator 5801 is a blunt. In some embodiments, the tip 5806 is tapered. In some embodiments, the tapered tip 5806 is sharp.

In some embodiments (not shown), an actuation mechanism causes the at least one blade 5805 to become exposed from the shaft of the obturator 5801 when the tip 5806 is under pressure, such as when the obturator 5801 is penetrating a subject tissue, however, as soon as the tip 5806 breaches the tissue layers and pressure is no longer exerted on it, the blade 5805 retracts back into the shaft of the obturator 5801. The actuation mechanisms are familiar to the individuals experienced in the art.

In some embodiments (not shown), the obturator 5801 comprises tip 5806 that is biased. In some embodiments, the biased tip 5806 is spring-loaded, such that when the tip 5806 is subjected to pressure, for example when the obturator penetrates a subject tissue, the tip 5806 retracts towards a proximal position, and this retraction of the tip 5806 exposes the at least one blade 5805.

In some embodiments (not shown), the obturator 5801 comprises a hollow shaft, wherein said shaft is terminated distally by the obturator tip 5806. In some embodiments, the obturator 5801 is made from optically transparent or translucent material. In some embodiments, a medical imaging probe, such as a laparoscope may be inserted into the said hollow shaft of the obturator but may not protrude past the tip 5806.

With reference to FIGS. 156-163: pressure evacuation.

In some embodiments of an expandable cannula device 100 (first and or second housing not shown), elongate rigid members 7101 comprise a channel 7102 through which fluid may flow. The channel 7102 extends from a location along the elongate rigid member 7101, distally and into the surgical cavity in the subject. The channel communicates with a hollow portion 7105 of an obturator 7104 through holes 7108 in the obturator 7104.

In general, the removal of an obturator 7104 from the unexpanded passage 1308 of such an expandable cannula device 100, creates a negative pressure in the penetrated cavity; however, in this embodiment the negative pressure withdraws the fluid in the hollow portion 7105 of the obturator 7104 and causes it to travel through the channels 7102 of each of the elongate rigid members 7101, and finally reach the penetrated cavity, such that that the negative pressure is relieved and an equilibrium of pressure is achieved in the cavity.

In some embodiments (not shown), positive pressure in the cavity of patient is generated when an obturator 7104 is inserted through an unexpanded passage 1308 or through an expanded passage 1309 or through the transition between an unexpanded passage to an expanded passage 1309. Thus, in some embodiments, the hollow portion 7105 of the obturator 7104 is open to the external environment, which prevents buildup of positive pressure in the cavity of a subject.

In some embodiments the obturator tip 7106 may contain at least one channel 7107 that is connected to the hollow portion 7105 of the obturator 7104.

These embodiments may be used as methods of maintaining an equilibrium intracranial pressure during use of a cannula device in minimal invasive brain surgeries.

Elongate rigid members with mating features:

In some embodiments (not shown), each adjacent pair of the plurality of elongate rigid members 1301 comprise a mating mechanism for mating the adjacent pair of the plurality of elongate rigid members 1301. In some embodiments (not shown), the mating mechanism comprises complimentary tongues and grooves. In some embodiments (not shown), the mating mechanism comprises complimentary male and female features.

Retractable blade on the elongate rigid members:

In some embodiments (not shown), the elongate rigid members 1301 comprise a retractable blade. In some embodiments (not shown), the blade is exposed during the expansion of the elongate rigid members 1301 from an unexpanded passage 1308 to an expanded passage 1309.

Lubrication Methods:

In some embodiments (not shown), in order to reduce friction between moving surfaces and parts of various embodiments of the expandable cannula device 100, moving surfaces may be coated by a lubricant. In some embodiments, the lubricant may be a polytetrafluoroethylene-based lubricant, a graphite-based lubricant, mineral oil, a silicone-based lubricant, or a poly(p-xylylene) (also known as parylene) based coating.

Additionally, or alternatively, in efforts to further reduce friction between moving surfaces, ball bearings may also be disposed on said moving surfaces, such as the plurality of first tongue features 1302 and/or the plurality of guide grooves 1102.

With reference to FIGS. 164-166: cannula with 1-way valve and adjustable valve.

This embodiment shows an expandable cannula device 100 device with at least one one-way fluid valve 5501. In some embodiments, the one-way fluid valve 5501 is disposed in a proximal region of the first housing 1101.

A variety of one-way fluid valves are known to those experienced in the art.

With reference to FIGS. 167-170:

The expandable cannula device 100, the at least one one-way fluid valve 5501 comprises an adjustable valve.

In some embodiments, the adjustable valve comprises an inner diameter 6001 and can expand the inner diameter towards a second inner diameter 6009 that is larger than the first inner diameter 6001.

The adjustable valve is comprised of at least one layer of a plurality of leaflets 6002. The plurality of leaflets 6002 comprise an inner diameter 6001, and second inner diameter 6009 of the adjustable valve. In some embodiments, the inner diameter 6001, and second inner diameter 6009 of the adjustable valve may be adjusted by a driving member 6005.

In some embodiments (not shown), the movement of the driving member 6005 is effected by the movement of the elongate rigid members relative to each other.

In some embodiments the driving member 6005 may comprise a generally circular in shape and defines an axis concentric with the central axis of the expandable cannula device 100.

In some embodiments, the driving member may be an outer ring 6005.

A first inner diameter 6001 is formed by a plurality of leaflets 6002. The leaflets 6002 may be arranged in a generally circular pattern around the central axis of the adjustable valve. In some embodiments, the plurality of leaflets 6002 are arranged in an equidistant pattern.

In some embodiments, the leaflets 6002 may comprise curved edges. In some embodiments, each leaflet 6002 is pivoted about a pivot pin 6003, wherein the rotation of the pivot pin 6003 about its own axis causes the leaflets to rotate in the same direction about the axis of said pivot pin 6003.

In some embodiments, the pivot pins 6003 are mounted onto a mounting layer 6010 and each pivot pin 6003 is connected to a shaft 6004. In some embodiments, the shaft 6004 may extend radially outwards, such that the rotation of the shaft 6004 about the central axis of the pivot pin 6003, results in the rotation of the pivot pin 6003 and thus the rotation of the leaflet 6002 about the axis of the pivot pin 6003. The degree of rotation of the plurality of leaflets 6002 about the axes of their respective pivot pins 6003 controls the inner diameter 6001, and the second inner diameter 6009 that is comprised by the plurality of leaflets 6002.

In some embodiments, the plurality of shafts 6004 are attached to pin shaft rotators 6012 which are connected to a driving member 6005. In some embodiments, driving member 6005 comprises a diameter wheel, which comprises a hollow center 6011.

The driving member 6005 contains a plurality of pin shaft rotators 6012. In some embodiments, the pin shaft rotators 6012 are equidistant. In some embodiments, the number of pin shaft rotators 6012 is equal to the number of pivot pins 6003.

In some embodiments, the pin shaft rotators 6012 comprise rectangular extrusions. In some embodiments, the pin shaft rotators 6012 comprise pivot pins that are connected to the driving member 6005. In some embodiments, the pin shaft rotators 6012 are connected to the driving member 6005 in an equidistant arrangement.

The driving member 6005 may be rotated with a handle 6006 about the central axis of the adjustable valve, causing the pin shaft rotators 6012 to rotate as well as the plurality shafts 6004 to rotate in the same direction, however about the axes of their respective pivot pins 6003, which in turn causes the leaflets 6002 to rotate about the axes of the pivot pins 6003. Rotation of the driving member 6005 about the central axis of the adjustable valve in the first direction causes the leaflets 6002 to rotate towards the central axis of the adjustable valve, and thus decrease the inner diameter. Rotation of the driving member 6005 in a second direction, that is opposite to the first direction, causes the leaflets 6002 to rotate away from the central axis of the valve, and thus increase the diameter of the valve.

In some embodiments, to prevent rotation past the first inner diameter, the driving member 6005 comprises at least one diameter lock pin 6007. The diameter lock pin 6007 is disposed into a diameter lock groove 6008. As the driving member 6005 rotates, the diameter lock pin 6007 will contact the edge of the diameter lock groove 6008 to prevent further rotation in a particular direction.

Breakable Adhesive:

In some embodiments (not shown), the elongate rigid member 1301 surfaces that are directly in contact with another surface of a elongate rigid member 1301 has a layer of sealing adhesive such that no fluid leaking gaps are present. In some embodiments, the sealing adhesive is breakable when the elongate rigid members 1301 are expanded. In some embodiments, the sealing adhesive is biocompatible.

With reference to FIGS. 171-172: elongate rigid members with gaskets.

In some embodiments the elongate rigid member 6201 surfaces that are directly in contact with another elongate rigid member 6201 surface comprise a gasket 6301. In some embodiments, the gasket 6301 create a seal between the gaps between each adjacent elongate rigid member 6201 when they are unexpanded.

In some embodiments, each side of gasket 6301 either comprises at least one first gasket feature 6302 and at least one second gasket feature 6303 such that the first gasket features 6302 and second gasket features 6303 are complimentary. In some embodiments, the complimentary features comprise male and female features. In some embodiments, the complimentary features comprise tongue and groove.

In some embodiments, the gasket 6301 is comprised from a rubber-based material.

Telescoping Gasket:

In some embodiments, the expandable cannula device 100 comprises a gasket 6801 that surrounds the plurality of elongate rigid members 1301. In some embodiments, the gasket 6801 is a telescoping gasket.

In some embodiments, the gasket 6801 is housed within the secondary housing 1201, such that it may be retracted proximally within the secondary housing 1201. When the gasket handle 6802 is pulled in a distal direction towards the plurality of elongate rigid members 1301, the gasket 6801 thus is brought out of the secondary housing 1201 in order to surround the plurality of elongate rigid members 1301 proximal portions that are not penetrated into the tissue. The distal most edge of the gasket 6801 makes contact with the top most layer of the subject tissue, such as skin, and therefore creates a closed environment around the expanded passage 1309. This closed environment prevents leakage of fluids, such as insufflated gas, from the lumen of the expandable cannula device 100 to the external environment and vice versa.

In some embodiments of a gasket 6801, the proximal portion of the gasket is rigid, and the distal part is comprised of gasket material such as rubber.

In some embodiments of a gasket 6801, the distal most edge of the gasket comprises an adhesive layer.

In other embodiments, the gasket 6801, may be housed within the first or second housings of any of the previously described inventions and embodiments.

With reference to FIGS. 177-180: expandable sealing sleeve.

In some embodiments, the expandable cannula device 100 comprises an expandable sleeve that surrounds the outer surface of the plurality of the elongate rigid members 6201.

In some embodiments, when the elongate rigid members 6201 comprise an unexpanded passage 1308, the sleeve is at a contracted 6401. However, when the elongate rigid members are away from each other and defining an expanded passage 1309 the expandable sleeve becomes expanded 6402 in order to seal the spaces in between the plurality of the elongate rigid members 6201.

In some embodiments, the expandable sleeve is made from a flexible and stretchable material. In some embodiments, the expandable sleeve comprises at least one layer of material. In some embodiment, the expandable sleeve comprises expandable mesh structures. In some embodiments, the expandable sleeve is glued to the outer surface of elongate rigid members 6201. In some embodiments, expandable sleeve is attachably detachable from the expandable cannula device 100.

In some embodiments, the expandable sleeve comprises a central lumen, such that the expandable cannula device 100 is insertably removable from the lumen of expandable sleeve.

In some embodiments, the expandable sleeve is heat-shrinkable.

With reference to FIGS. 181-186: coiled sheet member.

This embodiment of an expandable cannula device 100 shows a coiled sheet member 5701 being disposed in the unexpanded passage 1308 of the expandable cannula device 100, wherein the coiled sheet member 5701 further comprises a central passage. In some embodiments, the coiled sheet member 5701 is comprised of a resilient material. In some embodiments, the resilient material is metallic or comprised of a metallic composite. In some embodiments, the coiled sheet member 5701 is made from plastic material.

In some embodiments, the plurality of unexpanded elongate rigid members 1301 keep the coiled sheet member 5701 in its coiled state by applying pressure and constricting the available diameter for the coiled sheet member 5701.

When the expandable cannula 100 is expanded such that the plurality of elongate rigid members 1301 are away from each other and an expanded passage 1309 is created, the coiled sheet member 5701 becomes an uncoiled sheet member 5702 such that a seal is formed along the internal circumference of the expanded passage 1309.

In some embodiments (not shown), the coiled sheet member 5701 comprises outer surface features, that are compatible with inner surface features of the elongate rigid members 1301. In some embodiments, the outer surface features can slide in the inner surface features when the coiled sheet member 5701 uncoils to become an uncoiled sheet member 5702.

In some embodiments, the outer surface features may comprise tongues and the inner surface features comprise complimentary grooves, or vice versa.

In some embodiment the uncoiled sheet member 5702 creates a sealing mechanism against fluid leakage through the instrument.

With reference to FIGS. 187-190: accordioned sleeve between struts.

In some embodiments, the expandable cannula device 100 comprises a contracted sleeve 6501 attached to the sides of each adjacent pair of the plurality of elongate rigid members 6201. In some embodiments, the contracted sleeve 6501 is configured to be in an accordioned state. When the elongate rigid members 6201 move away from each other when the expandable cannula device 100 is expanded, the contracted sleeve 6501 becomes expanded 6502 in order to seal the spaces in between the plurality of the elongate rigid members 6201.

In other embodiments, the contracted sleeve 6501 may be folded in other shapes or configurations. In some embodiments, the folded portions of the contracted sleeve 6501 are outside the unexpanded passage 1308. In some embodiments, the folded portion of the contracted sleeve 6501 are inside the unexpanded passage 1308.

With reference to FIGS. 191-194: magnetic sleeve.

In some embodiments, a sealing sleeve comprises a magnetic sleeve 6601 and the elongate rigid members 6201 are made from a magnetic material.

In some embodiments, the magnetic sleeve 6601 is disposed onto the external surface of each pair of the plurality of adjacent elongate rigid members 6201.

In some embodiments, the magnetic sleeve 6601 comprises a flexible portion 6602 that conforms to the external shape of the elongate rigid members 6201. The magnetic sleeve will seal the gap 6603 between the expanded adjacent elongate rigid members 6201, which is adjacent and may be in direct contact with a second elongate rigid member 6201 when the expandable cannula device 100 comprises an unexpanded passage 1308. The expansion of the elongate rigid members 6201 of the expandable cannula device 100, causes the magnetic sleeve 6601 to slide on the external surfaces of the first and second elongate rigid members 6201 and seal the gap 6603.

In some embodiments (not shown), a portion of the magnetic sleeve 6601 is permanently fixed to the external surface of a first elongate rigid member 6201, which is adjacent and may be in direct contact with a second elongate rigid member 6201 when the expandable cannula device 100 comprises an unexpanded passage 1308. The remaining portion of the magnetic sleeve 6601 is magnetically attached to the external surface of the second elongate rigid member 6201. The expansion of the elongate rigid members 6201 of the expandable cannula device 100, causes the magnetically attached portion of the sleeve to slide onto the external surface of the second elongate rigid member 6201 and cover the gap 6603 in between the expanded passage 1309.

With reference to FIGS. 195-200: sliding sleeve.

In some embodiments, for each adjacent pair of the plurality of elongate rigid members 6201, a sliding sleeve 6701 is provided that is mechanically connected to at least one of the pair of elongate rigid members 6201.

In some embodiments, the sliding sleeve 6701, comprises a flexible center piece 6705, is mechanically connected by movable connection features 6702 to each of two adjacent elongate rigid members 6201, which contain tracks 6703 that guide the movements of the movable connection features 6702. In some embodiments, the movable connection features 6702 are slidable.

In some embodiments, the movable connection features 6702 comprise at least one wheel that connects to the track 6703 on each of the two adjacent elongate rigid members 6201. Each elongate rigid member 6201 comprises a track 6703 in which the movable connection features 6702 slide. In some embodiments, the track 6703 comprises a groove. In some embodiments, the track 6703 comprises a wheel rail.

In some embodiments, the at least one movable connection features 6702 are complimentary to the track 6703. In some embodiments, the movable connection feature 6702 comprises a tongue.

When the gap increases between adjacent elongate rigid members 6201 as the elongate rigid members 6201 transition from the contracted to the expanded state, the sliding sleeve 6701 to slides towards said gap in order to seal it.

When the expandable cannula device 100 comprises an unexpanded passage 1308, the flexible center piece 6705 will seal the gap between adjacent unexpanded elongate rigid members 6201. When the expandable cannula device 100 is configured with an expanded passage 1309, the flexible center piece 6705 changes its conformation to seal the gap between adjacent expanded elongate rigid members 6201 to prevent gas leakage.

In some embodiments, the sliding sleeve 6701 comprises a side sealant 6704 that seals the gap between the sliding sleeve 6701 and the elongate rigid member 6201 in order to prevent fluid leakage.

In some embodiments (not shown), a sliding sleeve 6701 is composed entirely of a flexible material. The mechanical sliding seal is mechanically connected to two adjacent elongate rigid members 6201 via tongue features that are guided in the tracks 6703 of the elongate rigid members 6201. In some embodiments, the tracks 6703 are horizontal. This enables the sliding sleeve 6701 to slide horizontally towards the gap between adjacent elongate rigid members 6201 as the elongate rigid members 6201 transition from the contracted to the expanded state. The sliding sleeve 6701 will seal the gap between adjacent contracted elongate rigid members 6201 and will change its conformation to seal the gap between adjacent expanded elongate rigid members 6201 to prevent gas leakage. The side sealant 6704 is configured to seal the gap between the sliding sleeve 6701 and the elongate rigid member 6201 to prevent gas leakage.

With reference to FIG. 201: cannula depth markers.

The external surface of at least one of the plurality of elongate rigid members 6201 comprises graduated markers 6901 for indicating depth of insertion into tissue of a subject.

In some embodiments, the graduated markers 6901 are printed onto the outer surface of said elongate rigid members 6201. In some embodiments, the graduated markers 6901 are engraved on the outer surface of the elongate rigid members 6201. In some embodiments, the depth of insertion of the distal tip of the elongate rigid member 6201 inside the tissue is shown via the graduated markers 6901. In other embodiments, the graduated markers 6901 may reflect the amount of the proximal part of the elongate rigid members 6201 that has not penetrated the tissue.

With reference to FIGS. 202-204: cannula with an insufflation mechanism.

In some embodiments, the expandable cannula device 100 further comprises a second insufflation port.

In some embodiments, a stopcock 5802 is connected to the first housing 1101 of the expandable cannula device 100, such that a fluid track is created from stopcock 5802 to the central passage of the expandable cannula device 100.

With reference to FIGS. 205-207: incision guide mechanism.

In some embodiments, the expandable cannula device 100 comprises a guide for guiding a blade or an energy cutting device to create an incision of a predetermined dimension and shape.

In some embodiments, the incision making guide 7001 may be part of the first housing 1101 or second housings 1201 of the expandable cannula device 100.

In some embodiments, the incision making guide 7001 has telescoping or retractable mechanism to facilitate moving it from a proximal position to a distal position of the cannula.

In some embodiments, the expandable cannula device 100 is inserted in the tissue at the unexpanded state, the incision making guide 7001 is brought distally, or is expanded, in order to interface the top most layer of the tissue, such as skin.

When the user wants to expand the expandable cannula device 100, unexpanded incision making guide 7001 may be brought down to skin level via a telescoping mechanism 7003, thus becoming an expanded incision making guide 7002.

The incision making guide 7001 comprises demarcations to help the user in creating an appropriate skin level incision prior to expanding the expandable cannula device 100.

In some embodiments, the incision making guide 7001 can be retracted and returned to its unexpanded position after an incision is made.

With reference to FIG. 208: position tracking.

The expandable cannula device 100 comprises at least one live position tracking feature 7201. In some embodiments, the live position tracking feature 7201 comprises a plurality of objects that are reflective to electromagnetic energy or are emitters of electromagnetic energy wherein said emitted or reflected energy is detectable by an external position tracking system.

In some embodiments, the live position tracking feature 7201 may be used by an external navigation system to track the position of the expandable cannula device 100 during use. In some embodiments, live position tracking feature 7201 and external navigation systems may track the level of cannula expansion.

In some embodiments (not shown), live position tracking feature 7201 may be placed on other members that are inserted or used with the expandable cannula device 100, such as an actuation member, or insertable member, or obturator.

In some embodiments, the live position tracking feature 7201 comprise electromagnetic wave emitting markers. In some embodiments, the live position tracking feature 72011 comprise electromagnetic wave reflective markers. In some embodiments, the live position tracking feature 7201 comprise infrared reflective or emitting markers.

In some embodiments, the live position tracking feature 7201 may comprise x-ray opaque dye, coating or material.

In some embodiments, the live position tracking feature 7201 may be attached to the expandable cannula device 100, at a distance away from it, via an extension arm.

In some embodiments (not shown), the expandable cannula device 100, may be held by an external mechanical member. In some embodiments, the mechanical member may be a pneumatic or hydraulic or robotic arm.

Inflatable Sac for Expanding Struts:

In some embodiments (not shown), the expandable cannula device 100 may further comprise a fluid-filled chamber configured to transfer the fluid into an inflatable sac connected to the elongate rigid members.

In some embodiments (not shown), the fluid filled chamber may be housed inside the first housing, or second housing, where it would comprise a central lumen. In some embodiments, chamber may comprise a piston that is connected to the first housing, or second housing, or at least one of the elongate rigid members, such that the expansion of the expandable cannula device 100 causes the piston to become pressed and thus transfer the fluid into the inflatable sacs. In some embodiments, the contraction of the expanded cannula device 100, reverses the action of the piston, and causes the fluid to be transferred back into the chamber.

In some embodiments (not shown), at least one inflatable sac is disposed between two adjacent elongate rigid members. In some embodiments (not shown), the inflatable sac traverses the length of the elongate rigid member, such that when the expandable cannula device 100 is expanded and an expanded passage 1309 is created by the plurality of elongate rigid members, the inflatable sacs become inflated and seal the gaps in between the elongate rigid members.

With reference to FIGS. 209-217: blades in the elongate rigid members concept.

In some embodiments, the expandable cannula device 100 may be comprising one uniform passage. In some embodiments, the expandable cannula device 100 comprises a plurality of elongate rigid members 2001, wherein at least one blade 5905 is disposed in an exterior wall of each of the plurality of elongate rigid members 2001. Wherein the blade 5905 comprises a sharp edge facing an exterior surface of the elongate rigid member 2001 and a spine 5907 facing an interior surface of the elongate rigid members 2001.

At least one biasing member 5906 disposed in a portion of the wall of the elongate rigid member 2001, the biasing member 5906 biases the at least one blade 5905 away from the exterior surface of the elongate rigid member 2001. In some embodiments, the biasing member 5906 comprises a compression spring.

The blade 5905 is movable such that: the sharp edge is embedded in the exterior wall and the spine 5907 is exposed from the interior surface when no force toward the exterior surface is applied on the spine 5907; and the sharp edge is exposed from the exterior surface when a force toward the exterior surface is applied on the spine 5907.

In some embodiments, the force can be exerted on the spine 5907 via an insertable member 5901, such that the insertion of the insertable member 5901 applies a force toward the exterior surface on the spine. In some embodiments, the insertable member 5901 comprises a first circumference 5902, and a portion of the insertable member 5901 comprising a second circumference 5903 that is larger than the first circumference 5902, such that a force toward the exterior surface on the spine 5907 is applied by the insertable member 5901 when a portion of the insertable member 5901 of the second circumference 5903 is aligned with the spine 5907. In some embodiments, the biasing member 5906, such as the spring, becomes compressed thus allowing the blade 5905 to move out of the walls of elongate rigid member 2001; and a force toward the exterior surface on the spine 5907 is not applied by the insertable member 5901 when a portion of the insertable member 5901 of the first circumference 5902 is aligned with the spine.

In some embodiments, the insertable member 5901 comprises an obturator.

In some embodiments, the biasing member 5906, such as the spring returns to its uncompressed state, thus biasing the blade 5905 to a position within the walls of the elongate rigid member 2001.

In some embodiments, the second circumference 5903 comprises a surface 5904 that is complimentary to a spine surface 5908 to reduce contact friction. In some embodiments, the surface 5904 and spine surface 5908 comprise complimentary tapers.

In some embodiments, after causing the blade 5905 to be exposed during insertion of an insertable member 5901, it may then be removed from the passage of the expandable cannula device 100 without causing a second exposure of the blade 5905 during pullback; this can be accomplished by rotating the obturator such that the spine 5907 is aligned with a portion of the obturator comprising a first circumference 5902. Once the alignment is achieved, the obturator can then be pulled out of the cannula without causing a secondary bladed exposure.

Method and Use:

With reference to the previous descriptions, the expandable cannula device 100 may be used for creating a passage into a subject, said method comprising inserting the expandable cannula device 100 through a tissue the subject and then expand the expandable cannula device 100 by moving the elongate rigid members away from each other. In some embodiments for example, the expandable cannula device 100 may start at a passage with 3 mm inner diameter, and then be expanded to passage with 12 mm diameter or any diameter in between 3 mm and 12 mm.

With reference to the previous descriptions, the expandable cannula device 100 may be used for making an entry hole, thereby creating an orifice into a mammalian subject.

With reference to the previous descriptions, the expandable cannula device 100 may be used for enlarging an orifice by moving the plurality of elongate rigid members away from each other. In some embodiments for example, the expandable cannula device 100 may start at a passage with 3 mm inner diameter, and then be expanded to passage with 12 mm diameter or any diameter in between 3 mm and 12 mm.

With reference to the previous descriptions, the expandable cannula device 100 may be used for allowing movements of instruments within and through the expandable cannula device 100. In some embodiments, minimal invasive tissue visualization and surgical instruments may be used. In some embodiments, laparoscopic visualization and surgical instruments may be used, and in some embodiments, minimal invasive brain visualization and surgical instruments may be used.

In some of any of the previously described embodiments, the expandable cannula device 100, and any of its components, add-ins and attachments may be fabricated from optically transparent or translucent material.

The embodiments of the present disclosure described above are intended to be examples only. The present disclosure may be embodied in other specific forms. Alterations, modifications and variations to the disclosure may be made without departing from the intended scope of the present disclosure. While the systems, devices and processes disclosed and shown herein may comprise a specific number of elements/components, the systems, devices and assemblies could be modified to include additional or fewer of such elements/components. For example, while any of the elements/components disclosed may be referenced as being singular, the embodiments disclosed herein could be modified to include a plurality of such elements/components. Selected features from one or more of the above-described embodiments may be combined to create alternative embodiments not explicitly described. All values and subranges within disclosed ranges are also disclosed. The subject matter described herein intends to cover and embrace all suitable changes in technology.

We claim:

1. A cannula device, comprising:
   a first housing defining a first throughbore aligned along a central axis;
   a second housing defining a second throughbore aligned with the first throughbore along the central axis, the second housing moveable in an axial direction along the central axis with respect to the first housing without being rotatable relative to one another; and
   a plurality of elongate rigid members extending distally from the first and second housings that cooperatively define a passage axially aligned with the first throughbore along the central axis between proximal ends and distal tips of the elongate rigid members;
   wherein the proximal ends of the elongate rigid members and the first housing comprise first tracks including inter-engaging first tongues and first guides oriented diagonally relative to the central axis, and the second housing and the elongate rigid members comprise second tracks including second tongues and second guides such that axial movement of the second housing with respect to the first housing along the central axis without relative rotation causes the plurality of elongate rigid members to move radially outwardly and diagonally with respect to the central axis to move away from each other and increase a size of the passage.

2. The cannula device of claim 1, wherein each of the elongate rigid members includes a first tongue of the first tongues that slides in a corresponding first guide of the first guides in the first housing.

3. The cannula device of claim 1, wherein the second tracks are oriented radially relative to the central axis.

4. The cannula device of claim 3, wherein each of the elongate rigid members includes a second tongue of the second tongues that slides in a corresponding second guide of the second guides in the second housing.

5. The cannula device of claim 4, wherein the second tongue is located distal to the first tongue on each of the elongate rigid members.

6. The cannula device of claim 1, wherein the first housing is at least partially received in the second throughbore of the second housing.

7. The cannula device of claim 1, wherein each of the distal tips of the rigid members is tapered to facilitate insertion.

8. The cannula device of claim 1, wherein the second housing is configured to at least partially surround the first housing.

9. The cannula device of claim 1, further comprising a centering mechanism for axially aligning the first throughbore and the second throughbore.

10. The cannula device of claim 9, wherein the centering mechanism comprises a plurality of concentricity features on the second housing and a plurality of complimentary concentricity features on the first housing.

11. The cannula device of claim 10, wherein the concentricity features comprise a plurality of pins and the complimentary concentricity features comprise a plurality of receptacles for receiving the plurality of pins.

12. The cannula device of claim 1, further comprising an obturator configured to be inserted into the first housing throughbore, all the way through the passage such that a tip of the obturator is exposed prior to inserting the cannula device into tissue.

13. A cannula device, comprising:
   a first housing defining a first throughbore aligned along a central axis;
   a second housing defining a second throughbore aligned with the first throughbore along the central axis, the second housing moveable in an axial direction along the central axis with respect to the first housing without being rotatable relative to one another; and
   a plurality of elongate rigid members extending distally from the first and second housings and cooperatively defining a passage axially aligned with the first throughbore along the central axis between proximal ends and distal tips of the elongate rigid members,
   wherein the proximal ends of the elongate rigid members and the first housing comprise first tracks including inter-engaging first tongues and first guides oriented diagonally relative to the central axis, and the second housing and the elongate rigid members comprise second tracks including second tongues and second guides oriented radially relative to the central axis such that axial movement of the second housing relative to the first housing along the central axis without relative rotation causes the first tongues to slide diagonally along the first guides and the second tongues to slide radially along the second guides to move the proximal ends of the elongate rigid members away from each other and increase a size of the passage.

14. A method for performing a medical procedure within a subject's body, comprising:
   providing a cannula device including a first housing defining a first throughbore aligned along a central axis, a second housing defining a second throughbore aligned with the first throughbore, and a plurality of elongate rigid members extending distally from the first and second housings that cooperatively define a passage axially aligned with the first throughbore;
   inserting distal tips of the elongate rigid members through tissue into the subject's body;
   expanding the cannula by moving the second housing relative to the first housing along the central axis without relative rotation, thereby causing proximal ends of the elongate rigid members to move outwardly and diagonally with respect to the central axis to move the elongate rigid members away from each other and increase a size of the passage; and
   introducing one or more instruments through the passage to perform the medical procedure within the subject's body.

15. The method of claim 14, wherein moving the second housing relative to the first housing causes first tongues of the elongate rigid members to slide diagonally along first guides of the first housing and second tongues of the elongate rigid members to slide radially along second guides of the second housing to move the proximal ends of the elongate rigid members away from each other and increase the size of the passage.

16. The method of claim 14, wherein the cannula is expanded to open the passage to a diameter between 3 mm and 12 mm.

17. The method of claim 14, wherein the inserting distal tips of the elongate rigid members through tissue into the subject's body creates an entry hole through tissue into the subject's body.

18. The method of claim 14, further comprising, before the inserting the distal tips of the elongate members through tissue, inserting an obturator through the passage such that a tip of the obturator is exposed, and wherein the obturator tip is used to penetrate the tissue to create an entry hole into the subject's body.

19. The method of claim 18, further comprising removing the obturator from the cannula device before expanding the cannula device.

* * * * *